US012618835B2

(12) United States Patent
Li et al.

(10) Patent No.: US 12,618,835 B2
(45) Date of Patent: May 5, 2026

(54) MULTIPLEX MICROELECTRODE ARRAY FOR DETECTION OF PROTEASES AS BIOMARKERS

(71) Applicants: Kansas State University Research Foundation, Manhattan, KS (US); United States of America as Represented by the Administrator of NASA, Washington, DC (US)

(72) Inventors: Jun Li, Manhattan, KS (US); Duy H. Hua, Manhattan, KS (US); Morgan James Anderson, Moffett Field, CA (US); Jessica Erin Koehne, Moffett Field, CA (US); Meyya Meyyappan, Moffett Field, CA (US)

(73) Assignees: Kansas State University Research Foundation, Manhattan, KS (US); United States of America as Represented by the Administer of NASA, Washington, DC (US)

( * ) Notice: Subject to any disclaimer, the term of this patent is extended or adjusted under 35 U.S.C. 154(b) by 580 days.

(21) Appl. No.: 17/729,494

(22) Filed: Apr. 26, 2022

(65) Prior Publication Data

US 2022/0349880 A1     Nov. 3, 2022

Related U.S. Application Data

(60) Provisional application No. 63/179,848, filed on Apr. 26, 2021.

(51) Int. Cl.
   *G01N 33/543* (2006.01)

(52) U.S. Cl.
   CPC ................................ *G01N 33/5438* (2013.01)

(58) Field of Classification Search
   None
   See application file for complete search history.

(56) References Cited

U.S. PATENT DOCUMENTS

| | | | | |
|---|---|---|---|---|
| 6,740,518 | B1 * | 5/2004 | Duong | G01N 27/3277 |
| | | | | 435/7.1 |
| 7,939,734 | B1 | 5/2011 | Li et al. | |
| 9,850,520 | B2 | 12/2017 | Li et al. | |
| 2005/0100974 | A1 * | 5/2005 | Duffy | G06T 7/70 |
| | | | | 435/23 |
| 2015/0011421 | A1 * | 1/2015 | Li | C12Q 1/37 |
| | | | | 506/18 |

FOREIGN PATENT DOCUMENTS

| | | | | | |
|---|---|---|---|---|---|
| WO | WO-2012144631 | A1 * | 10/2012 | | G01N 27/4145 |
| WO | WO-2018071556 | A1 * | 4/2018 | | C07K 14/81 |
| WO | WO-2018222820 | A1 * | 12/2018 | | A61B 5/4839 |
| WO | WO-2021078971 | A2 * | 4/2021 | | B01L 3/5085 |

OTHER PUBLICATIONS

Li, et al., "Development of Multiplex Electrode Array Sensors for Proteases Activity Profiling Toward Cancer Diagnosis", ECS Meeting Abstracts, 2021, MA2021-02(56), p. 1654.
Song, et al., "Electrochemical Activity Assay for Protease Analysis Using Carbon Nanofiber Nanoelectrode Arrays", Anal. Chem., 2019, 91(6), pp. 3971-3979.
Anderson, et al., "Simultaneous, multiplex quantification of protease activities using a gold microelectrode array", Biosens Bioelectron, 2020, 165, 22 pages.
Swisher, et al., "Quantitative Electrochemical Detection of Cathepsin B Activity in Breast Cancer Cell Lysates Using Carbon Nanofiber Nanoelectrode Arrays toward Identification of Cancer Formation", Nanomedicine, 2015, 11(7), pp. 1695-1704.
Global Market Insights, "Cancer Diagnostics Market", 2021, GMI2406, retrieved from: https://www.gminsights.com/industry-analysis/cancer-diagnostics-market.
U.S. Cancer Statistics Data Visualizations Tool, based on 2020 submission data (1999-2018), U.S. Cancer Statistics Working Group, U.S. Department of Health and Human Services, Centers for Disease Control and Prevention and National Cancer Institute, retrieved from: https://www.cdc.gov/cancer/uscs/dataviz/index.htm.
Cancer.Net., "Breast Cancer: Diagnosis", 2020, retrieved from: https://www.cancer.net/cancer-types/breast-cancer/diagnosis.
Swisher, et al., "Electrochemical Protease Biosensor Based on Enhanced AC Voltammetry Using Carbon Nanofiber Nanoelectrode Arrays", J Phys Chem C., 2013, 117(8), pp. 4268-4277 (abstract attached).
Swisher, et al., "Quantitative Electrochemical Detection of Cathepsin B Activity in Complex Tissue Lysates using Enhanced AC Voltammetry at Carbon Nanofiber Nanoelectrode Arrays", Biosens Bioelectron., 2014, 56, pp. 129-136 (abstract attached).
Song, et al., "Quantitative Detection of Cathepsin B Activity in Neutral pH Buffers Using Gold Microelectrode Arrays: Toward Direct Multiplex Analyses of Extracellular Proteases in Human Serum", ACS Sensors., 2021,6(10), pp. 3621-3631.
Roy, et al., "Candidate prognostic markers in breast cancer: focus on extracellular proteases and their inhibitors", Breast Cancer: Targets and Therapy, 2014, 6, pp. 81-91.
Koblinski, et al., "Unraveling the role of proteases in cancer", Clin Chim Acta., 2000, 291, pp. 113-135.
Lee, et al., "Extracellular proteases as targets for treatment of cancer metastases", Chemical Society Reviews, 2004, 33(7), pp. 401-409 (abstract attached).

(Continued)

*Primary Examiner* — Gregory S Emch
*Assistant Examiner* — Fernando Lvich
(74) *Attorney, Agent, or Firm* — Hovey Williams LLP; Crissa A. Cook

(57)     ABSTRACT

An electrochemical method for measuring the activity of biomarkers using microelectrode arrays functionalized with peptide consensus sequences and redox reporter moieties. Contact of the arrays with a biological sample containing one or more target biomarkers results in cleavage of the peptides and changes the electric current across the array in a quantifiable manner indicating not just the presence of the target biomarker in the sample, but its activity.

13 Claims, 30 Drawing Sheets

Specification includes a Sequence Listing.

(56)                    References Cited

OTHER PUBLICATIONS

Turk, "Targeting proteases: successes, failures and future prospects", Nat Rev Drug Discov., 2006, 5(9), pp. 785-799 (abstract attached).

Turk, et al., "Protease signalling: the cutting edge", The EMBO Journal, 2012, 31(7), pp. 1630-1643.

Ivry, et al., "Global Protease Activity Profiling Provides Differential Diagnosis of Pancreatic Cysts", Clin Cancer Res., 2017, 23(16), pp. 4865-4874.

Sanman, et al., "Activity-Based Profiling of Proteases", Annu Rev Biochem., 2014, 83(1), pp. 249-273 (abstract attached).

Ong, et al., "Recent developments in protease activity assays and sensors", Analyst, 2017, 142(11), pp. 1867-1881.

Rakha, et al., "Prognostic markers in triple-negative breast cancer", Cancer, 2007, 109(1), pp. 25-32.

Rakashanda, et al., "Role of proteases in cancer: A review", Biotech & Mol Biol Rev., 2012, 7, pp. 90-101.

Ohtsuka, et al., "Electrochemical assay of plasmin activity and its kinetic analysis", Analytical Biochemistry 385 (2009) 293-299.

Adjemian, et al., "Cleavage-Sensing Redox Peptide Monolayers for the Rapid Measurement of the Proteolytic Activity of Trypsin and r-Thrombin Enzymes", Langmuir 2010, 26(12), 10347-10356.

* cited by examiner

Fig. 12

Scheme. Synthesis of substrate peptide 26: H₂N(CH₂)₄-CO-Pro-Arg-Thr-Ile-Ser-Ala-NH-CH₂-Fc (SEQ ID NO:20).

Peptide 26

MULTIPLEX MICROELECTRODE ARRAY FOR DETECTION OF PROTEASES AS BIOMARKERS

CROSS-REFERENCE TO RELATED APPLICATIONS

The present application claims the priority benefit of U.S. Provisional Patent Application Ser. No. 63/179,848, filed Apr. 26, 2021, entitled MULTIPLEX MICROELECTRODE ARRAY FOR DETECTION OF PROTEASES AS BIO-MARKERS, incorporated by reference in its entirety herein.

FEDERALLY SPONSORED RESEARCH OR DEVELOPMENT

This invention was made with government support under R01 CA217657 awarded by the National Cancer Institute of the National Institutes of Health. The government has certain rights in the invention.

SEQUENCE LISTING

This application contains a sequence listing in computer readable format (CRF), submitted via EFS-Web as an ASCII text file entitled "SequenceListing," created on Apr. 26, 2022, as 4,126 bytes, to serve as both the paper copy and CRF in compliance with 37 C.F.R. 1.821. The content of the ASCII text file is hereby incorporated by reference herein.

BACKGROUND

Field

Electronic chips, micro- and nanoelectrode arrays, and assays for simultaneous, multiplex profiling of the protease biomarkers, which can be used for advanced medical diagnosis, treatment monitoring and protease inhibitor screening.

Description of Related Art

Proteases play important roles as protein-degrading enzymes in many metabolic processes, including immune response, wound healing, food digestion, cell cycle, and protein recycling. Proteases hydrolyze proteins based on recognition of specific peptide sequences. Two viral cysteine proteases, the main protease (Mpro, also called 3C like protease, 3CLpro) and the papain like protease (PLpro) were also found to play critical mediating role in viral production and transcription in the coronavirus SARS-COV-2 which caused the COVID-19 global pandemic. Proteases also act as key signaling molecules in progression of many diseases such as cancer, neurodegenerative diseases, cardiovascular diseases, diabetes, and other inflammatory diseases. For example, aberrant overexpression of proteases has been reported in breast cancer, colorectal cancer, gastric cancer, and prostate cancer. It is well-known that proteases play diverse roles in tumor growth, invasion, and metastasis. Several matrix metalloproteinases (MMPs), such as MMP-2 and MMP-9, can affect signaling pathways and growth factors to enhance tumor growth. Numerous proteases, including cathepsins, kallikreins, and other serine proteases, facilitate the spread of cancer to distant organs by degrading the extracellular matrix. For example, proteases can degrade E-cadherin, a tumor suppressor and an essential protein in the formation of adherent junctions to bind cells with each other. Small molecule drugs targeting protease inhibition have attracted great attentions for cancer treatment. However, it remains a great challenge to understand the complex protease signaling and develop specific inhibitors. First, there are about 600 known proteases in humans, and they interact with each other in a complex network. Second, individual proteases have very limited indicative value because they only represent one aspect of carcinogens. Third, the protease levels in humans are extremely low. Hence, there is a strong demand for developing highly sensitive and highly specific bioanalytical techniques that can detect a group of protease biomarkers in parallel, rather than a single one each time. Particularly, the activity of proteases in extracellular space is significantly reduced and subject to rapid inactivation. Developing new techniques that can directly detect extracellular protease activity is critical for disease diagnostics.

Cathepsin B is a member of the cysteine cathepsin family consisting of 11 lysosomal hydrolases. It is linked to general protein degradation in lysosomes. Initially, cathepsin B is synthesized on the rough endoplasmic reticulum (RER) as a proenzyme consisting of 339 amino acids with a signal peptide of 17 amino acids. After post-translational modification, proenzyme cathepsin B undergoes autocatalytic activation (normally in mild acidic conditions) and converts into mature cathepsin B by proteolytic cleavage and dissociation of the blocking peptide. Increased cathepsin B levels have been observed in many types of cancer such as prostate cancer, melanomas cancer and breast cancer. Its activity is essential for tumor migration, invasion, and metastases. However, the link between the cathepsin B concentration and activity is not clear. Developing a rapid, sensitive and specific method for detecting cathepsin B activity is critical for cancer diagnosis and therapeutic efficacy assessment.

Currently, protease detection can be classified into two broad categories, i.e., affinity-based and activity-based techniques. The affinity-based technique detects the protease concentration by capturing proteases using the specific probe-target affinity such as enzyme-linked immunosorbent assay (ELISA) and aptamer sensors. Although ELISA has very high selectivity and sensitivity, it is time-consuming, expensive and can only be operated in the laboratory by skilled personnel. Furthermore, it does not indicate the activity of target proteases because both the proenzyme and mature enzyme may have common epitopes that can bind to the antibodies. Missing information of the important biological functions of the proteases limits its effectiveness in cancer diagnosis. The activity-based analyses primarily focus on detecting the biological function of proteases, i.e., the proteolysis rate of the peptide substrate by the cognate proteases. This category of analysis is more relevant to cancer progression. Activity-based analyses preclude proenzymes which do not have any preformed active site or whose preformed active sites are blocked by a peptide unit. Only the active mature proteases with the binding pocket exposed can be detected. For instance, a group of sensors known as activity-based probes (ABPs) can covalently bind with a protease's active site through an addition or displacement of a warhead of the substrate peptide, which are useful for in vivo imaging or immunoblotting analyses. Fluorogenic techniques based on fluorescence resonance energy transfer (FRET) are another type of activity-based biosensor for protease detection. A pair of fluorescence donor (fluorophore) and acceptor (quencher) is covalently attached within a short distance (<10 nm) at the opposite sides of the cleavage site in the peptide substrate. FRET occurs when the emission spectrum of the donor overlaps with the absorption spectrum of the acceptor. The acceptor and donor are separated apart when the peptide substrate is hydrolyzed by proteases and thus the fluorescence emission of the donor is restored. The rise of the fluorescence intensity can be recorded in real-time to reveal the kinetics of the proteolysis process. Such fluorogenic techniques are highly sensitive and selective. However, the fluorescence signal can be easily affected by auto-fluorescence or quenching of indigenous molecules, especially in a complex biological sample such as plasma or cell lysates. Moreover, the broad spectra of fluorophores easily overlap with each other and limit the capability for multiplex detections.

Electrochemical biosensors are recognized as a cost-effective sensor platform with high sensitivity, fast response and the capability for high-degree miniaturization and multiplex detection. Electrochemical detection of proteases has been demonstrated in both affinity and activity formats.

SUMMARY

Briefly, the present disclosure describes an electrochemical method based on a peptide-functionalized microelectrode array (MEA) for direct detection of enzymatic activity in a biological sample, which has the potential to analyze multiple protease activities simultaneously. More importantly, a heterogeneous Michaelis-Menten model was developed to fit the experimentally measured kinetic proteolytic curves and derive the fundamental kinetic constants. This algorithm enables determination of the effective activity of a target biomarker in addition to measurement of the concentration as reported in other electrochemical studies.

Recently, we have fabricated a 3×3 gold MEA and demonstrated its capability for multiplexed detection of cathepsin B activity using three specific peptide substrates functionalized on separate microelectrodes. Highly consistent proteolysis results have been obtained over 9 independent channels simultaneously. This physiology-compatible condition is attractive for directly measuring multiple extracellular proteases in HS without significantly alternating their intrinsic activities. By lowering the ionic strength in the buffer, a significantly higher cathepsin B activity was measured, leading to a more sensitive detection with the limit of detection (LOD) down to 57.1 pM, which is comparable to ELISA and is sufficient for measuring cathepsin B in diluted human serum. The electrochemical method was directly compared with the traditional affinity-based ELISA in measuring diluted HS and that spiked with cathepsin B. The results show that the electrochemical method can consistently measure cathepsin B activity based on the proteolytic kinetics. In contrast, ELISA mainly measures the inactive proenzyme and its signal is significantly suppressed in activated cathepsin B. These two techniques provide complementary information regarding the properties of cathepsin B in the complex HS, which is critical toward disease diagnosis based on detecting activity profiles of extracellular proteases.

In one aspect, the disclosure concerns microelectrode arrays for detecting target biomarkers. The arrays generally comprise an electrically conductive surface (microelectrode) having a plurality of short peptides extending therefrom, each peptide comprising a proximal end that is directly or indirectly attached to the surface and a distal end that is spaced apart from the surface. The "free" or distal end of the peptide comprises an electron reporter or redox moiety attached thereto. In one or more embodiments, the proximal end includes a linker (e.g., 5-aminopentanoyl amide moiety) for covalent conjugation to the surface and immobilization of the peptide thereon. Each of the peptides comprises a consensus sequence containing a scissile peptide bond that is susceptible to specific cleavage by a target protease biomarker, such as a protease overexpressed in cancer like cathepsin B. The array preferably comprises a plurality of individually addressable microelectrodes separated by insulating material, and each of the microelectrodes comprises a plurality of peptides extending therefrom. For example, for a microelectrode having a dimension of approx. 200×200 um, there can be from about $1\times10^8$ to $1\times10^{10}$ peptides attached to a single electrode surface (with each electrode preferably being functionalized with only one "type" of peptide). The array is configured to detect the activity of one or more protease target biomarkers present within a biological sample through cleavage of the consensus peptide sequence by a target protease biomarker, if present, which releases the redox moiety effecting a detectable change in an electrical current across said array over time. Analysis of this change (experimentally measured kinetic proteolytic curves) using the heterogeneous Michaelis-Menten model described herein allows one to derive the fundamental kinetic constants (or the cleavage reaction rate) and correlate the results to the activity of the target protease biomarker.

The disclosure also concerns electronic chips 12 as depicted in FIG. 1, comprising a microelectrode array 14 according to the various embodiments described herein, further comprising contact pads 18, each contact pad being connected to a respective electrode 20 via a respective conductive lead 16 on the chip 12.

Also described and exemplified herein are systems for electrochemical detection of target protease biomarkers. The systems generally comprise an electronic chip according to the various embodiments described herein. The chip is positioned within an electrochemical cell, and the electrochemical cell is electrically connected via a breakout box to a potentiostat for interrogating and measuring via AC voltammetry the signal over time before, during, and after contacting the array with a biological sample containing or suspected of containing a target biomarker.

The present disclosure also concerns methods of detecting a protease biomarker within a biological sample. The methods generally comprise contacting a microelectrode array according to the various embodiments described herein with a biological sample containing or suspected of containing one or more protease biomarkers and detecting changes in the electrical current across the array over time (e.g., using AC voltammetry).

BRIEF DESCRIPTION OF THE DRAWINGS

FIG. 12 shows the reaction scheme for synthesis of peptide H-15 and peptide H-16 with attached Fc moieties.

Figure 19:
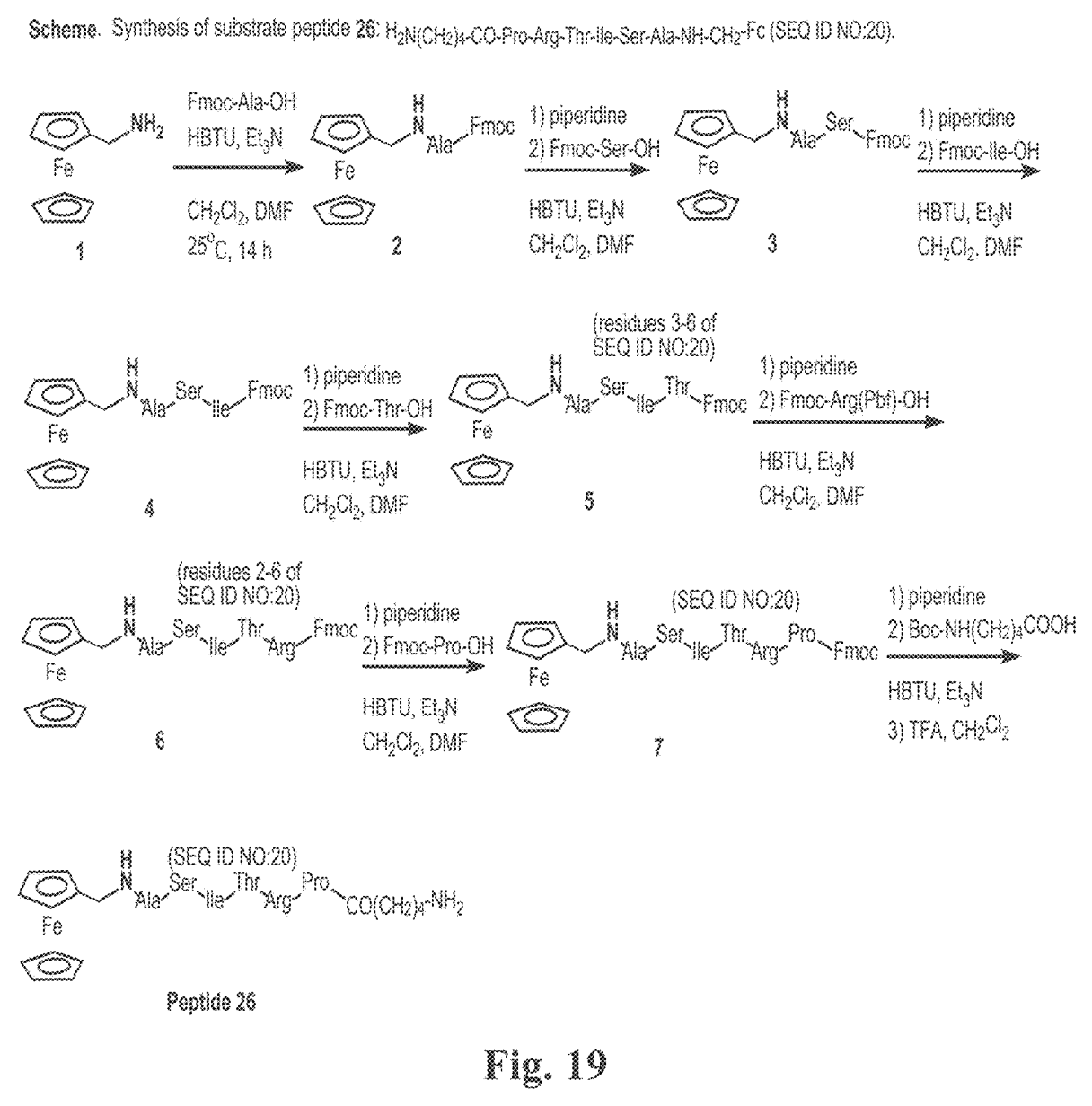

FIG. 19 shows the reaction scheme of synthesis of substrate peptides using peptide 26 as example.

FIG. 22 shows (A) Representative normalized kinetic proteolysis curves and the fitting lines for Au MEA modified with peptide-Fc substrate at activated rhCB concentrations of 0, 0.3, 1.0 and 6.0 nM in 0.5×PB (pH=7.4). (B) The scatter plot of 1/τ vs. rhCB concentration. The error bars are the standard deviation of 8 replicates at each concentration. (C) Linear calibration curve of cathepsin B protease activity in the activated rhCB concentrations from 0 to 1.0 nM.

Figure 23:
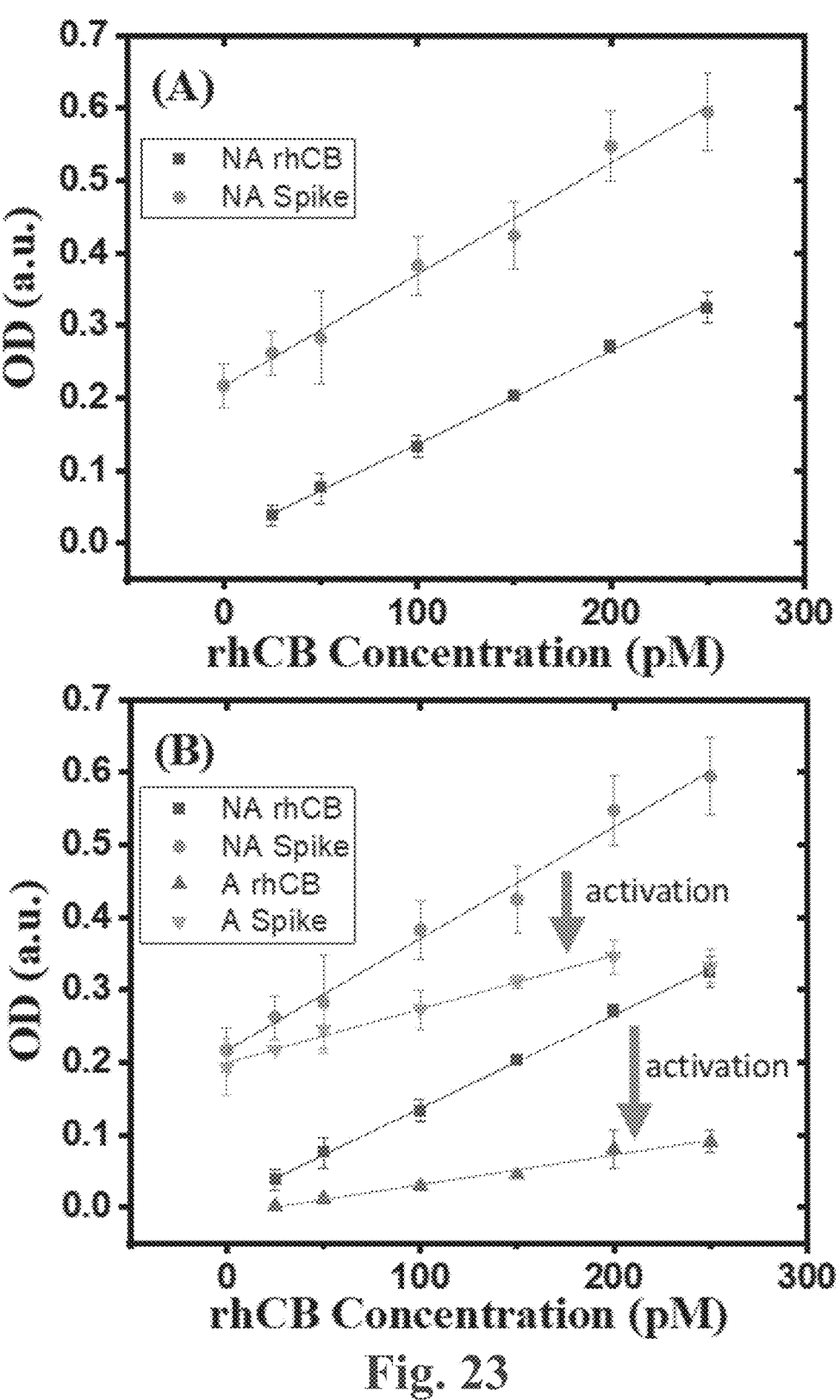

FIG. 23 shows calibration curves derived from ELISA measurements. (A) The OD readings of the developed product generated by varied concentrations of non-activated rhCB in 0.5×PB (■) and spiking the non-activated rhCB into 2.5% HS in 0.5×PB (●). (B) Addition of two sets of activation results to panel (A), i.e., activated rhCB in 0.5×PB (▲) and spiking the activated rhCB into the activated 2.5% HS in 0.5×PB (▼).

Figure 24:
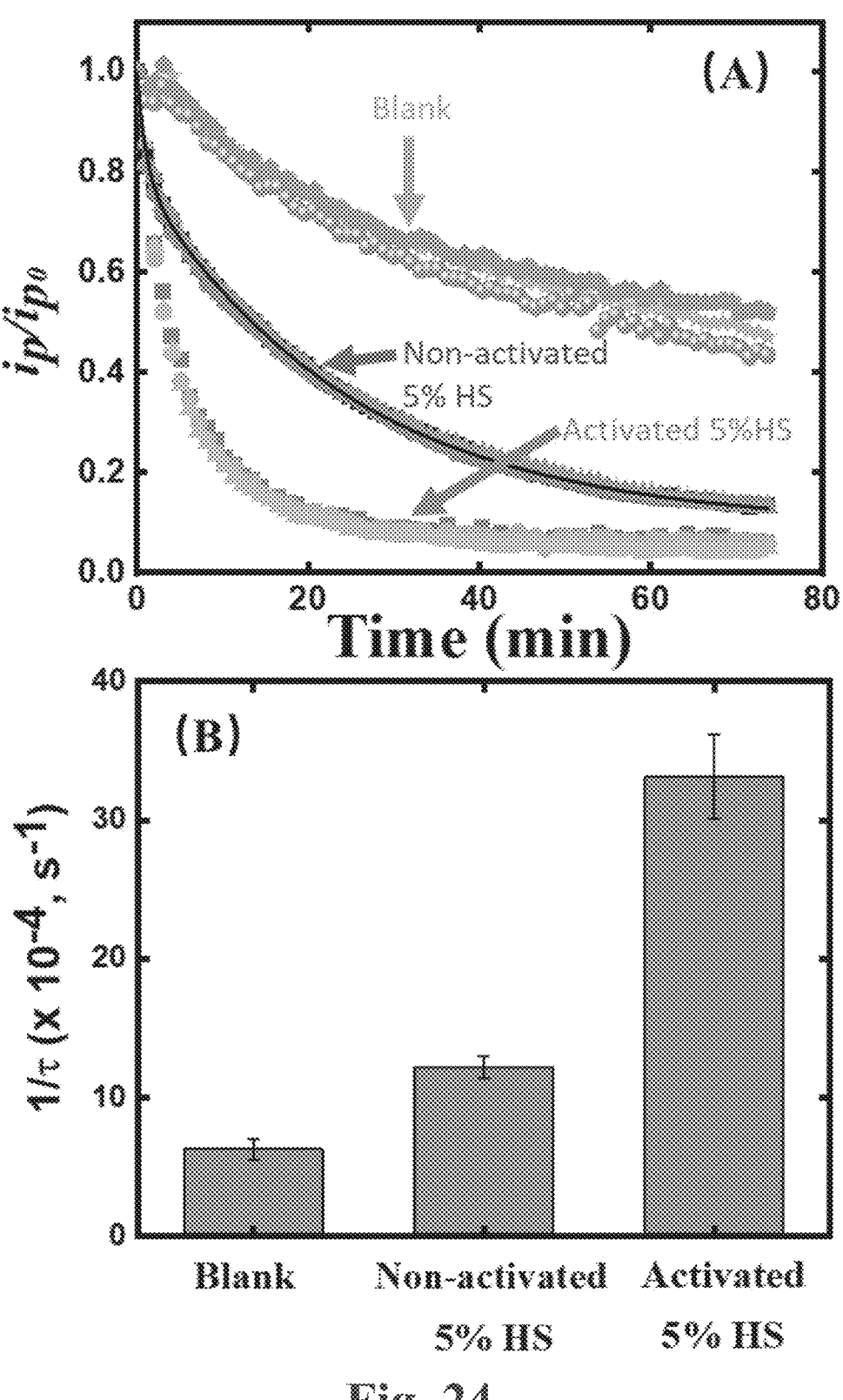

FIG. 24 shows (A) Representative normalized kinetic proteolysis curves and fitting lines (3 for each experiment) for peptide-Fc modified Au MEAs by activated and non-activated 5% HS in 0.5×PB. (B) Bar chart plot of 1/τ vs. different samples (blank, activated and non-activated 5% HS). The error bars represent the standard deviation from eight replicates (n=8).

Figure 25:
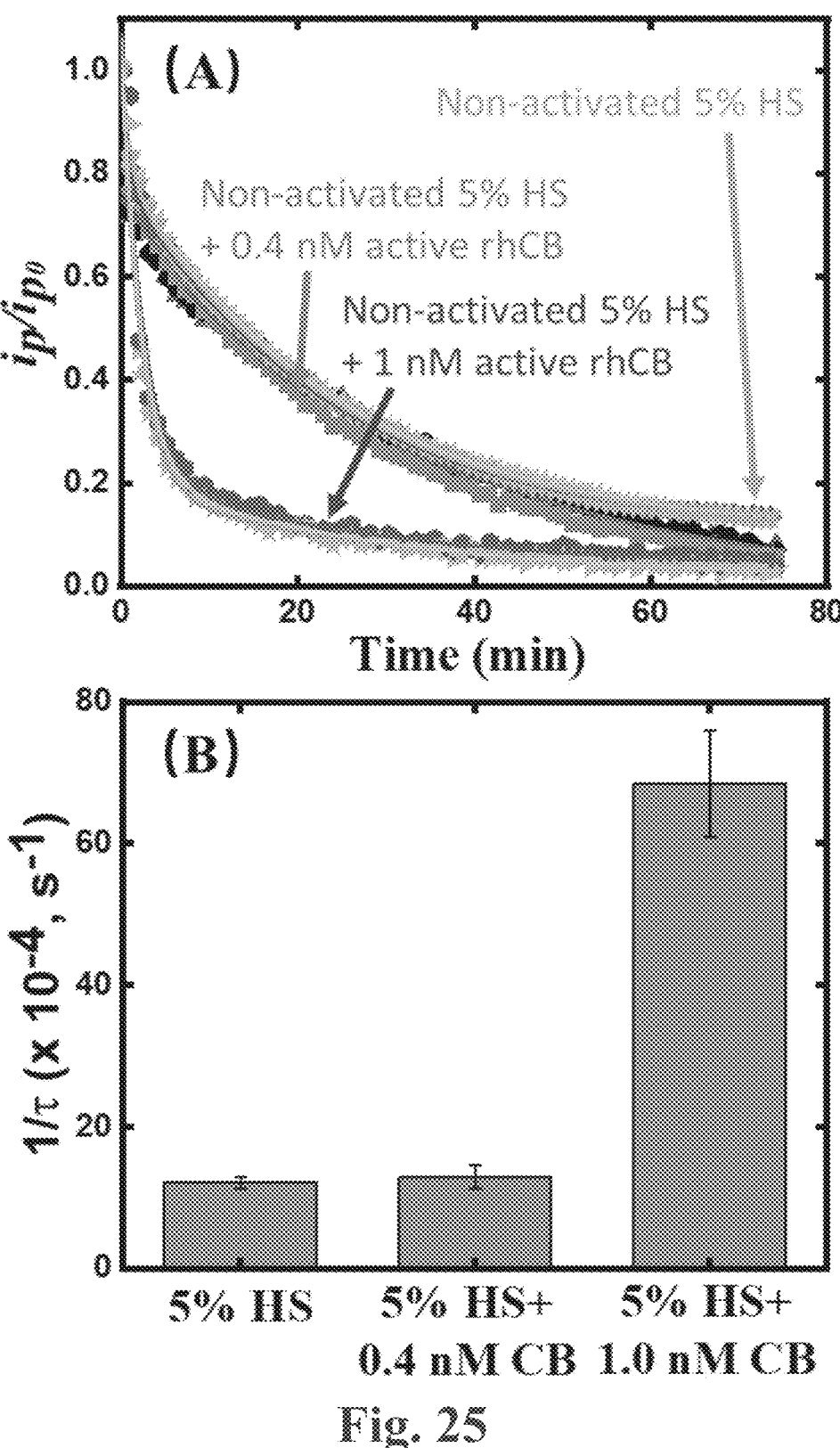

FIG. 25 shows (A) The representative normalized kinetic proteolysis curves and fitting lines for peptide-Fc modified Au MEA by non-activated 5% HS, and those spiked with 0.4 nM and 1.0 nM active cathepsin B, respectively. (B) Bar chart plot of 1/τ in the three samples. The error bars represent the standard deviation from eight replicates (n=8).

Figure 26:
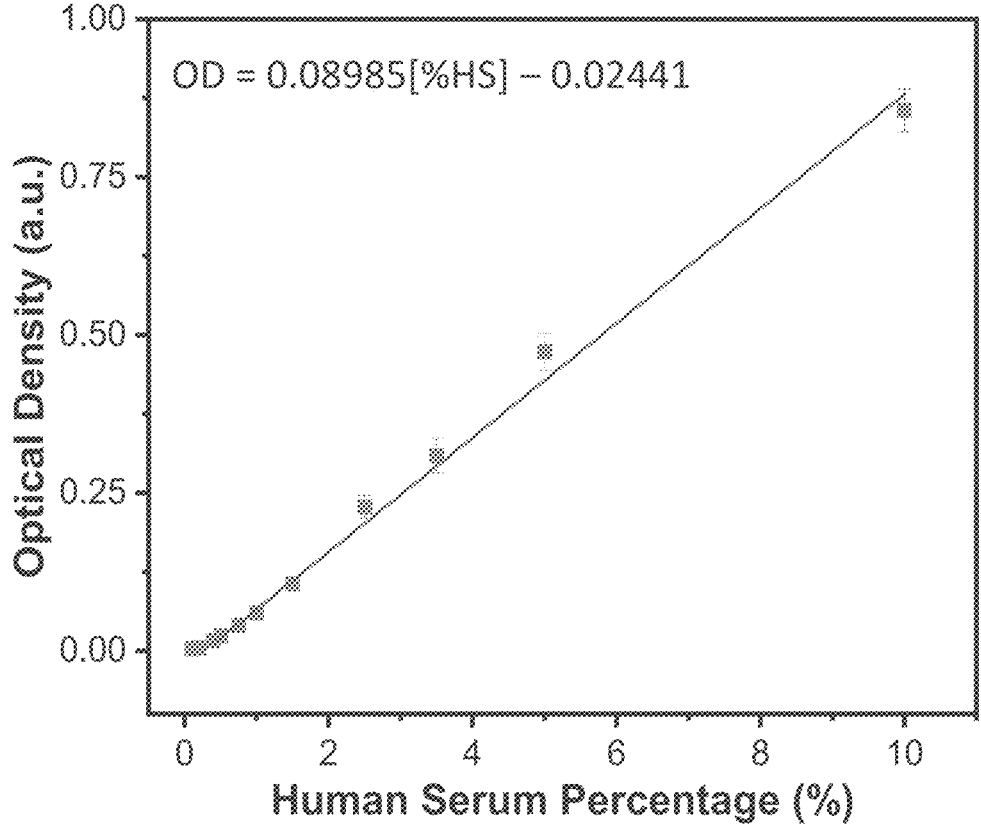

FIG. 26 shows the OD readings in ELISA measurements of a series of HS diluted with 0.5×PB containing 1% BSA. Even though all data points can be reasonably fitted with a linear line, the point above 5% HS starts to drop below the line by other points.

Figure 27:
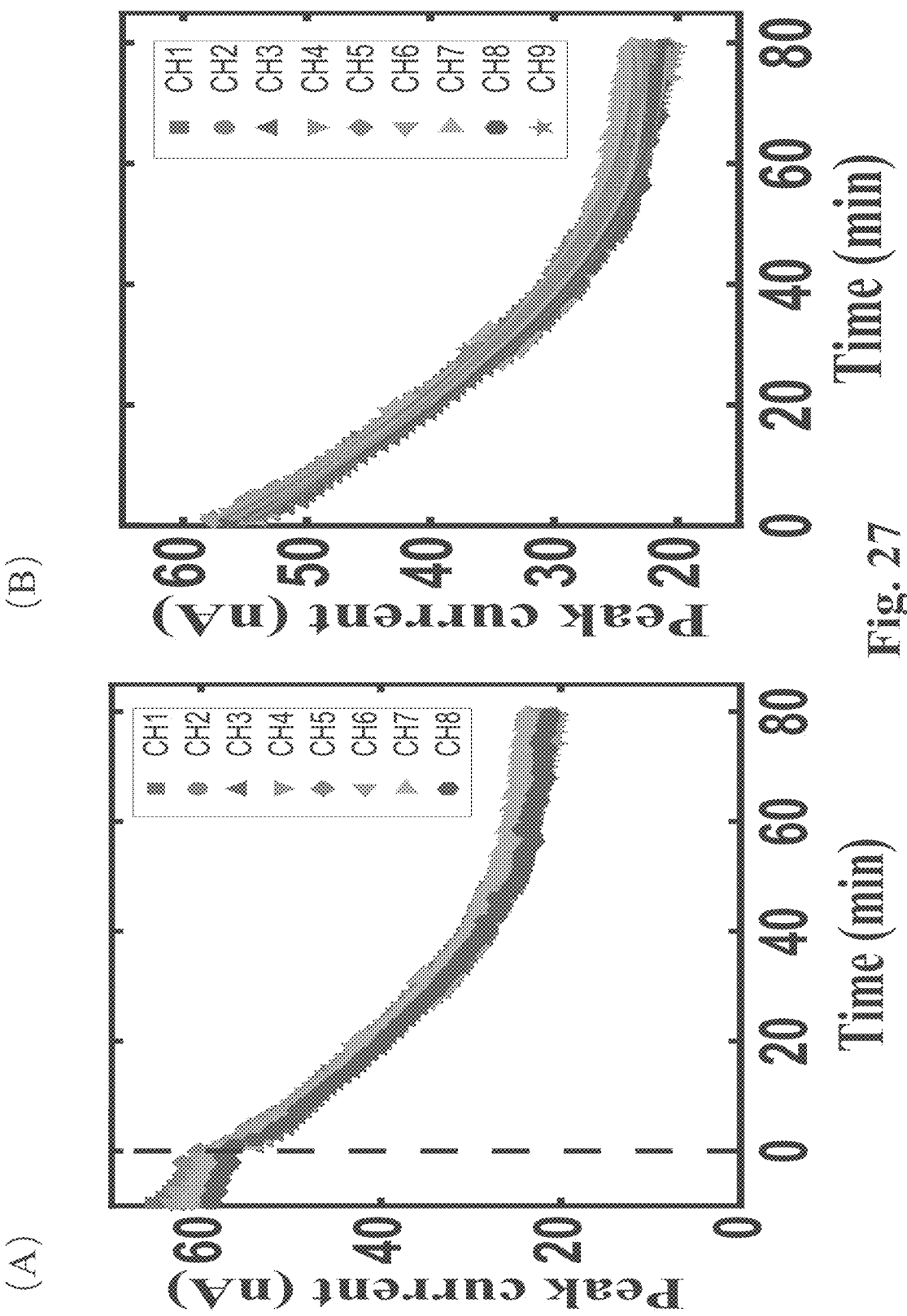

FIG. 27 shows (A) Kinetic proteolysis curves of an Au MEA modified with peptide-Fc substrate, H-15, by 1.0 nM cathepsin B in the 25 mM MES buffer (pH=5.0). (B) The fitting curves to the extracted proteolysis portion.

Figure 28:
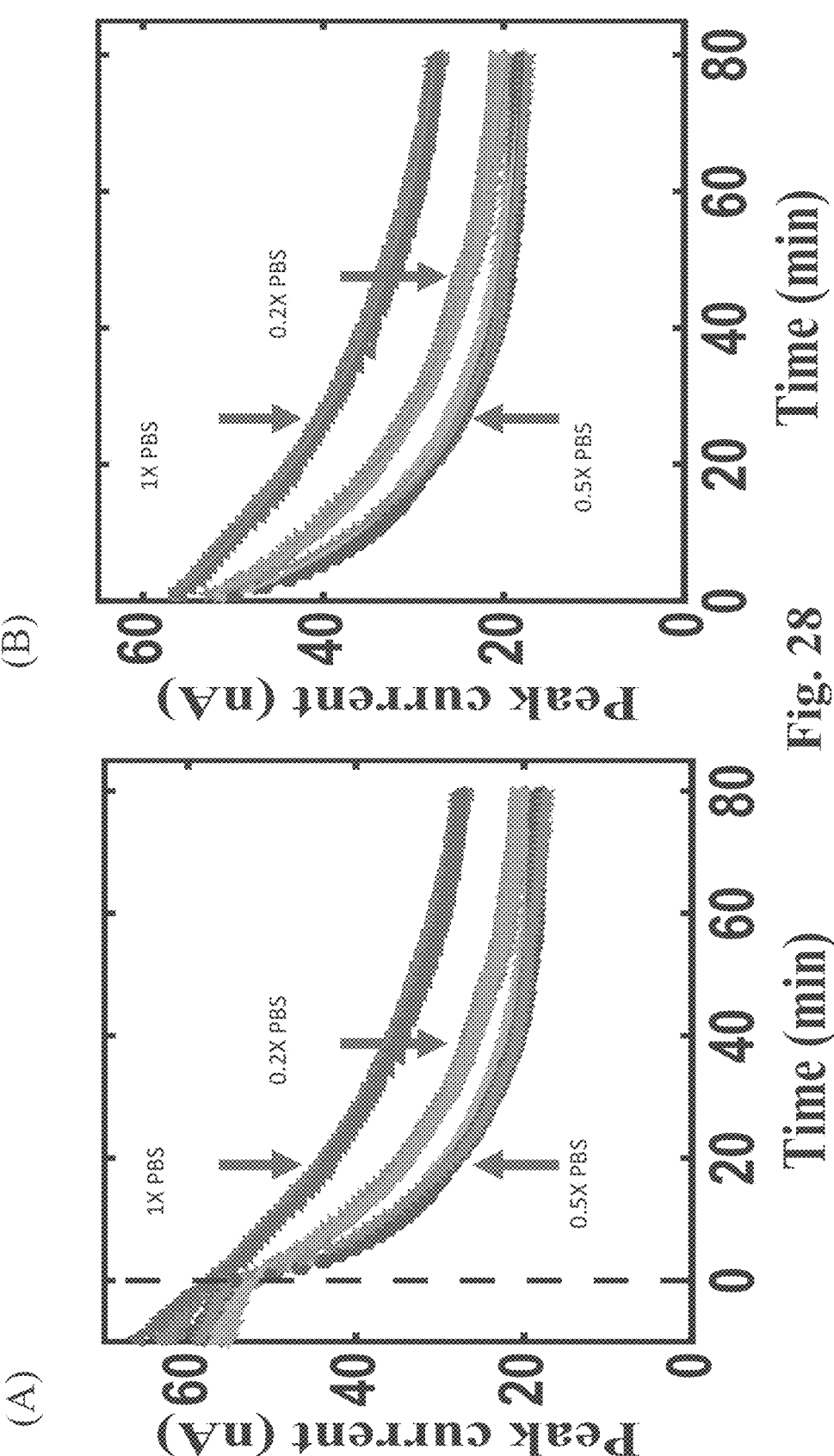

FIG. 28 shows (A) Kinetic proteolysis curves of an Au MEA modified with the peptide-Fc substrate, H-15, by 1.0 nM cathepsin B in 1×, 0.5× and 0.2×PBS buffer (pH=7.4). (B) The fitting curves to the extracted proteolysis portion. For clarity, only three proteolysis curves are shown at each buffer concentration.

Figure 29:
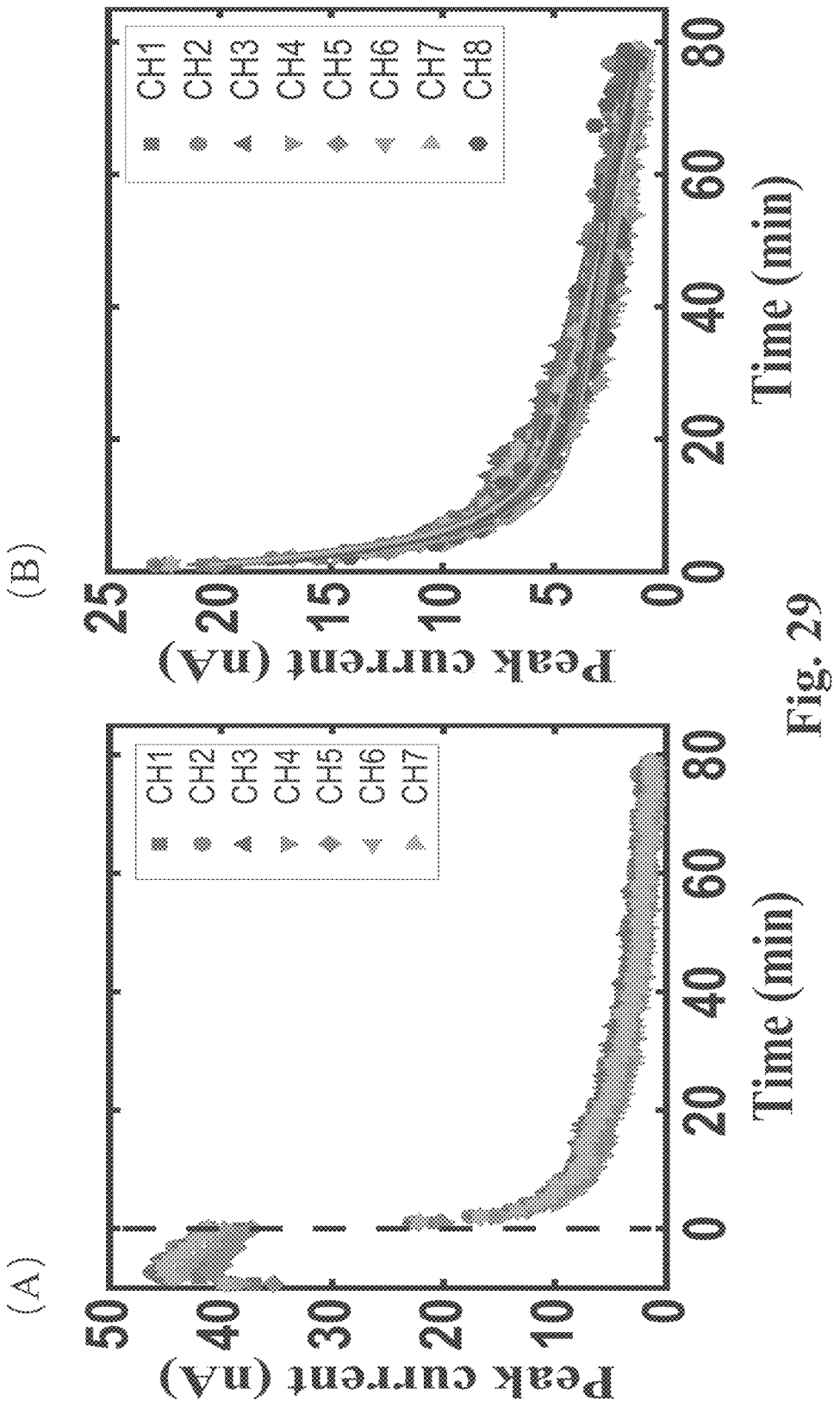

FIG. 29 shows (A) Kinetic proteolysis curves of an Au MEA modified with peptide-Fc substrate, H-15, by 1.0 nM cathepsin B in 0.5×PB buffer (pH=7.4). (B) The fitting curves to the extracted proteolysis portion.

Figure 30:
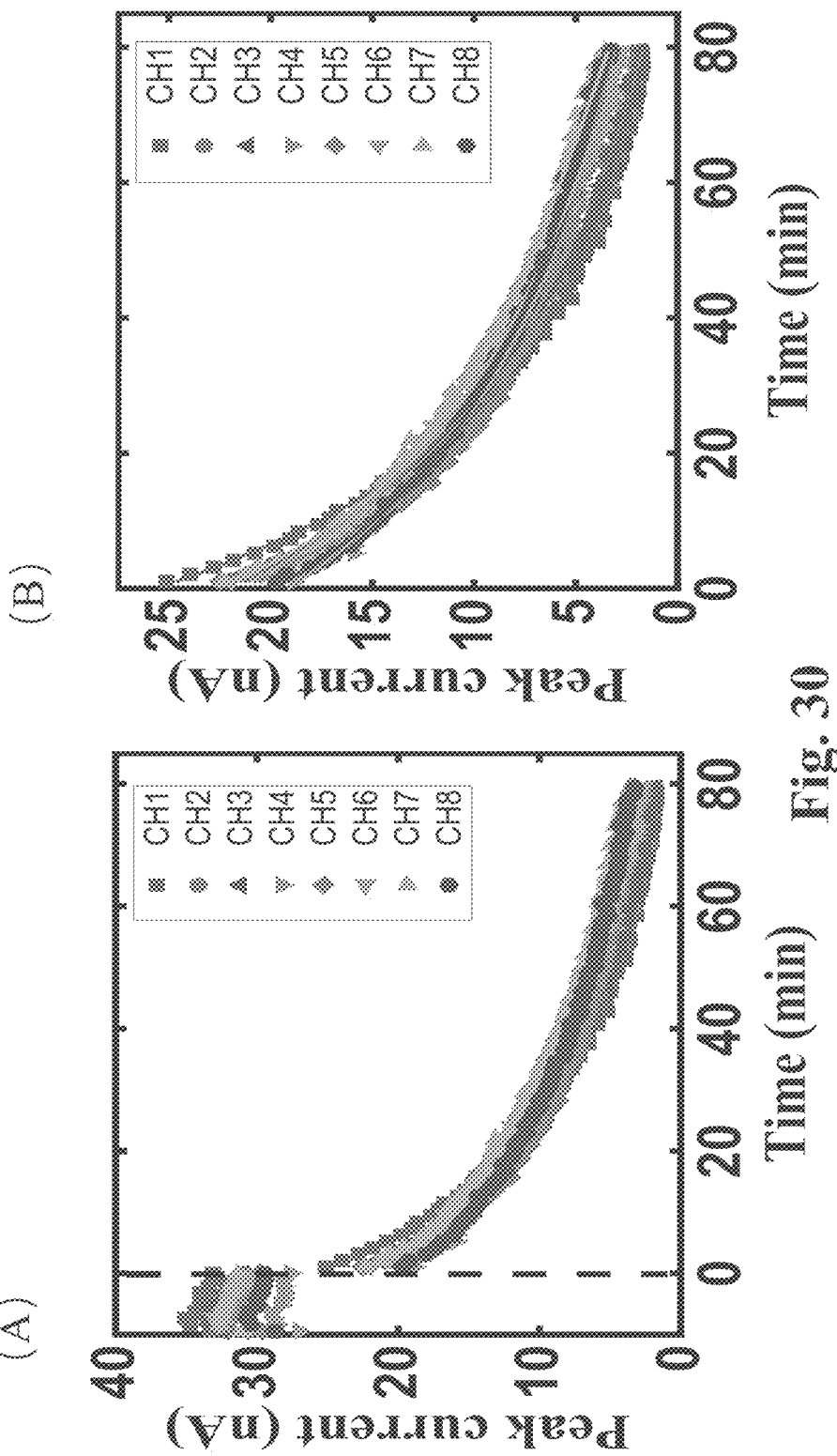

FIG. 30 shows (A) Kinetic proteolysis curves of peptide-Fc modified Au MEA by 5% HS in 0.5×PB buffer (pH=7.4). (B) The extracted proteolysis curves and corresponding fitting lines.

Figure 31:
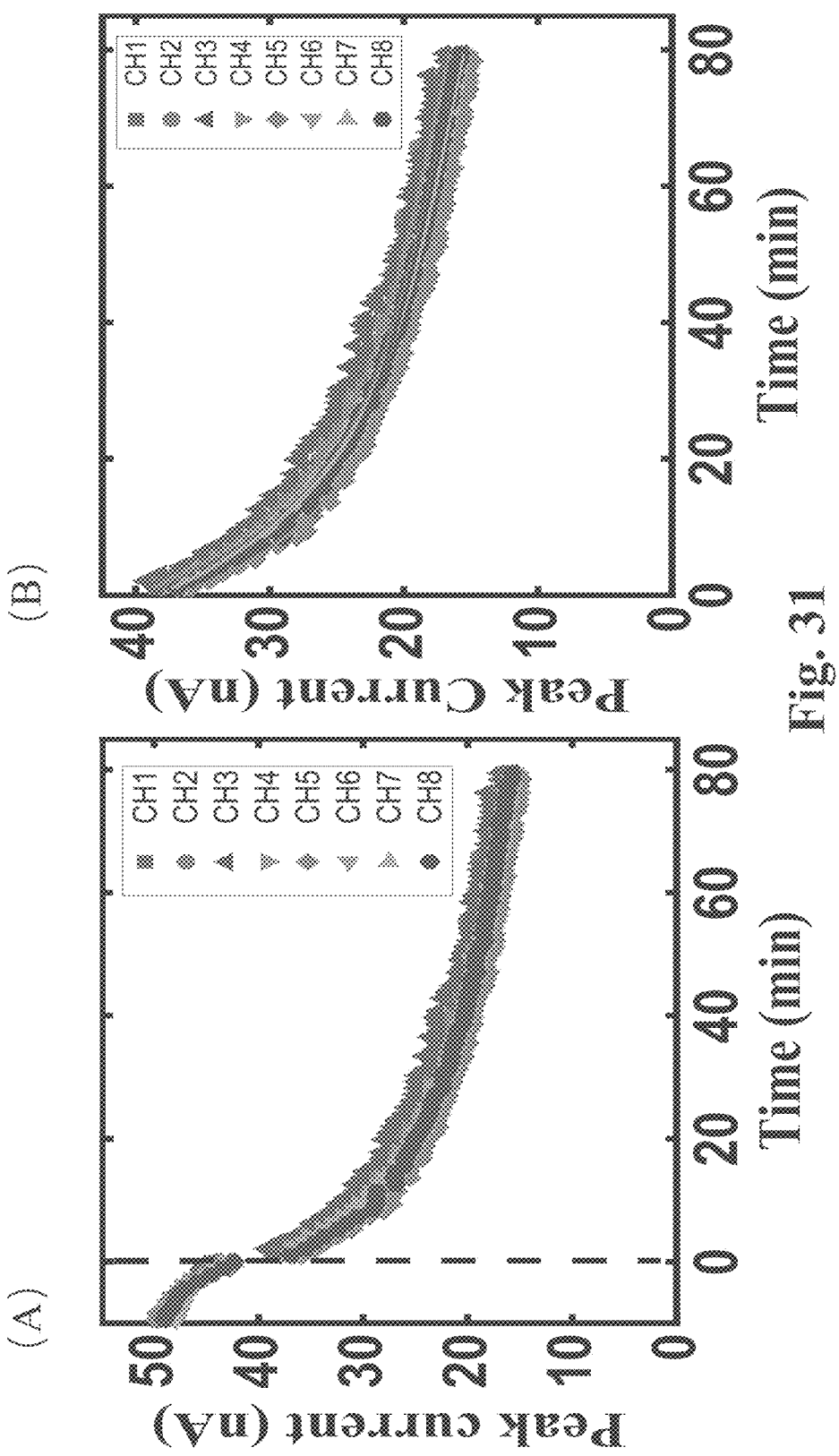

FIG. 31 shows (A) Kinetic proteolysis curves of peptide-Fc modified Au MEA by 5% HS in 0.5×PB buffer (pH=7.4) spiked with 1.0 nM cathepsin B (containing 0.40 nM active form). (B) The extracted proteolysis curves and corresponding fitting lines.

Figure 32:
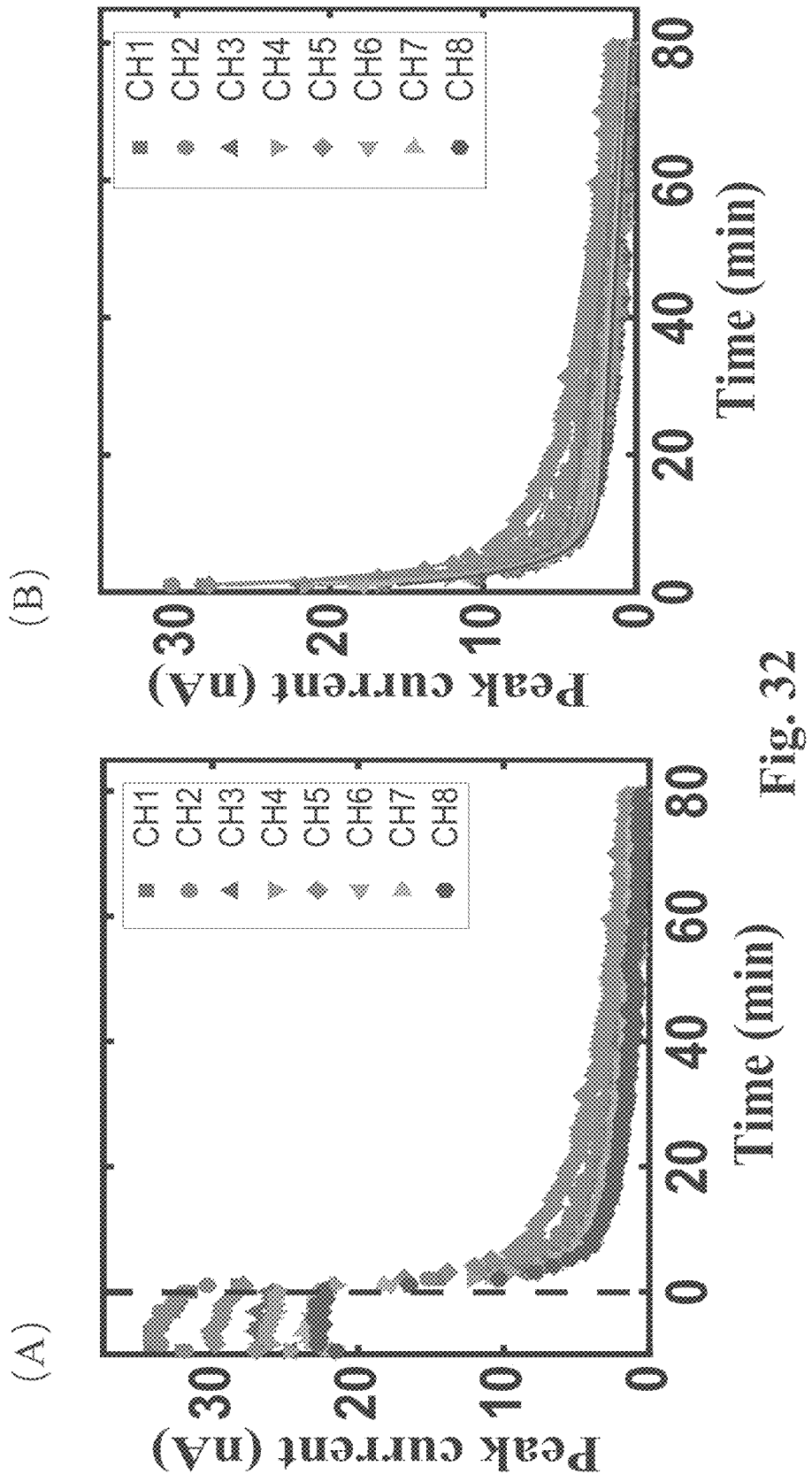

FIG. 32 shows (A) Kinetic proteolysis curves of peptide-Fc modified Au MEA by 5% HS in 0.5×PB buffer (pH=7.4) spiked with 1.0 nM active cathepsin B. (B) The extracted proteolysis curves and corresponding fitting lines.

Figure 33:
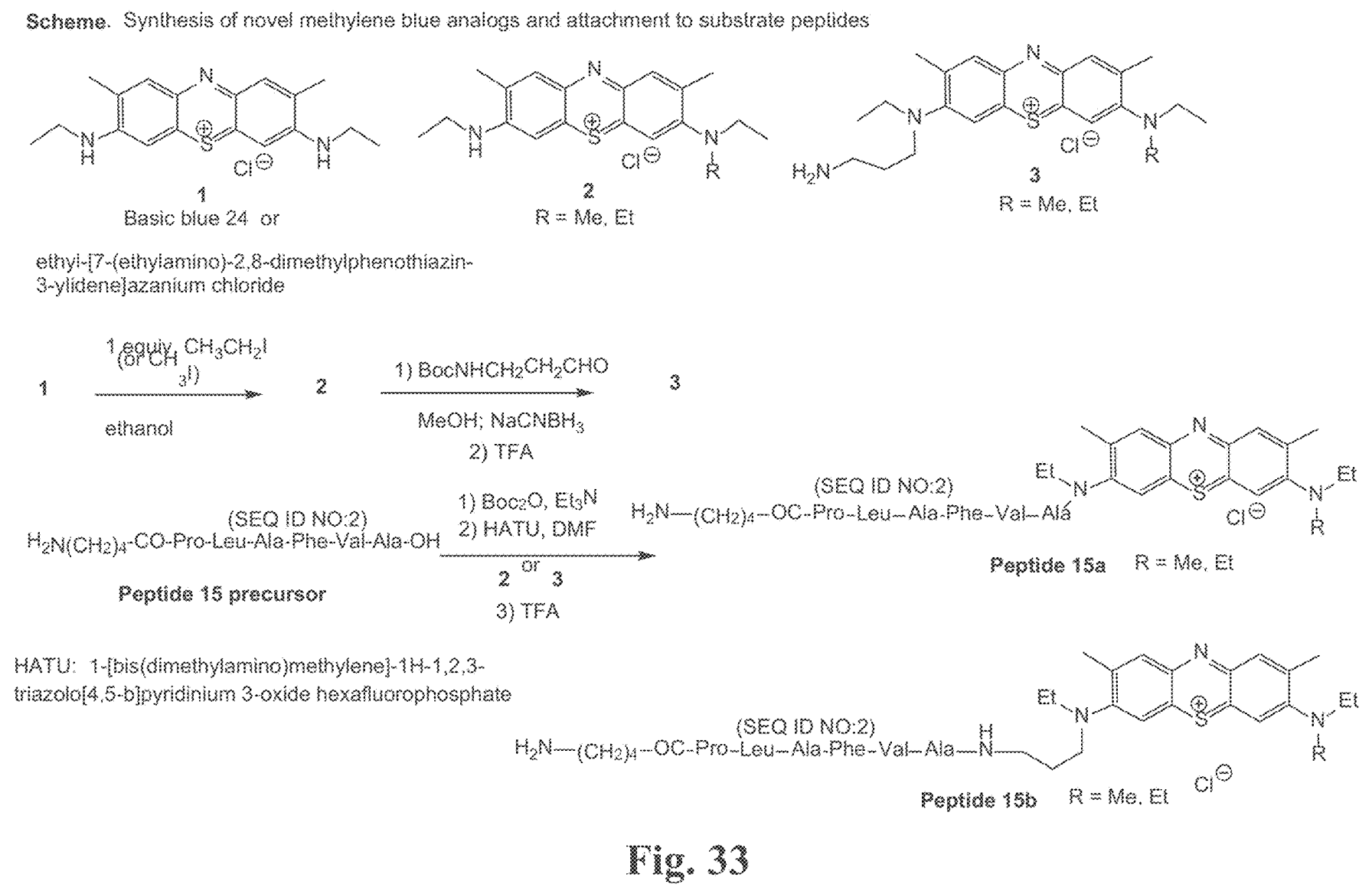

FIG. 33 shows the synthesis of novel methylene blue analogs for redox reporter moieties and attachment to substrate peptides.

DETAILED DESCRIPTION

A multiplex electrochemical sensor for the detection of protease biomarkers, and particularly activity of protease biomarkers, has been developed. The sensor is fabricated on the wafer-scale using traditional lithographic cleanroom processes and in the exemplary embodiment contains a 3×3 microelectrode array (MEA). After chemical modification, the sensor is capable of selectively detecting target protease biomarkers and quantifying their activities, which can be used for advanced diagnosis of medical conditions including skeletal muscle atrophy, Alzheimer's disease, and many types of cancers.

Proteases are enzymes responsible for breaking down proteins. Consequently, proteases are involved in many biological processes and the rate of proteolytic reactions are often indicative of physiological misfunctions such as those caused by skeletal muscle atrophy, cancers and other conditions relevant to long term space habitation (i.e., microgravity, cosmic radiation, etc.). Current methods for detecting protease activity require significant sample processing.

Figure 1:
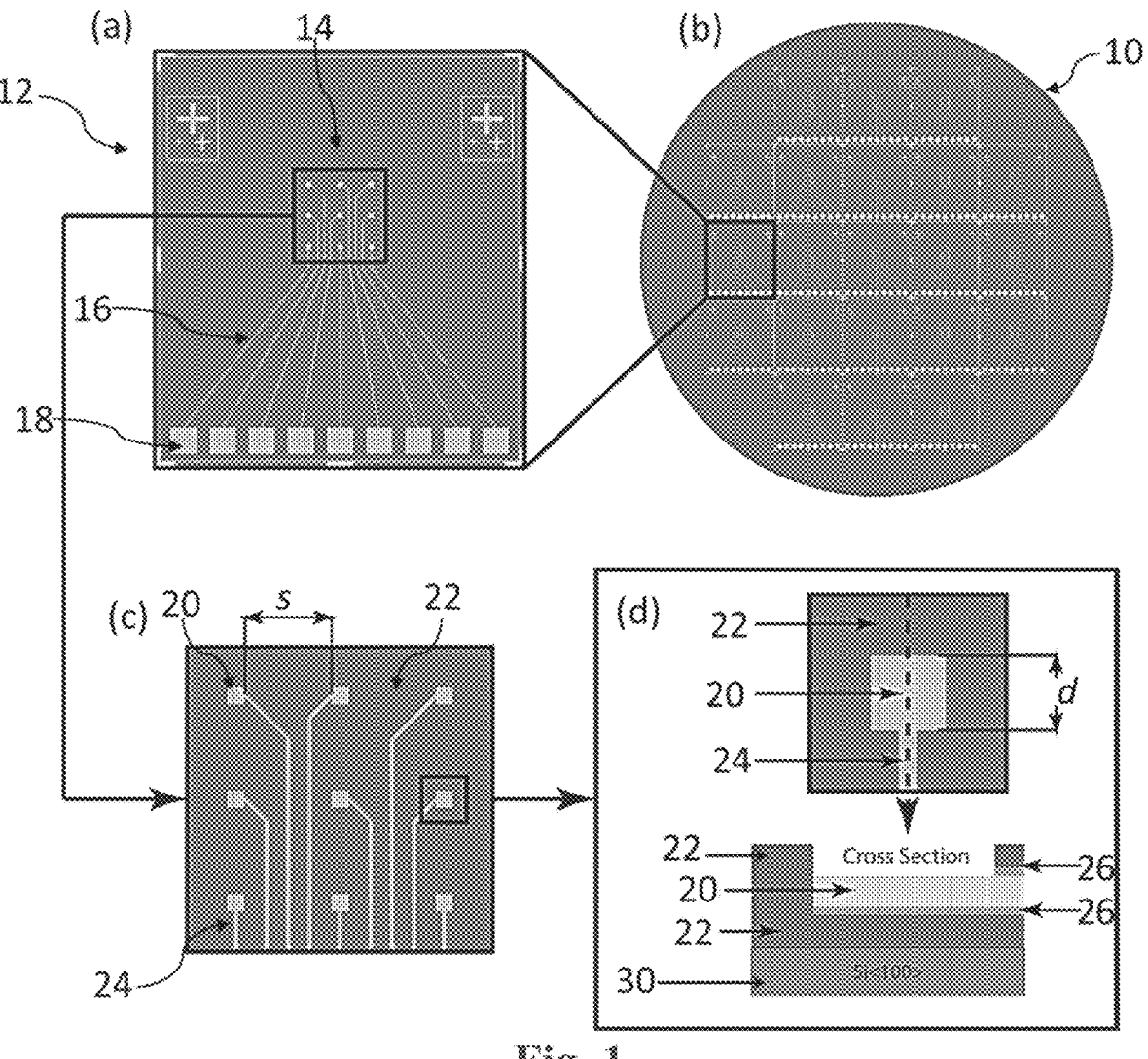
FIG. 1 is a schematic diagram of the (a) wafer onto which multiple chips can be fabricated; (b) a close-up view of an individual chip; (c) a close-up view of an individual 9-electrode array; and (d) a close-up view of the top of an individual electrode and cross-section view of the same electrode, including the embedded lead.

The electrochemical sensor chip consists of layers of silicon dioxide, titanium and gold patterned onto silicon, which can advantageously be created using traditional, wafer-scale microfabrication protocols on a wafer 10. In an exemplary embodiment, as shown in FIG. 1, each chip 12 is patterned with an array 14 of a plurality of individually addressable gold microelectrodes 20 and each of the microelectrodes 20 can be chemically modified with custom-synthesized peptide sequences (the probe) that can specifically detect one or more protease biomarkers. Measurements are made with external equipment (a potentiostat) connected to a custom-built electrochemical cell consisting of a counter electrode and a reference electrode. When a sample is introduced to the MEA, the change in signal is monitored simultaneously on all the electrodes over time and the signal corresponds to the activity of the target protease biomarker associated with the specific peptide probes functionalized on each specific microelectrode. The activities of the target proteases can be derived from the measured kinetic signal and can be used to make advanced diagnosis of several health conditions.

The electrochemical biosensor platform based on multiplex micro-/nano-electrode arrays can be applied toward cancer diagnosis based on rapid profiling of biomarker activities, such as proteases. Quantitative detection of the activity profile of specific target proteases is in high demand for the diagnosis and treatment monitoring of diseases such as cancers. The biosensor platform can also be used for biosensors for monitoring astronaut health regarding cardiovascular disease, muscle atrophy, and bone density loss based upon protease activity profiling, during long-duration space flights.

Figures 2, 3:
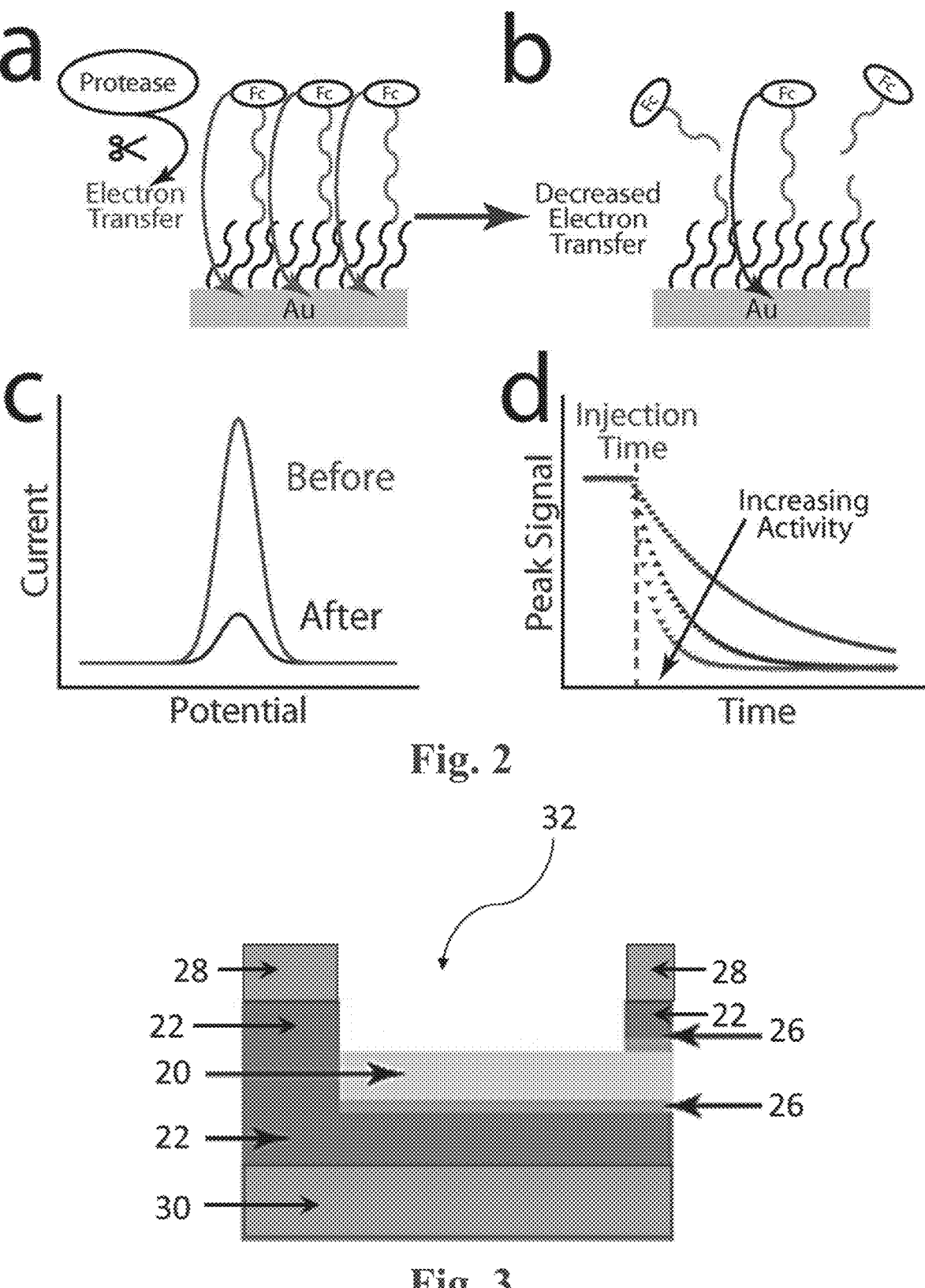
FIG. 2 is a is a cartoon illustration of the proteolysis process (a)-(b) resulting in a decrease of electrical current on the microelectrode surface and corresponding ways to measure this using AC voltammetry, (c) including the AC voltammetry signal before and after proteolysis and (d) the kinetic proteolytic curves, i.e., the exponential peak current decay over time.
FIG. 3 is an enlarged cross section view of a microelectrode with a polymer coating with openings to form microwells for testing samples.

The array is capable of detecting the presence of one or more proteases present within a biological sample (preferably two or more, more preferably three, four, five, six, seven, or eight or more, etc. and in some cases up to nine different proteases or more present in the sample), depending upon the number of electrodes configured in the array. As illustrated in FIG. 2, in particular embodiments, the electrode arrays comprise one or more redox reporter moiety-attached short substrate peptides (peptide probes), covalently linked to the electrode surface. When contacted with a sample containing (or suspected of containing) one or more target proteases, the proteases, if present, continuously cleave the attached substrate peptides, releasing the redox moiety containing fragment from the electrode surface, which causes a detectable decrease in the electrical signal (current) of the array over time as measured by AC voltammetry. The inverse of the exponential decay time constant indicates the activity of the protease, which can be analyzed using a surface-based heterogeneous Michaelis-Menten model.

In more detail, peptides with specific sequences designed and synthesized containing consensus sequences for selective proteolysis by the target proteases. These peptides are attached to the electrode surface as the specific probes. The distal end is covalently attached with a redox moiety for electrochemical measurements. Ferrocene (Fc) group is an exemplary redox moiety depicted in FIG. 2. The quantity of the intact peptides on the electrode surface can be sensitively detected with an AC voltammetry method and initially presents as the peak current at the specific potential for Fc oxidation into ferrocenium (Fc$^+$). As the peptide is cleaved by the cognate protease, the peak current decreases exponentially in the continuously repeated AC voltammetry measurements.

The recorded kinetic proteolytic curve can be quantitatively described by a surface-based heterogeneous Michaelis-Menten model. The inverse of exponential decay time constant, $1/\tau$, is found to represent the protease activity which equals to $[E](k_{cat}/K_M)$, where $[E]$ is the protease concentration and $k_{cat}/K_M$ is the specificity constant defined by the kinetic proteolytic reaction constant $k_{cat}$ and the Michaelis equilibrium constant $K_M$. The value of $k_{cat}/K_M$ depends on the substrate peptide sequence, peptide length, temperature and buffer composition. Highly sensitive detection of the protease activities including cathepsin B, a cancer biomarker, can be obtained at the conditions giving the high $k_{cat}/K_M$ value.

The individual gold microelectrodes in the exemplary embodiments are partially buried underneath the surrounding SiO$_2$ thin film, which show highly consistent cyclic voltammetric signals in gold surface cleaning experiments and detecting benchmark redox species in solution. It will be appreciated that upon selectively functionalizing each of the individual gold microelectrodes with the specific ferrocene-labeled peptide probes, simultaneous detection of the proteolytic curves of one or more target proteases can be obtained over multiple channels by monitoring the decay of the AC voltammetry signals of the ferrocene-labeled peptide probe molecules over time. The activity of the proteases including cathepsin B has been derived by fitting the kinetic proteolytic curves. Simultaneous detection of the proteolysis of cathepsin B on the MEA functionalized with three different hexapeptides has been demonstrated, showing the potential of this sensor platform for rapid detection of the activity profiles of multiple proteases.

Advantageously, the above-discussed electrochemical method detects the activity of the protease biomarker, and thus detects the level of the active form of the protease biomarkers, which reflects a more accurate biological function of the proteases in the patient sample, and is fundamentally different from the detection of the total concentrations (including both active and inactive forms) of the proteases as derived from commonly used affinity biosensors or assays such as enzyme-linked immunosorbent assay (ELISA). For example, the direct comparison has shown that ELISA measurements will give the same results no matter the original proenzyme form (zymogen) in the sample is active (activated) or not, while the electrochemically measured activity shows dramatic increase after being chemically activated. Moreover, in contrast to the current activity-based assays, each protease is measured separately in its optimal buffer having a pH value varying from 5 to 9. It is not possible to measure multiple proteases in a common buffer simultaneously. The present work demonstrates a modified buffer system in which the electrochemical method can be applied for protease activity profiling in a buffer at pH=7.4 that is compatible to the physiology conditions. This enables measuring the activity of multiple proteases directly in human serum, with minimal or no sample preparation, which is a critical step toward protease activity for cancer diagnosis.

In one or more embodiments, the disclosure concerns an electronic chip comprising a plurality of the electrode arrays as described herein. In particular embodiments, the electronic chip is useful for detecting specific biomarkers, such as proteases or other enzymes which can cleave a target substrate sequence, the presence of which are biomarkers of various cancers such as breast, lung and liver cancer, and other diseases such as Alzheimer's disease and various viral infections. Thus, the electrode arrays and electronic chips comprised of the arrays can be applied for rapid screening tests and monitoring of treatment response. In addition, the electronic chips may comprise a nanoelectrode array configured to detect a plurality of different enzymes within a biological sample.

According to still other aspects, there is provided a method of detecting a biomarker within a biological sample comprising contacting one or more electrode arrays with a biological sample containing or suspected of containing one or more biomarkers as described herein. In a particular embodiment, the method comprises detecting the presence of cancer in an animal or human by detection of overexpressed proteases. Certain methods according to the present are directed toward an electrochemical method for measuring the activity of proteases using electrode arrays fabricated with gold electrodes. In one or more embodiments, a plurality of individually addressed electrode arrays is provided on an electronic chip. The nanoelectrode arrays contained on the chip may be configured to detect a plurality of different biomarkers. Upon contact with a biological sample containing one or more target proteases or enzymes, the cleavage of a peptide or peptide residue attached to the electrode surface comprising the array results in a reduction in the redox signal of the redox reporter moiety attached to the substrate peptide or peptide probe. This reduction in redox signal is measured with AC voltammetry.

In one or more embodiments, this electrochemical platform can specifically detect down to subnanomolar concentrations of enzymes, such as legumain, cathepsin B, MMP-7, and MMP-9, within a biological sample. Moreover, in further embodiments, non-specific binding is not a concern and false positive results are minimized by specific proteolytic rates and pattern profiling of each target enzyme (particularly proteases) using a library of enzyme substrates. The MEAs are useful with established specific biomarkers as an electronic method for rapid profiling of the activities of cancer-related proteases. Depending upon the detected biomarkers or combinations of biomarkers, various diagnosis or recommendations for follow-up testing can be made. The relevance, or lack thereof, of various possible biomarkers (or combinations) can be derived from literature reports.

The MEAs can be used for multiplex detection in two ways. First, the MEAs in the depicted 3×3 arrays can be used to screen peptide candidates for a specific protease. Peptide candidates (up to nine) with different amino acid sequences can be functionalized separately on respective microelectrodes and the proteolysis kinetics by a specific protease target in the applied solution can be measured simultaneously. These measurements allow selection of the peptide sequence exhibiting the highest proteolytic activity by its protease target. Multiple peptides exhibiting the highest activity (the highest cleavage rate) among the nine candidates can be screened out as the highly selective peptide substrates to be used for detecting this particular protease target in the second approach. Second, the MEAs can be used for detection of two or more protease enzymes simultaneously in the sample. In the depicted 3×3 arrays, the MEAs can be used to potentially detect up to 3 different enzyme combinations in a single microfluidics sample. Three microelectrodes are functionalized with 1 to 3 types of aforementioned peptide substrates that are highly selective to one of the three protease targets and the proteolysis by the mixture of the three proteases are measured over the nine peptide-functionalized microelectrode simultaneous. The MEAs can be used to provide a protease activity profile of a given cancer from a particular patient (a personalized profile), allowing not just the detection of cancer but monitoring cancer progression by testing samples from the patients before, during, and after treatment to monitor the efficacy of the treatment based upon protease activity changes (or lack thereof) over time.

Because the sensor platform can detect and quantify protease activity, the MEAs can also be used to screen protease inhibitors as drug candidates for treatment of diseases (such as cancer, cardiovascular disease, Alzheimer diseases, etc.) or suppress the coronavirus production and transcription. In such an embodiment, a sample with a known protease content can be mixed with a candidate inhibitor compound and then contacted with the MWA. The activity of the protease can be detected and quantified and correlated with the effectiveness (or lack thereof) of the candidate in inhibiting protease activity.

The electrode arrays can be fabricated using traditional lithography and Si wafer patterning techniques. In one or more embodiments, the electrode is fabricated from known electrode materials such as, for example, gold (Au), titanium (Ti), silver, platinum, carbon, or silicon. For example, a Si wafer substrate 30 can first be thermally oxidized to yield a silicon dioxide layer 22 on the wafer surface as illustrated in FIG. 1. The wafer 30 can then be coated with alternating thin film layers of metal, such as titanium adhesion layers 26 and an electrically conductive gold layer 20, e.g., by using electron beam evaporation. At least one metal layer is an electrically conductive layer, preferably gold. The metal surface can then be coated with a suitable photosensitive resin (e.g., photoresist). In the examples, a positive photoresist is used, and then exposed to radiation through a photomask having a pattern that corresponds to the desired array pattern to be ultimately formed (not shown). The wafer is then washed with developer solution to remove the portions of the photoresist that are degraded by photoexposure and yielding a patterned photoresist layer, having open areas where the underlying Au/Ti layer is exposed and other areas where the photoresist layer covers the Au/Ti layer. The open areas are then etched to remove the desired portions of the Au/Ti layer, underlying Au layer, and underlying Ti layer, and leaving behind the array 14 design with contact pads 18, leads 16, and micro-electrode surface 20 protected under the photoresist layer. The photoresist can then be removed, and an insulating layer 22 (e.g., $SiO_2$) can be applied across the wafer. Other insulative materials include any dielectric material such as $Si_3N_4$, and $Al_2O_3$, or polymer such as epoxy, poly(methyl 2-methylpropenoate) (PMMA) and poly(p-xylylene) (parylene), can be alternatively used. The insulative material may be deposited using a chemical vapor deposition (CVD) method from, for example, vapor-phase precursor tetraethyl orthosilicate (TEOS), or vacuum vapor deposition for parylene, or solution casting for epoxy. It will be appreciated that the process could also be carried out using a negative photoresist and correspondingly patterned photomask if desired and apply photo exposure and photoresist development before metal deposition to form the patterned circuits.

A second photoresist is then applied on top of the insulating layer, which is then patterned by photoexposure as described above such that the photoresist layer remains over the wafer surface but with the metal microelectrode surface and the contact pad areas exposed. This may be followed by an etching process, such as reactive ion etching (RIE) with a mixture of $CHF_3$ and $O_2$ gases, to selectively etch away the insulative material, followed by etching of the top Ti layer to expose the Au surface of each microelectrode 20 and contact pad 18 as shown in FIG. 1. In one or more embodiments, the exposed Au surface is not a smooth surface, but rather comprises a plurality of deposited Au grains or particles, such that the overall surface area of the Au surface is increased.

Although exemplified with alternating Ti and Au, the metal layers can be any suitable combination of metal adhesion layers and conductive layers. Exemplary adhesion layers can be formed from tungsten, niobium, chromium, or titanium, or alloys thereof. Exemplary conductive layers can be formed from molybdenum, platinum, copper, silver, graphite, titanium, brass, or gold, or conductive alloys thereof. Metal adhesion layers typically have an average thickness ranging from 10 nm to 30 nm, preferably about 20 nm. The conductive layer typically has an average between about 25 to about 200 nm, between about 50 to about 150 nm, between about 75 to about 125 nm, or about 100 nm.

In one or more embodiments, each microelectrode has an approximate dimension (d) of at least about 100 μm×100 μm up to about 500 μm×500 μm, and preferably about 200 μm×200 μm. Although fabricated as substantially square electrodes, it will be appreciated that other geometries can be patterned using standard lithography techniques including circles or ovoid shapes, rectangles, triangles, etc. In one or more embodiments, the maximum dimension (e.g., diagonal of a square or rectangle, longest side of a triangle, or diameter of a circle) is about 700 μm or less, preferably about 600 μm or less, preferably about 500 μm or less, preferably about 400 μm or less, more preferably about 300 μm or less. For example, as shown in FIG. 1, the patterned microelectrodes used in the Examples each have a dimension of about 200 μm×200 μm, giving a maximum dimension of about 283 μm on the diagonal.

In one or more embodiments, for detection, a patterned polymer membrane (e.g., PDMS) 28 is positioned over the microelectrode surface. The patterned membrane 28 has a plurality of holes 32 spaced apart across the membrane with respective openings positioned above each microelectrode. The combination of the patterned membrane 28 openings and microelectrode creates a testing chip comprising a plurality of test wells 32, where the openings of the patterned membrane 28 and insulating layer 22 form the sidewalls of the wells and each microelectrode surface 20 forms the bottom surface of its respective well 32, as depicted in FIG. 3. The patterned membrane thickness (contributing to the height of each test well) preferably ranges from about 0.2 mm to about 2 mm. In one aspect, the wells have an approximate diameter of about 700 μm or less, preferably about 600 μm or less, preferably about 500 μm or less, preferably about 400 μm or less, more preferably about 300 μm or less. In one or more embodiments, the test volume of each well ranges from about 0.05 μL to about 1 μL, preferably from about 0.07 μL to about 0.9 μL, preferably from about 0.07 μL to about 0.8 μL. In one or more embodiments, each microelectrode (and corresponding test well) is spaced apart (s) in each array by approximately 500 μm to about 2 mm (as measured edge-to-edge), preferably about 800 μm to about 1 mm (between each well) to minimize overflow of samples or mixing between wells.

In one or more embodiments, the electrodes are configured to detect the presence of one or more target biomarkers in a sample. In one or more embodiments, the electrodes are configured to detect the presence of certain enzymes that are overexpressed by cancer-causing cells. Examples of these enzymes include, without limitation, various proteases such as legumain, cathepsin B, ADAM-10, MMP-7, MMP-9, trypsin, plasmin, chymase, caspase 3, urokinase, tissue inhibitor of metalloproteases (TIMPs), reversion-inducing cysteine-rich protein with Kazal Motifs (RECK), and other members in cathepsin, ADAM, MMP, and caspase families.

The metal electrode surface can first be functionalized with a mixture of 6-mercaptohexanoic acid and 6-mercapto-1-hexanol to form an even molecular layer consisting of mixed carboxylic acid and methyl terminal groups, in which the thiol moiety at the proximity end binds to the gold surface, leaving free carboxylic acid groups (thioalkanoic acid molecules) distal from the electrode surface for coupling with the peptide probes. Short substrate peptides (aka peptide probes) containing a short linker containing an amino group (e.g., aminoalkanoic acid, 5-aminopentanoyl amide) are then attached to each exposed electrode surface by formation of amide function through the coupling of the amino moiety of the linker of a substrate peptide and the carboxylic acid group of the molecular layer on the gold surface. It will be appreciated that any suitable coupling chemistry may be used to covalently attach the amine-terminated linker in the peptides to the metal electrode surface via other covalent bonds, and molecular layers can be formed with other compounds such as cysteamine (or cystamine) reacting with glutaraldehyde, and the like.

In one or more embodiments, an amine-terminated linker consisting of an alkane chain of 4 to 8 methylene groups is attached to the N-terminal of the peptide to provide higher flexibility. The peptides or peptide residues may be purchased or synthesized according to various reaction schemes, examples of which are discussed in further detail in the Examples. The peptides can be short peptides or oligopeptides that comprise a consensus sequence specific to the target biomarker, such that the peptide or particular sequence of amino acid residues within the peptide is recognized by and capable of being cleaved by the target enzyme (i.e., is a specific substrate of the target). In one or more embodiments, the consensus sequence comprises (or consists of) between 2 to 10 amino acids, between 4 to 10 amino acids, or between 4 to 15 amino acids. The peptide may include N- or C-terminal linking regions of 10 residues or less to facilitate coupling to the electrode surface and/or to the redox reporter moiety. The total peptide length is preferably less than 16 amino acid residues, more preferably from about 4 to about 12 residues, even more preferably from about 6 to about 8.

In one or more embodiments, a redox reporter moiety that is capable of undergoing a change in oxidation state may be further attached to the free or unbound end of the peptide distal from the electrode surface. The appended redox moiety provides a characteristic faradaic signal that can be separated from the unstable non-Faradaic background and other interfering redox signals. The increase of number of redox moieties would increase the redox signals (such as the peak current in AC voltammetry) and in turn enhance the detection sensitivity.

In particular embodiments, the redox moiety is an organometallic moiety, and particularly a metallocene, such as ferrocene or multiple ferrocenes, thus resulting in a ferrocenyl peptide or peptide residue. In particular embodiments, the redox moiety is methylene blue or an analog thereof. Methylene blue analogs include new methylene blue N. Other redox moieties include viologens, anthraquinone, ethidium bromide, daunomycin, ruthenium bis-pyridine, tris-pyridine, bis-imidizole, pyrene, and analogs thereof.

In each of these techniques, signal transduction is predicated on changes in the efficiency with which the attached redox label is able to transfer electrons to or from the electrode surface. This efficiency is altered by binding- and cleavage-induced changes in peptide and thus the proximity of the electrode surface to the redox reporter moiety. As noted herein, the cleavage kinetics of redox-tagged peptides is advantageously specific and directly linked to the enzymatic activity in the sample.

In one or more embodiments, different peptide substrates having different consensus sequences can be functionalized at different microelectrodes. Thus, in these embodiments, the array comprises at least two individually addressed microelectrodes in which a first peptide having a first consensus sequence is attached to at least one of the microelectrodes, and a second peptide having a second consensus sequence is attached to at least another different microelectrode. The first and second consensus sequences can be specific substrates for different biomarkers. Thus, the chip comprising the differently-functionalized microelectrodes are operable to detect the presence of at least two different enzymes contained within a biological sample brought into contact therewith. In the exemplified embodiment of a 3×3 array, each of the microelectrodes can be functionalized with different peptides to target up to nine different biomarkers.

Figure 4:
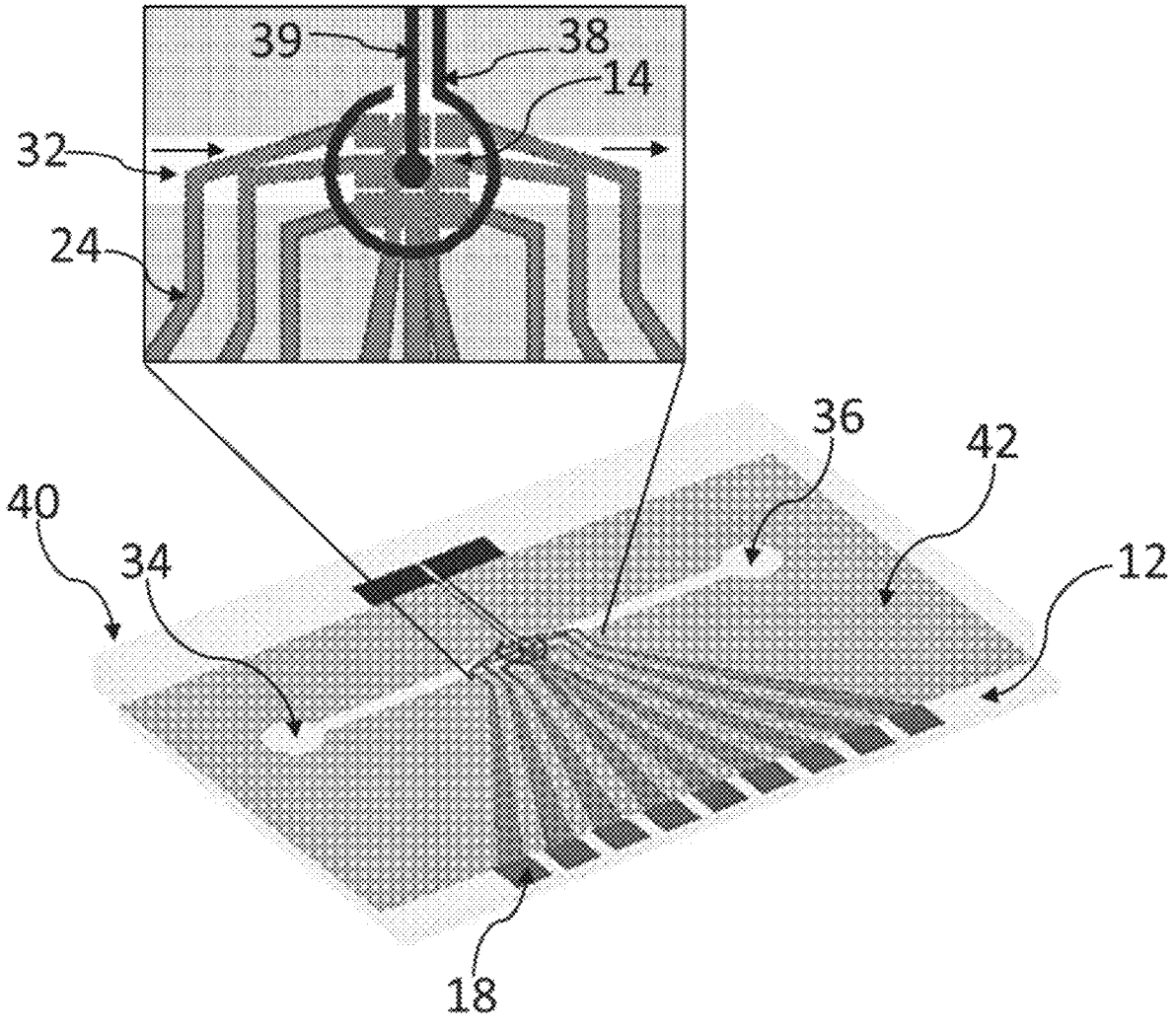
FIG. 4 is an illustration of an MEA packaged in a cartridge for use with a microfluidics or lateral flow device.

The disclosure also concerns electronic chips comprising a microelectrode array according to the various embodiments described herein, further comprising contact pads, each contact pad being connected to a respective electrode via a respective conductive lead on the chip for ACV interrogation and detection of the electrical current and changes upon contact of the electrodes with a target biomarker. The MEAs can be part of biosensor systems that comprise an electronic chip according to the various embodiments described herein. The MEA chip 12 is packaged in a plastic cartridge 40 having a microfluidic channel 32 in fluid communication with a sample inlet 34 and sample outlet 36 and configured to direct the sample into contact with each microelectrode in the array 14, as illustrated in FIG. 4. The sensor can further comprise the standard ACV components, such as counterelectrode 38 and reference electrode 39. In use, the biological sample is introduced into the inlet where it flows through the channel, across the MEA where it comes into contact with the electrodes, and towards the outlet.

In one or more embodiments, the counterelectrode and reference electrodes can be printed on the chip itself or positioned/deposited on a coverslip or other cartridge cover 42, which is brought into contact with the chip 12 with the counterelectrode 38 and reference electrodes 39 being aligned over the MEA 14 and in contact with the fluidics channel 32 (and sample flowing therethrough). The chip is positioned (sealed) within the electrochemical cell (cartridge), and the electrochemical cell is electrically connected via a breakout box to a potentiostat for interrogating and measuring via AC voltammetry the signal over time before, during, and after contacting the array with a biological sample containing or suspected of containing a target biomarker as it flows through the channel 32 and reacts with the substrate peptides on each microelectrode in the array 14.

The biosensor platform can be used with various biological samples, including, without limitation, blood, serum, urine, saliva, sweat, exhaled breath condensate, cell lysate, tissue lysate, and biopsies. In one or more embodiments, the biological sample may be directly measured without dilution (i.e., applied directly to the chip). In one or more embodiments, aliquots of the collected biological sample can be directly measured without dilution.

In one or more embodiments, the biological sample is first subjected to sample preparation. For example, the sample may be separated into aliquots and/or may be mixed or diluted with a suitable buffer system, such as phosphate buffered saline (PBS), or modified buffer system, and then separated into aliquots for testing. In one or more embodiments, a modified buffer system is mixed with the sample. The modified buffer system has a lower sodium salt concentration (~1 to 10 mM) as compared to common saline-based buffer systems (~150 mM), and preferably half of the sodium phosphate salt concentration of common PBS. In one or more embodiments, the modified buffer system is a phosphate buffer. In one or more embodiments, the modified buffer system is essentially free of chloride salts (e.g., NaCl, KCl and MgCl$_2$). As used herein, the buffer system is "essentially free" of chloride salts meaning that chloride salts are not intentionally added and are preferably removed from the buffer composition, although it appreciated that de minimis amounts of chloride salts may be present as impurities or incidental additives from the intended ingredients, and preferably means less than 1% by weight, preferably less than 0.5% by weight, more preferably less than 0.05% by weight on a total weight basis of the buffer. In one or more embodiments, the modified buffer system has a pH of from about 7.0 to about 7.5, preferably from about 7.3 to about 7.5, preferably from about 7.35 to about 7.45, more preferably about 7.4 (+/−0.02). In one or more embodiments, the modified buffer system comprises sodium phosphate dibasic heptahydrate (Na$_2$HPO$_4$·7H$_2$O) and mM sodium phosphate monobasic monohydrate (NaH$_2$PO$_4$·H$_2$O) in water.

Additives, such as surfactants or non-active agents can also be added to the buffer system prevent aggregation or unwanted interaction of the possible biomarkers in the sample with each other (instead of with the chip). In one or more embodiments, dithiothreitol (DTT) is added to activate the zymogen form of proteases. The activation process converts all inactive form of the protease (zymogen) in the sample into the active form. This step may be used to assess the fraction of the protease that presents in the active form vs. inactive form in the sample (such as human serum), which provides additional information on why the measured protease activity is higher or lower as compared to a reference sample or other detection methods (e.g., ELISA).

In one or more embodiments of the present invention, enzyme profiling within a sample is based upon a peptide proteolysis mechanism in which the target enzyme cleaves the substrate peptide(s) attached to the electrode(s) thereby resulting in a change in the peak current as measured by AC cyclic voltammetry due to the removal of the redox moiety (e.g., ferrocene) in proximity to the electrode surface. That is, initially, the presence of the redox moiety on the electrode(s) gives rise to a first detectable electrochemical signal from the sensor. For example, when the redox moiety is ferrocene (Fc), a ferrocenyl peptide, comprising ferrocene, is created, which is attached to the distal end of the peptide (extending generally away from the electrode surface), the Fc moiety can be electrochemically oxidized into ferrocenium (Fc$^+$) during AC voltammetry or other voltammetry measurements as the electrode potential is ramped from a low open circuit value (vs a reference electrode) to a more positive value (vs. the reference electrode). Reference electrodes are materials that offer a stable predictable electrode potential for comparison and avoid the need to calibrate the sensor each time. Exemplary reference electrode systems include silver/silver chloride, mercury/mercurous sulfate, mercury/mercury chloride, copper/copper (II) sulfate, and the like.

The reference electrode and ACV interrogation and analysis can be modified depending upon the particular properties of the selected redox reporter moiety. In general, a DC potential ramp within a designated voltage range and scan rate vs. a reference electrode is applied to the chip. A sinusoidal AC voltage waveform of a designated frequency and amplitude is superimposed on the DC potential ramp. The corresponding AC current is measured during the DC potential scan. The AC current will show a peak current vs. the reference electrode. The background subtracted peak AC current is proportional to the amount of redox moiety attached on the electrode surface via the substrate peptide. The peak current is monitored over time using continuously repeated ACV measurements. For example, the Fc$^+$ can be reversibly reduced back to Fc after the electrode potential returns to the initial value so that the measurement can be repeated. The electron transfers from Fc to the electrode is effective even though they are separated by the peptide and optional linker molecule. The ACV measurements are continuously repeated to interrogate the peptide attached at the electrode surface.

In an exemplary embodiment, Fc is used as the redox tag. The DC potential ramp is set at a scan rate of 5 to 100 mV/s from −0.3 V to 0.6 V (vs. Ag/AgCl reference electrode (3 M KCl)). The AC voltage amplitude is set at 5 to 100 mV and the frequency is from 5 to 1000 Hz. The oxidation of Fe to Fc$^+$ gives a peak current around +0.2 V (vs. Ag/AgCl (3 M KCl)). One ACV measurement can be completed in 20 to 120 seconds.

In another embodiment, methylene blue is used as the redox tag. The DC potential ramp is set at a scan rate of 5 to 100 mV/s from +0.1 V to −0.6 V (vs. Ag/AgCl reference electrode (3 M KCl)). The AC voltage amplitude is set at 5 to 100 mV and the frequency is from 5 to 1000 Hz. The reduction of methylene blue to leuco-methylene blue gives a peak current in the range of −0.20 to −0.40 V vs. Ag/AgCl (3 M KCl) reference electrode. One ACV measurement can be completed in 20 to 120 seconds.

After the electrodes are stabilized for from about 5 to about 10 minutes, the sample is added to the electrochemical cell. Preferably, the reaction is carried out at a temperature ranging from about 30° C. to about 45° C., more preferably from about 35° C. to about 40° C.

Upon cleavage of the peptides or peptide moieties, the redox moiety is released from the electrode surface resulting in a decrease in the detectable signal from the sensor for that electrode. Thus, in the presence of the target, there is a second detectable signal from the sensor that is different from the first signal, such as a decrease in electrical current across the array. In examples, release of the peptide fragment connected to the redox moiety results in a significant and detectable decrease in the AC voltammetry peak current across the electrode due to the loss of this moiety. In particular, if the target is present, the AC peak current starts to decrease exponentially vs. time due to cleavage of the peptide by the target biomarker. The rate of the change in signal is advantageously associated with the kinetics of the proteolysis process. The inverse of the exponential decay time constant indicates the activity of the protease. The quantitative analysis is the same regardless of the redox reporter moiety used. Proteolytic rates and kinetic profiles from a library of peptide substrates may allow distinctive detection of different enzymes, including cancerous proteases.

In particular embodiments, the frequency used for the AC voltammetry can be within the range of about 5 to about 1000 Hz, between about 10 to about 500 Hz, or between 20 to about 200 Hz. In one or more embodiments, the amplitude of the AC voltage can be within the range of about 5 to about 100 mV. In one or more embodiments, the time to complete an ACV measurement can be reduced to less than 1.5 minute, less than 60 seconds, less than 30 seconds, or less than 10 seconds. In particular embodiments, optimization of frequency and amplitude can result in completion of ACV measurements within about 60 to about 90 seconds, about 30 to about 60 seconds, or about 10 to about 30 seconds.

In one or more embodiments, the nano-/micro-electrode array chip is configured to simultaneously detect one or more overexpressed proteases in cancers, such as legumain, cathepsin B, ADAM-10, MMP-7, and MMP-9, and use a non-cancer related protease, such as chymotrypsin, trypsin or threonine proteases, as a reference. When a specific enzyme in a mixed sample solution selectively binds to its specific substrate (i.e., consensus sequence), a proteolytic reaction occurs at the electrode surface, leading to the decrease of the electrochemical signal due to the loss of the redox reporter moiety from the electrode surface. The signal over time may be recorded simultaneously at each individually addressed electrode using, for example, an integrated multiplex potentiostat with a touchscreen to display individual proteolytic reaction kinetics (or rates) and specificity patterns.

The exponential decay in the electrochemical signal can be analyzed with the heterogeneous Michaelis-Menten model below, described in greater detail in the Examples, to derive the value of $(k_{cat}/K_M)[E]$:

$$E + S_s \underset{k_{-1}}{\overset{k_1}{\longleftrightarrow}} ES_s \overset{k_{cat}}{\Longrightarrow} E + P_s + P \tag{1}$$

where E is the enzyme, $S_s$ is the intact surface-bound peptide-Fc substrate, $ES_s$ is the enzyme-substrate complex, $P_s$ is the surface bound peptide product remaining after the proteolytic cleavage, P is the Fc-tagged peptide fragment, which is free to diffuse into solution, and $k_1$, $k_{-1}$ and $k_{cat}$ are the rate constants of the respective reactions. The fundamental specificity constant (or catalytic efficiency) $k_{cat}/K_M$ (with $K_M = (k_{-1} + k_{cat})/k_1)$) can be first determined using known concentration of the proteases for calibration. The concentration of the specific proteases [E] in the unknown sample can then be determined with its kinetic data.

Embodiments of the present invention are particularly suited for application in a portable electronic system for simultaneous electrochemical signal detection by a plurality of independent channels connected to a chip comprising a plurality of electrodes. The biosensor chip can be fabricated as a disposable cartridge with a total reaction volume of about 5 μL to about 500 μL. A common reference electrode and a common platinum counter electrode may also be used, while each working electrode will be independently addressed based on phase-sensitive AC Voltammetry. The sensitivity of the system should be sufficient to detect ~0.1 nA AC current generated from the electrochemical signal. The electronic system may be reconfigured from a commercial chip (for example, LMP9100 of National Semiconductor or Atmel XMEGA microcontroller) and integrated with a specially designed circuit board into a multichannel potentiostat. A touchscreen liquid crystal display (similar to a smartphone or tablet device) may be incorporated for display as a part of a standalone handheld device.

In one or more embodiments, a data acquisition and a user interface with touchscreen technique may be developed using, for example, C# (Micro Visual Studio). Once the data is collected, the data analysis program performs a real-time analysis, including analyzing the incoming signals and displaying the enzymatic kinetics, reaction pattern based on the location of the signal source (i.e., pre-assigned specific electrode position in the array) and the completed data. The data analysis process includes subtracting the linear background and extracting the peak AC current. The value of extracted AC peak current is plotted vs. time (for ~0 to 80 minutes) as a kinetic curve. The program then initiates an automatic data fitting process using the heterogeneous Michaelis-Menten model described below. The value of the specificity constant $k_{cat}/K_M$ of each specific enzyme is pre-input according to data contained within a known library. As a result, the enzyme concentration (or activity) can be derived, and the final results can be obtained in about 30 to 120 minutes. It will be similarly appreciated that assays can be calibrated for different targets and different peptide systems using standard techniques.

Other embodiments contemplated herein include kits and materials for conducting any of the assays described herein. The methods described herein are applicable to biological samples from humans as well as for veterinary use for any suitable animal, including, without limitation, dogs, cats, and other companion animals, as well as, rodents, primates, horses, cattle, pigs, etc. The methods can be also applied for clinical research and/or study.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10"

(with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Abstract

Proteases are a large family of enzymes involved in many important biological processes. Quantitative detection of the activity profile of specific target proteases is in high demand for the diagnosis and monitoring of diseases such as cancers. This study demonstrates the fabrication and characterization of an individually addressable 3×3 Au MEA for rapid, multiplex detection of cathepsin B activity based on a simple electrochemical method. The nine individual microelectrodes in the array show highly consistent cyclic voltammetric signals in Au surface cleaning experiments and detecting benchmark redox species in solution. The individual Au microelectrodes are further selectively functionalized with specific ferrocene-labeled peptide molecules, which serve as the cognate substrates for the target proteases. Consistent proteolytic kinetics are measured by monitoring the decay of the AC voltammetry signal from the ferrocene label as the peptide molecules are cleaved by cathepsin B. Accurate activity of cathepsin B is derived with an improved fitting algorithm. Simultaneous detection of the proteolysis of cathepsin B on the MEA functionalized with three different hexapeptides is demonstrated, showing the potential of this sensor platform for rapid detection of the activity profiles of multiple proteases in various diseases including many forms of cancer.

1. Introduction

Proteases are a class of enzymes, which selectively break down proteins by targeting the specific constituent peptide sequences and cleaving the peptide bonds at specific sites. About 600 different proteases have been identified in humans, which have an active role in many cellular processes including apoptosis, angiogenesis, hormone activation, etc. Their overexpression has been found to be indicative of several diseases and medical conditions such as muscle atrophy and cancer progression. Because of their prevalence and selectivity, proteases can serve as biomarkers for medical diagnostics and targets for therapeutic drugs such as protease inhibitors. Developing rapid low-cost techniques that can quantitatively detect multiple proteases is essential for these applications.

Several methods exist currently for rapid protease quantification and the diagnostic assays fall into two categories. The first type focuses on the quantification of the overall concentration of the protease, for example, the widely used commercial enzyme-linked immunosorbent assays (ELISA) such as the Quantikine Human Pro-Cathepsin B ELISA kit by R&D Systems Inc., and various immunohistochemical assays. These affinity-based methods use specific antibodies to selectively bind the target proteases, but they normally cannot distinguish the inactive proenzymes from the active enzymes, thus cannot provide accurate information regarding the biological functions of the proteases.

The second category focuses on quantification of the activity of specific protease enzymes, i.e., the overall rate of the proteolysis reactions that are induced by the specific amount of particular proteases. Fluorogenic assays that measure the increase in fluorescence emission upon cleavage of a quenched fluorophore in a peptide substrate by the cognate protease are representative examples of such activity-based techniques. These activity-based approaches are advantageous because they account for the fact that not all the protease enzymes are active, and that the effectiveness of the proteases can vary drastically from different sources. More importantly, the enzyme activity not only depends on the concentration of the active enzyme but also the measuring conditions such as the cognate peptide substrate, buffer composition, temperature, and presence of inhibitors. By measuring the kinetic profile of the fluorogenic signal from the cleaved peptide products, the proteolytic reaction rate can be derived, which directly reflects the biochemically relevant activities of the proteases.

Electrochemical methods for quantification of protease activity have shown great promise recently. The measurements typically rely on a peptide substrate having a terminal redox moiety, often ferrocene (Fc), immobilized onto an electrode surface. The concentration of the electrode-bound redox probe provides a baseline signal, which can be observed by common electrochemical techniques such as cyclic voltammetry (CV), square wave voltammetry (SWV), differential pulse voltammetry (DPV) and AC voltammetry (ACV). The decrease in the electrochemical signal reflects the rate of peptide substrate proteolysis by the cognate protease. In our previous studies, we have found (based on a heterogeneous Michaelis-Menten enzymatic model) that the electrochemical signal decays exponentially with regard to the reaction time and the inverse of the decay time constant directly reflects the protease activity. This method has been successfully demonstrated for measuring the activity of cathepsin B, a cancer-related protease, in simple buffer solutions as well as complex samples including tissue lysates and cell lysates using a nanoelectrode array fabricated with vertically aligned carbon nanofibers.

Furthermore, electrochemical methods can be adapted to individually addressed MEAs for highly multiplex detection. Selectively functionalizing individual electrodes with peptide substrates that are specific to their cognate proteases allows mitigation of complicated cross-reactions and cascade networks of related proteases; this is enabled by collectively analyzing the activity profiles derived from the sensor arrays, similar to the mechanism that allows an array of sensory receptors in the tongue to distinguish complicated flavors. In this study, we have extended our previously demonstrated electrochemical method into a 3×3 Au MEA and demonstrate its capability for the simultaneous detection of cathepsin B activities using three different peptide substrates functionalized on the MEA. The fitting algorithm has also been refined to obtain more accurate results. The results from the nine electrodes in the MEA are highly consistent, enabling its applications for reliable screening of peptide substrate candidates. These advances lay the foundation for future multiplex electronic chips that can be used for rapid detection of protease activity profiles in disease diagnosis and treatment monitoring.

2. Materials and Methods:

2.1 Reagents:

N-Fluorenylmethyloxycarbonyl (Fmoc) protected amino acids, amino acid attached 2-chlorotrityl resins, 1-[bis(dimethylamino)methylene]-1H-1,2,3-triazolo[4,5-b]pyridinium 3-oxide hexafluorophosphate (HATU), and 2-(1H-benzotriazol-1-yl)-1,1,3,3-tetramethyluronium hexafluorophosphate (HBTU) were purchased from Chem-Impex International, Inc. (Wood Dale, IL) and AAPPTEC LLC (Louisville, KY). Potassium hexacyanoferrate (II) trihydrate, potassium nitrate, 1-ethyl-3-(3-dimethylaminopropyl)carbodiimide (EDC), N-hydroxysulfosuccinimide (Sulfo-NHS), 6-mercapto-1-hexanol, and 6-mercapto-1-hexanoic acid were obtained from Sigma-Aldrich (St. Louis, MO). Dithiothreitol (DTT), sodium phosphate dibasic heptahydrate ($Na_2HPO_4 \cdot 7H_2O$), sodium phosphate monobasic ($NaH_2PO_4$) and 2-(4-morpholino)ethanesulfonic acid (VIES) were purchased from Fisher Scientific (Hampton, NH). Purified recombinant human cathepsin B (~60% 37 kDa inactive form and ~40% 25 kDa active form) was acquired from R&D Systems Inc. (Minneapolis, MN). Cathepsin B solutions were activated by incubation in 25 mM MES buffer (pH=5.0) containing 5 mM DTT for 15 min before proteolysis experiments.

Figure 9:
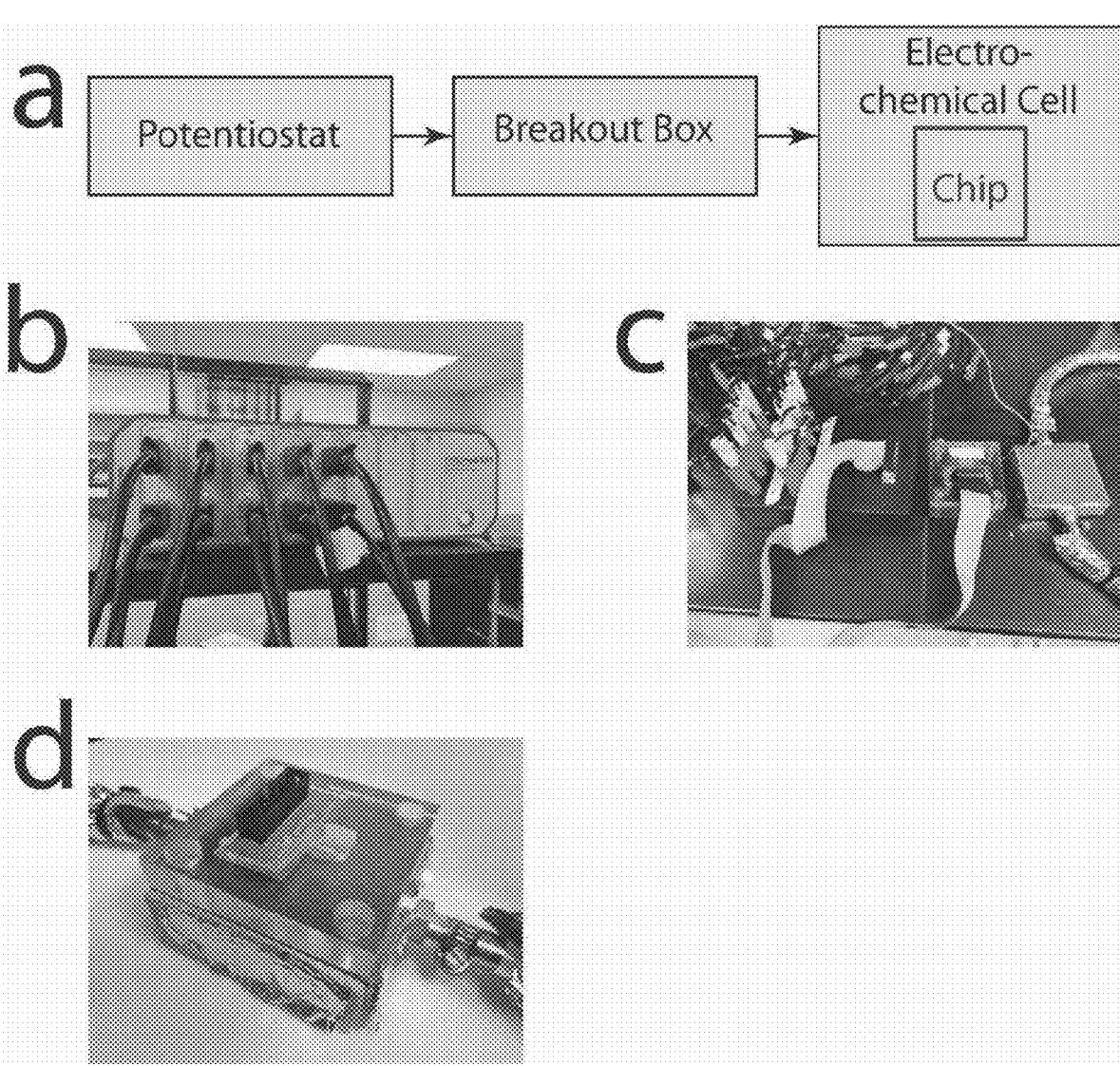
FIG. 9 shows photographs of the experimental setup. (a) Box diagram of multiplexed experimental setup. (b) Photograph of the Ivium n-Stat potentiostat. (c) Photograph of the breakout box, electrochemical cell and copper base plate. (d) Photograph of the electrochemical cell fitted with the copper base plate.

2.2 Electrochemical Measurements:

Electrochemical measurements were performed using an Ivium n-Stat Potentiostat (Eindhoven, The Netherlands) outfitted with five dual channel modules, allowing up to ten independent working electrodes to function simultaneously with a common reference and counter electrodes. The experimental setup is shown in FIG. 9. FIG. 9$a$ shows a block diagram of the experimental setup. In this study, the nine leads from the potentiostat (FIG. 9$b$) were interfaced with a breakout box, which was then connected to a custom-built electrochemical cell via a ribbon cable (FIG. 9$c$). The sensor chip consists of nine lithographically patterned Au working microelectrodes placed in the custom-built electrochemical cell (FIG. 9$d$) and electrical contact was made via pogo pins. All measurements were performed using a common mercury/mercurous sulfate reference electrode (Hg/$Hg_2SO_4$, MSE) filled with a saturated solution of $K_2SO_4$ (CH Instruments, Austin, TX) and a common Pt wire counter electrode.

Figure 5:
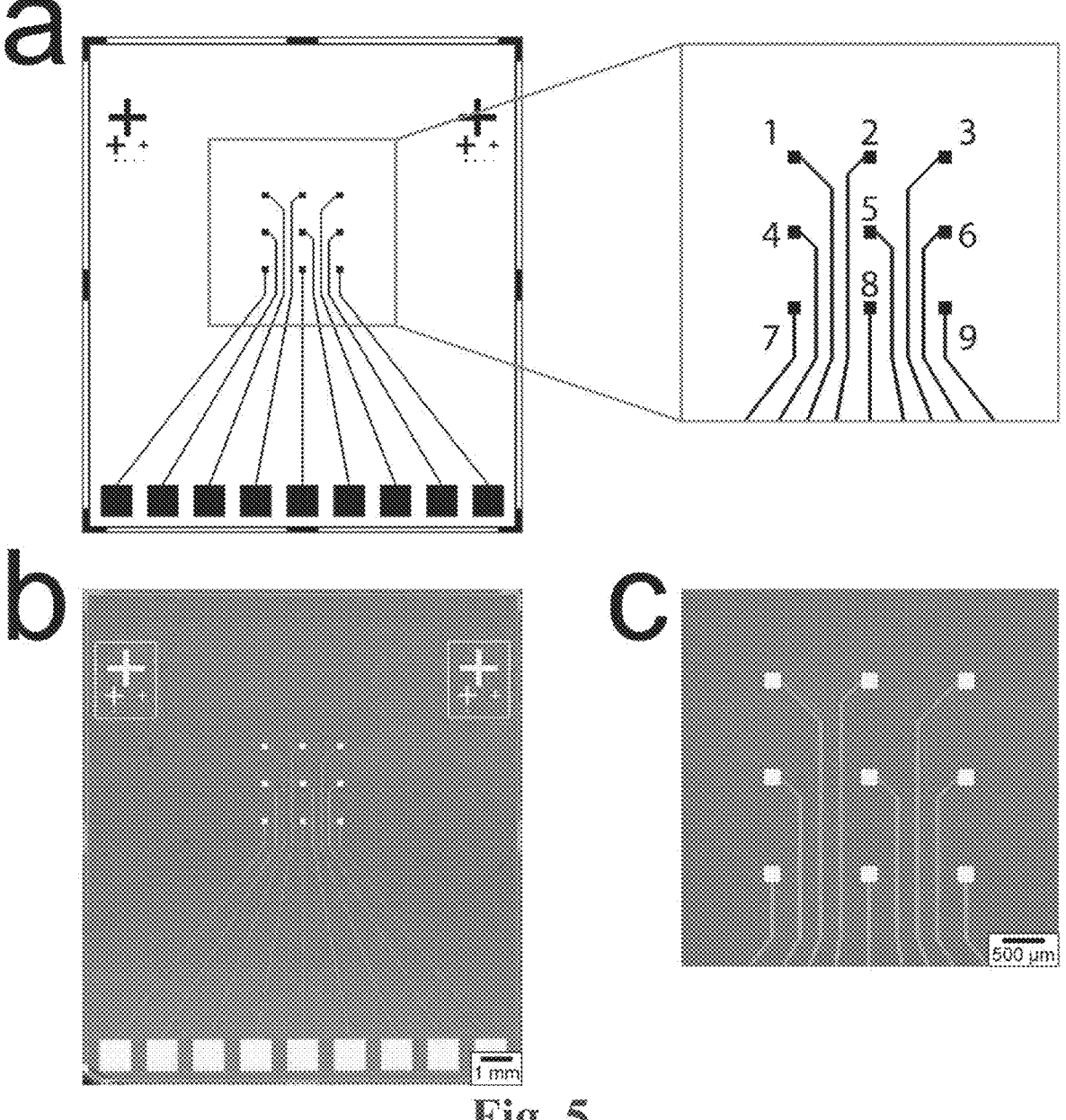
FIG. 5 shows (a) Schematic diagram of the Au MEA chip layout with a zoom-in picture (right side) to illustrate the channel numbering scheme. (b) and (c) Optical micrographs of a fabricated Au MEA chip.
Figure 10:
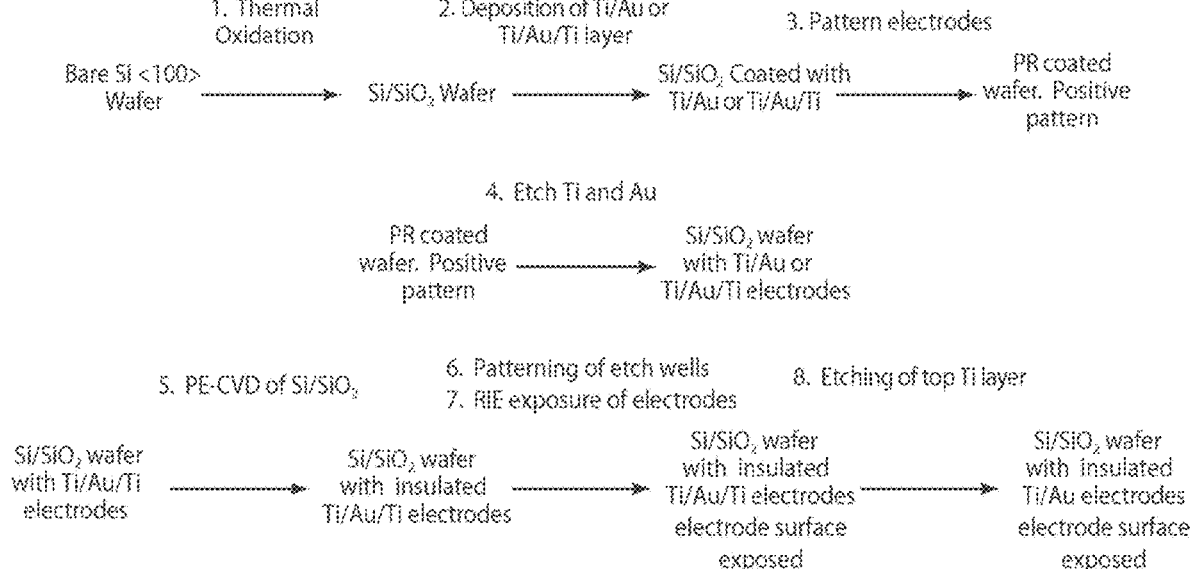
FIG. 10 is a flowchart of the fabrication workflow for wafer-scale MEA fabrication.
Figure 11:
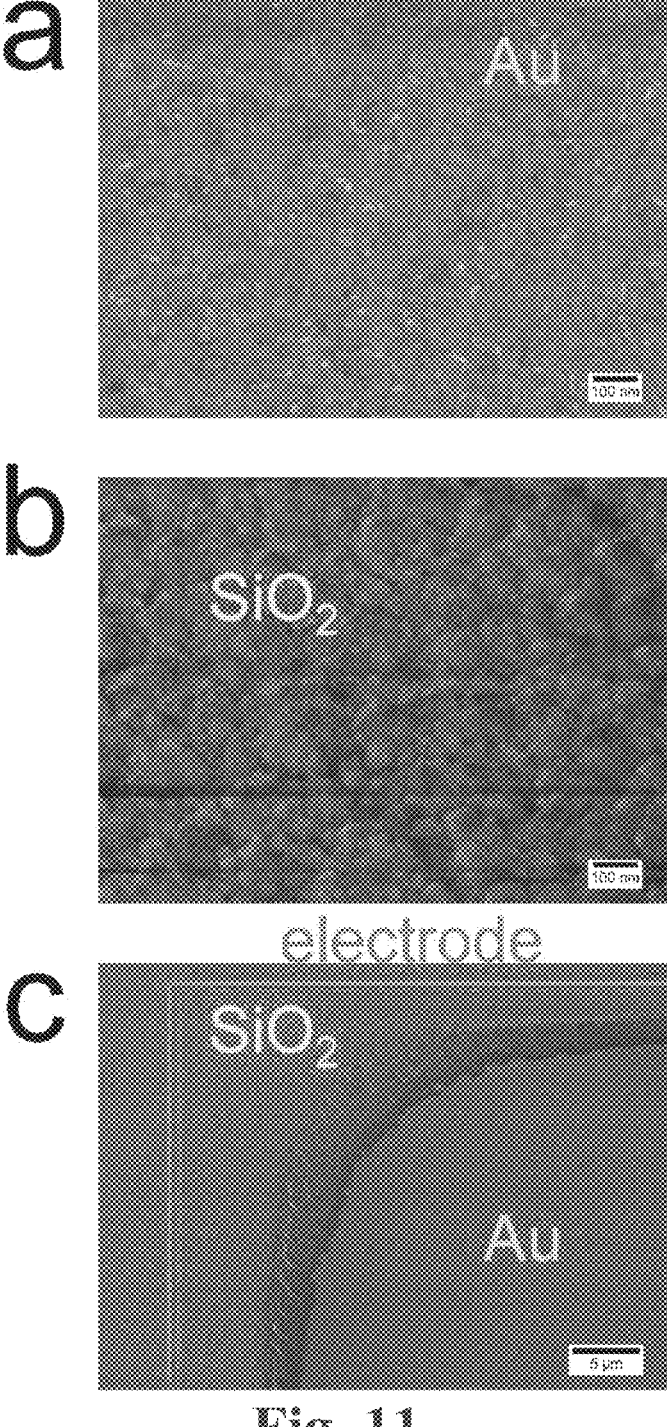
FIG. 11 shows SEM images of different regions of a MEA: (a) an exposed Au surface, (b) the top surface of the PECVD $SiO_2$ layer, and (c) the boundary between the top $SiO_2$ layer and the exposed Au surface.

2.3 Device Fabrication:

Device fabrication was performed at the Stanford Nanofabrication Facility (Stanford, CA). A workflow of the wafer-scale fabrication process is shown in FIG. 10. Thermal oxidation of standard 4" Si<100> wafers was performed by ramping the temperature to 1100° C. and holding for 45 min in the presence of gaseous $H_2O$. This produced a thermal oxide with a thickness of ~550 nm. Next, the wafers were coated with 20 nm Ti, 100 nm Au and another 20 nm Ti by electron beam evaporation (Innotec ES26C, Battle Ground, WA). The wafers were then spin-coated with an automated spin-coating track (SVG 8400, San Jose, CA) with 1.0 μm SPR3612 positive photoresist (Rohm and Haas Electronic Materials, Marlborough, MA) and exposed on a mask aligner (Karl Suss MA-1, Garching, Germany) with an exposure dose of 80 mJ/cm² (exposure time=5.3 s) through a chrome photomask (FrontRange Photomask, Lake Havasu City, AZ). Next, the wafers were developed with an automated developing track (SVG 8600, San Jose, CA), leaving the electrode MEA design patterned in photoresist. The exposed areas on the wafers were then etched with a ratio of 1:50 of HF:$H_2O$ to remove the top layer of Ti, with Transene TFA Au etchant to remove the Au layer, and again with 1:50 HF:$H_2O$ to remove the bottom layer of Ti, leaving the MEA pattern (including contact pads, leads and the microelectrode surface). After etching, the photoresist was stripped off and a 1-μm thick layer of $SiO_2$ was deposited over the entire wafer by plasma-enhanced chemical vapor deposition (PE-CVD, Plasma-Therm Shuttlelock SLR-730-PECVD, St. Petersburg, FL) with 250 sccm 5% $SiH_4$/He, 800 sccm He and 1700 sccm $N_2O$ at 350° C., 1100 mTorr and 200 W for 15 min. Next, the $SiO_2$-coated wafer was spin-coated with a 1.0-μm layer of SPR3612 positive photoresist and subsequently exposed with an exposure dose of 80 mJ/cm² leaving the $SiO_2$ over the microelectrode surface and the contact pads exposed. The exposed $SiO_2$ was etched with $CHF_3$ plasma (2 sccm 02 and 45 sccm $CHF_3$ at 5.0 mTorr for 8 min) using a reactive ion etcher (RIE, Plasma-Therm Versaline LL-ICP, St. Petersberg, FL), and then the top layer of Ti was etched with HF and $H_2O$ (1:50) to expose the Au surface. Finally, the wafers were coated with a 5.0-μm layer of SPR3612 as a protective layer and the individual chips were diced with a wafer saw (DISCO DAD3240, Tokyo, Japan). Prior to use, the chips were sonicated in acetone and sequentially rinsed with acetone, methanol and isopropanol to remove any residual photoresist. FIG. 1 illustrates the top and side view of the MEA structure, and the schematic diagram and photographs of the chips are shown in FIG. 5. FIG. 11 shows the SEM characterization of the fabricated Au MEAs.

2.4 Peptide Synthesis:

A library of nine peptide substrates was examined initially for proteolysis using cathepsin B (Table S1). Tetra-, hexa- and octa-peptide substrates having similar sequences have been studied, and hexapeptides were found to yield the optimal signal. The order and amino acid sequence of the peptide substrates were designed according to the literature reported sequences with minor modifications. Among the nine peptides, three most reactive peptide substrates, i.e., H-3, H-15, and H-16 (Table 1), were selected for our studies on cathepsin B activity profiling. The peptides were designed based on literature reports and synthesized using a solid-phase microwave peptide synthesizer detailed in the Supporting Information below. For example, peptide H-15, a representative peptide, was made by the coupling of H-Ala-2-chlorotrityl resin with various N-fluorenylmethyloxycarbonyl-amino acids (N-Fmoc-amino acids) sequentially, condensing with the linker N-Boc-NH—($CH_2)_4$—$CO_2H$, cleavage of the peptide from the resin, re-protection of the amino group of linker, bonding with (aminomethyl) ferrocene, and removal of the protecting group.

TABLE 1

| Hexapeptide Sequences | | |
|---|---|---|
| Peptide Name | Structure | SEQ ID NO: |
| H-3 | $H_2N$-($CH_2)_4$-CO-Pro-Leu-Arg-Phe-Gly-Ala-NH-$CH_2$-Fc | 1 |
| H-15 | $H_2N$-($CH_2)_4$-CO-Pro-Leu-Ala-Phe-Val-Ala-NH-$CH_2$-Fc | 2 |
| H-16 | $H_2N$-($CH_2)_4$-CO-Pro-Leu-Ala-Gly-Val-Ala-NH-$CH_2$-Fc | 3 |

2.5 Electrode Preparation:

Prior to use, the MEAs were sonicated in acetone for 1 minute, subsequently rinsed with methanol and isopropanol for 15 s and then dried by blowing with nitrogen. Next, the electrodes were placed in the experimental cell and electro-chemically cleaned by cycling from −0.60 to 0.70 V vs. MSE in 0.10 M phosphate buffer (pH=7.4). For the experiments using an MEA modified with the same peptide-Fc substrate (i.e., H-15) on all nine microelectrodes, the whole chip was incubated in a mixture of 1.0 mM 6-mercapto-1-hexanol and 0.2 mM 6-mercapto-1-hexanoic acid in deionized water for 40 min to form a self-assembled monolayer (SAM). This step passivated the entire Au microelectrode surface while leaving adequate spacing between the exposed carboxyl functionalities. Next, the electrodes were incubated in a solution containing 2.0 mM peptide-Fc substrate (i.e., H-3, H-15, or H-16), 0.20 g/l EDC and 0.20 g/l sulfo-NHS for 2 hours at room temperature so that the peptides were covalently attached to the carboxyl groups of the SAM through the formation of amide bonds. The low ratio of carboxyl to hydroxyl groups at the SAM surface ensured a large separation between the peptide-Fc molecules which was important to reduce the steric hindrance during subsequent proteolysis measurements. Finally, the electrodes were rinsed with deionized water to remove any non-bound peptide-Fc substrate that may be physiosorbed on the surface. For multiplex experiments, the chip was masked with a ~1.2 mm thick polydimethylsiloxane (PDMS) film punched with a 3×3 array of ~0.7 mm diameter holes that were aligned on top of each Au microelectrodes. About 100 μl mixed thiol solution (6-mercapto-1-hexanol and 6-mercapto-1-hexanoic acid) as described above was added on the chip surface to fill all nine PDMS holes and was incubated for 40 min. Then, the microelectrodes and wells were rinsed and dried on a hot plate at 35° C. Finally, 0.50 μl of the EDC/sulfo-NHS/peptide-Fc (H-3, H-15, or H-16) reaction mixture was added to each well using a nanoinjector mounted on a x-y-z-micromanipulator and incubated for 2 h. The functionalized MEA was then rinsed with DI water and immediately used for the proteolysis measurements.

2.6 Proteolysis Measurements:

Proteolysis experiments were performed around 37° C. using a heat sink plate fabricated from a copper block with a drilled through-hole and fittings to circulate heated silicone liquid from a thermal circulator (Julabo F12, Allentown, PA). The MEA chip was mounted on the copper block and the thermal circulator was set at 41.2° C. in order to maintain the MEA at about 38.6° C. Cathepsin B solutions were activated by incubation in 25 mM MES buffer (pH=5.0) containing 5.0 mM DTT for 15 min prior to proteolysis experiments. About 10 μl activated cathepsin B was added into the electrochemical cell containing 815 μl assay buffer, i.e., 25 mM MES buffer (pH=5.0). Continuously repeated ACV (with an AC frequency of 300 Hz and 100 mV amplitude superimposed on a DC ramp from −0.45 V to 0.20 V vs. MSE) was recorded over the independently addressed 3×3 MEA for a period starting from about 5-10 min before adding the activated protease solution to about 85 min afterwards.

3. Results and Discussion:

3.1 MEA Design:

Microfabricated chips are commonly used in multiplex electrochemical sensor devices. However, careful planning is needed to ensure that the microfabricated chips are suitable for the specific applications. In the current study, 3×3 Au MEAs (MEAs) were fabricated so that measurements could be performed simultaneously on nine independently operating electrodes. FIG. 5a shows the schematic of the MEA chip design with a zoomed-in portion on the right side to indicate the numbering scheme of the MEA. The microelectrodes were 200 μm×200 μm and separated by 1000 μm to provide enough space to individually functionalize each electrode. The contact pads (lined up in the row at the bottom) were 1000 μm×1000 μm to provide adequate space for electrical contact via pogo pins outside the electrochemical cell. The on-chip leads from the contact pads to the electrodes were 20 μm wide, providing good electrical connections at low resistance (~110Ω). FIG. 5b shows an optical micrograph of the whole chip and FIG. 5c shows a zoom-in optical image of the MEA similar to the numbering scheme in FIG. 5a.

FIG. 1 shows the top and side views illustrating the structure of the MEA chip. The chips were fabricated on 100 mm Si wafers with a 550 nm layer of thermally grown $SiO_2$ as an insulating dielectric. Each wafer contains 20 MEA chips. The electrodes, leads and contact pads consisted of a 20-nm Ti adhesion layer and 100 nm Au. FIG. 11a is an SEM micrograph of the exposed Au showing the individual grains of the Au film. An additional 20-nm adhesion Ti layer was patterned onto the electrode leads and a 1.0-μm $SiO_2$ dielectric layer was deposited and patterned to insulate the leads and the chip surface while leaving the microelectrodes and contact pads exposed. As shown in FIG. 11b, the top $SiO_2$ surface is significantly rougher than the exposed Au and significant charging is observed in the micrograph due to the insulating nature of the $SiO_2$ dielectric layer.

The exposed microelectrodes and contact pads appear in gold color in FIGS. 5b and 5c while the leads buried underneath $SiO_2$ appear in blue. FIG. 11c shows an electron micrograph of the boundary between the topmost $SiO_2$ layer and the exposed Au of the electrode. It is clear that the 200 μm×200 μm microelectrode is not fully exposed. A small portion (~3-7 um wide) of the Au microelectrode, particularly at the corner, is embedded underneath the $SiO_2$ dielectric layer. This only induces very small variations in the microelectrode area but is not expected to impact the proteolysis measurements in this study. In fact, it prevents the Ti underlayer from being exposed at the edge of the electrode and helps to make the Au MEAs more stable and useable repeatedly.

3.2 Cyclic Voltammetry Characterization:

Electrochemical characterization is crucial to ensuring that the MEAs are suitable for sensing applications. Cyclic voltammetry (CV) is the most common method for characterizing the electrochemical behavior of sensors. CV measurements of well-known electrochemical processes can be used to evaluate the electrode surface and charge transfer kinetics.

Figure 6:
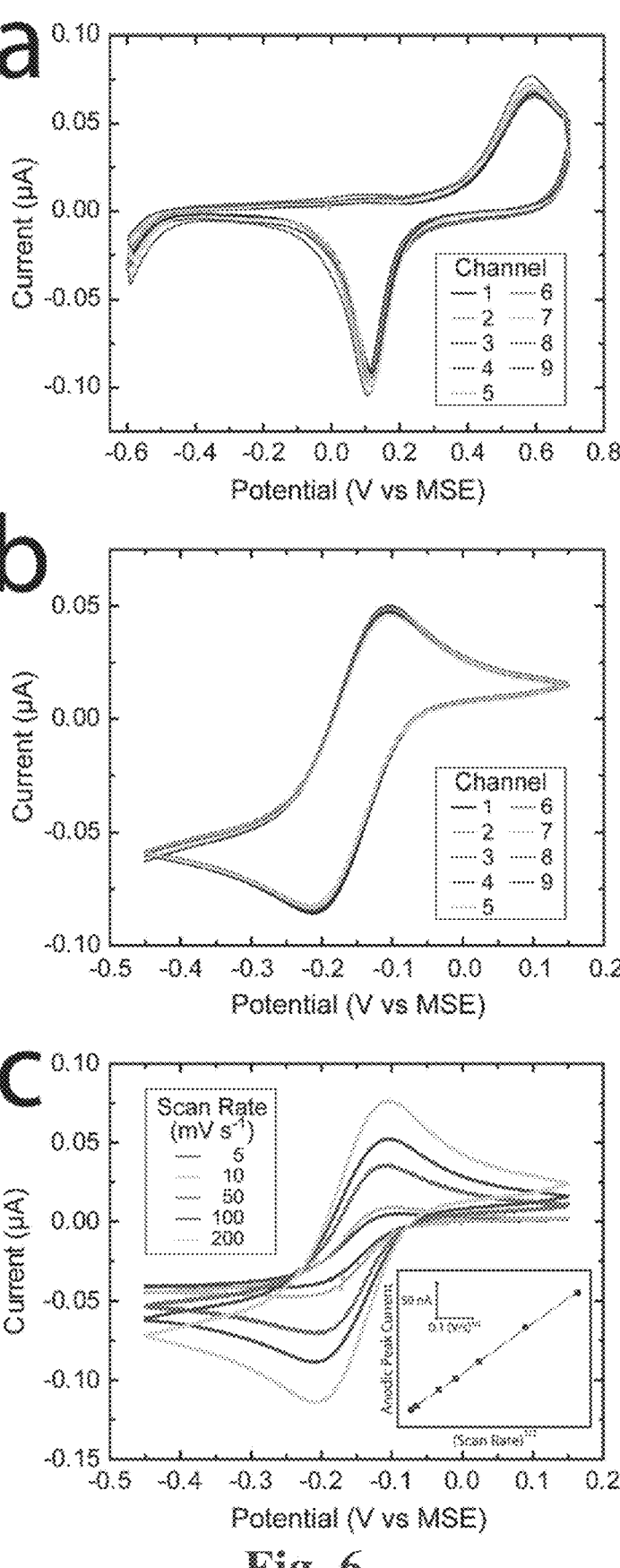
FIG. 6 shows the electrochemical characterization of an insulated, unmodified MEA chip. (a) Electrochemical oxidation of Au performed in 0.10 M phosphate buffer (pH=7.4). The measurements were performed on all nine channels simultaneously with scan rate (v)=100 mV/s. (b) Simultaneous, multiplex measurement of $Fe(CN)_6^{4-}$ oxidation on all nine channels simultaneously. The measurements were obtained in a solution containing 1.0 mM $K_4Fe(CN)_6$ and 0.10 M $KNO_3$ with a v=100 mV/s. (c) The dependence of v on $Fe(CN)_6^{4-}$ oxidation. The measurements were obtained using only channel 5 in a solution containing 1.0 mM $K_4Fe(CN)_6$ and 0.10 M $KNO_3$.

Electrochemical cleaning of Au is a common characterization method for evaluating the quality of Au electrodes. These measurements were performed by sweeping the Au electrode potential from −0.60 to 0.70 V vs. MSE and back for 10 full cycles. Typically, Au cleaning on bulk electrodes is performed in 0.10 M $H_2SO_4$. However, cycling at low pH appears to cause dissolution and delamination of both Au surface and the underlying Ti adhesion layer. Consequently, these experiments were performed in phosphate buffer (pH=7.4), which has been reported previously. FIG. 6a shows the tenth complete cycle of an electrochemical Au cleaning performed simultaneously on all nine electrodes. The potential begins at −0.60 V and a slightly negative current is observed due to the onset of hydrogen production by water electrolysis. As the applied potential is increased (moving from left to right), the current increases to ~0 μA indicating that no electrochemical reaction takes place. As the potential continues to move in the positive direction, the current becomes more positive, resulting in a localized peak at 0.60 V. This anodic current is indicative of the formation of $Au_2O_3$ on the electrode surface. The potential sweep continues to 0.70 V, which is known to form a complete monolayer of $Au_2O_3$ on the electrode surface.

The potential sweep is then reversed. As the potential continues to move in the negative direction, a cathodic peak emerges at 0.11 V vs. MSE. This peak arises from the reduction of $Au_2O_3$ to Au, and the charge associated with the peak is directly related to the number of Au atoms present on the electrode surface. The average peak height is −94.3±4.7 nA across all nine electrodes, indicating that they all behave consistently with very similar exposed Au surface areas. These Au cleaning CVs show the characteristic features of clean polycrystalline Au electrodes.

Another common voltammetric characterization technique is the oxidation of a benchmark $K_4Fe(CN)_6$ species as shown in FIG. 6b. Here, the electrodes are cycled between −0.45 to 0.15 V vs. MSE at a scan rate (v) of 100 mV/s in a solution containing 1.0 mM $K_4Fe(CN)_6$ and 0.10 M $KNO_3$. Initially, the electrode potential is swept in the positive direction beginning at −0.45 V vs. MSE. As the potential increases, the anodic current increases due to the oxidation of $Fe(CN)_6^{4-}$ to $Fe(CN)_6^{3-}$ and forms a peak at −0.11 V vs. MSE followed by a gradual decay in the current. Upon reversing the potential sweep at 0.15 V vs. MSE, similar behavior is observed in the cathodic direction showing a peak at −0.21 V vs. MSE. The peak separation was 0.10 V, in agreement with similar studies of the $Fe(CN)_6^{3-/4-}$ redox couple. The observed half peak potential ($E_{1/2}$) was −0.16 V vs. MSE. The average anodic and cathodic peak heights for all nine channels were 79.0±1.8 nA and −80.9±1.3 nA, respectively, demonstrating good agreement across all nine microelectrodes. This behavior is typical for electrochemical reactions of solution-based redox species.

The final electrochemical characterization performed here with benchmark species was the examination of the dependence of v on the oxidation/reduction of $Fe(CN)_6^{4-}$ by CV. Varying v allows for evaluation of the mass-transport properties of the electrochemical reaction. Changes in the shape of the current transient and $i_p$ with v provide information about the electrode geometry and the electrochemical reaction. FIG. 6c shows several CVs obtained on the same microelectrode, channel (CH) 5, at different values of v. The CV trace shows a sigmoidal shape at the lowest value of v (5 mV/s, black line). This sigmoidal shape is a characteristic electrochemical behavior of microelectrodes and occurs because the radial diffusion at the electrode edges is relatively larger than the linear diffusion normal to the electrode surface, resulting in a mass-transport limited steady-state current. Slow values of v allow more time for the diffusion layer to grow and reach the steady state. As v increases to 10 mV/s (yellow line), small anodic and cathodic peaks emerge at −0.102 V and −0.233 V, respectively. At higher values of v, the reactants near the electrode surface are depleted faster than diffusion layer development. As v further increases to 50 mV/s (blue line), the anodic and cathodic peaks shift to −0.116 V and −0.206 V, respectively, and the peak heights increase. At even higher values of v, the peak potentials remain relatively constant, and the peak heights continue to increase. The inset of FIG. 6c shows a plot of the anodic values of $i_p$ vs. $v^{1/2}$. The data for anodic $i_p$ demonstrates a linear relationship with $v^{1/2}$, indicating that the observed signal is dominated by linear diffusion relative to radial diffusion. This is typical for electrochemical reactions of solution-based species under diffusion-controlled conditions. These results demonstrate that our Au MEAs behave as expected and are suitable for use as electrochemical sensors.

Figure 13:
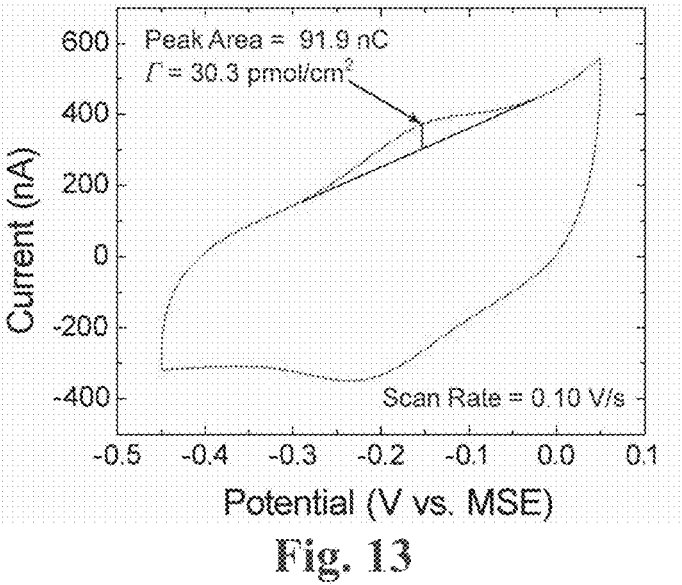
FIG. 13 shows a cyclic voltammogram of an Au macro disk electrode (2.0 mm diameter) after modification with peptide-substrate H-3. The CV was obtained in a solution containing 1.0 M KCl with v=0.10 V/s.

3.3 Multiplex Proteolysis:

After validation using optical and electrochemical characterizations, the MEAs were used to develop a sensor for the simultaneous, selective detection of protease activities. This was achieved by modifying the electrode surface with a SAM in an aqueous solution of mercaptohexanol and mercaptohexanoic acid and then tethering the peptide-Fc substrate to the exposed carboxyl groups, as described in the Experimental Section. CV characterization using an Au disk electrode of 2.0 mm diameter (FIG. 13) reveals the density of functionalized peptide-Fc (T) using this protocol to be about 30.3 pmol/cm², giving an average spacing of 2.46 nm. The actual spacing may be larger because the effective surface area is often larger than the geometric surface area. Such surface concentration is significantly lower than the maximum expected surface coverage for a close-packed Fc-terminated SAM (460 pmol/cm²). The low density allows adequate space between the peptide chains for proteolysis reactions to occur without significant steric hindrance while passivating the electrode surface to decrease capacitance, thus improving the signal-to-noise ratio in the electrochemical measurements.

Figure 14:
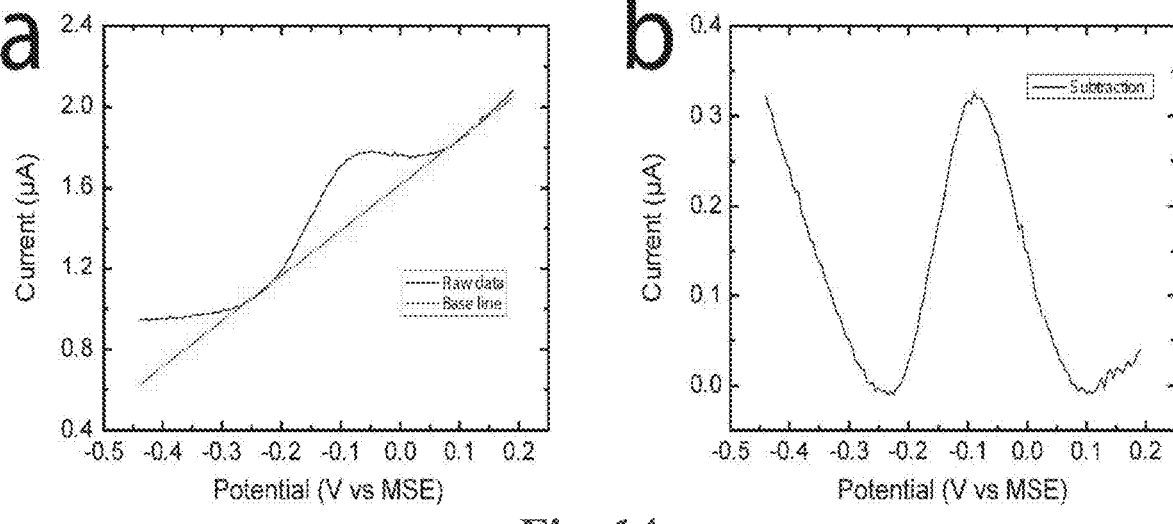
FIG. 14 shows base line subtraction of ACV data. The ACV data was obtained on a single channel of a peptide-Fc modified MEA. (a) Raw data (black trace) and a linear baseline (red) of ACV data obtained with a peptide modified Au electrode. (b) The processed ACV curve after baseline subtraction.

The sensing strategy is illustrated in FIG. 2. The left side of FIG. 2a shows a cartoon of the electrode prior to any proteolysis reaction. The gold box represents the Au electrode surface, the wavy black lines are the alkanethiols bound to the electrode surface and the green wavy lines are the exposed Fc-terminated peptide sequence. Here, all the Fc tags can be oxidized into ferrocenium ($Fc^+$) by transferring electrons to the electrode as depicted by the red arrows. This electron transfer corresponds to an ACV peak depicted by the red trace in FIG. 2b. An experimental example of the unprocessed ACV obtained from a peptide-Fc modified Au microelectrode is shown in FIG. 14a in the SI. The black trace shows the experimental signal, which revealed a Gaussian peak near −0.05 V vs. MSE on top of a tilted background as shown by the red line in FIG. 14a. The baseline is subtracted from the ACV curve to result in a well-defined peak as shown in FIG. 14b.

When the target protease is added to the sample chip, it cleaves the peptides, causing the tethered Fc-moieties to diffuse away from the electrode surface. This leads to a decrease of electron transfer as illustrated by the blue arrow on the right half of FIG. 2a. As a result, the ACV peak becomes smaller as represented by the blue trace in FIG. 2b. FIG. 2d shows a theoretical plot of the ACV peak height ($i_p$) vs. time of the proteolytic reaction where t=0 min is defined as the first measurement after protease injection. These plots are hereafter referred to as proteolysis plots. Focusing first on the red curve, $i_p$ is stable prior to the injection time. After the protease is injected into the electrochemical cell, the peak signal decays exponentially until approaching zero. As the activity of the protease increases, the proteolysis reaction rate is raised as depicted by the blue and pink curves, indicated by the faster decay in $i_p$.

Previously, we have shown that this exponential decay in $i_p$ corresponds to the proteolysis kinetics predicted by the Michaelis-Menten model for heterogeneous enzymatic reactions. The model is based on the enzymatic reaction:

$$E + S_s \underset{k_{-1}}{\overset{k_1}{\rightleftarrows}} ES_s \overset{k_{cat}}{\Rightarrow} E + P_s + P \tag{1}$$

where E is the enzyme, $S_s$ is the intact surface-bound peptide-Fc substrate, $ES_s$ is the enzyme-substrate complex, $P_s$ is the surface bound peptide product remaining after the proteolytic cleavage, P is the Fc-tagged peptide fragment, which is free to diffuse into solution, and $k_1$, $k_{-1}$ and $k_{cat}$ are the rate constants of the respective reactions. Based on this model, the decay in the experimental signal, v, is described as $$v = -\frac{d\Gamma_{S_S}}{dt} = \frac{k_{cat}}{K_M + [E_0]}[E_0]\Gamma_{S_S}, \tag{2}$$

where $\Gamma_{S_s}$ is the surface concentration of $S_s$ and $K_M = (k_{cat} + k_{-1})/k_1$ is the Michaelis-Menten constant. Because $i_p \propto \Gamma_{S_s}$, we can write $$\frac{\Gamma_S}{\Gamma_{S0}} = \frac{i_p}{i_{p0}}. \tag{3}$$

By making the assumption $K_M \gg [E_0]$ and combining eq 2 and eq 3, we have:

$$-\frac{d^{i_p/i_{p0}}}{dt} \approx \frac{k_{cat}}{K_M}[E_0](i_p/i_{p0}), \tag{4}$$

Integrating eq 4 with respect to $i_p/i_{p0}$ yields:

$$t = \int -\frac{K_M}{k_{cat}[E_0]}\frac{1}{i_p/i_{p0}}d(i_p/i_{p0}) = -\frac{K_M}{k_{cat}[E_0]}\ln(i_p/i_{p0}), \tag{5}$$

which can be rearranged to $$i_p = i_{p0}\exp[-t/\tau], \tag{6}$$

where $1/\tau$ is:

$$\frac{1}{\tau} = \left(\frac{k_{cat}}{K_M}\right)[E_0] \tag{7}$$

The value of $1/\tau$ is defined as the activity of the target protease on the specific peptide-Fc substrate and directly corresponds to the decay rate of $i_p$.

Figure 15:
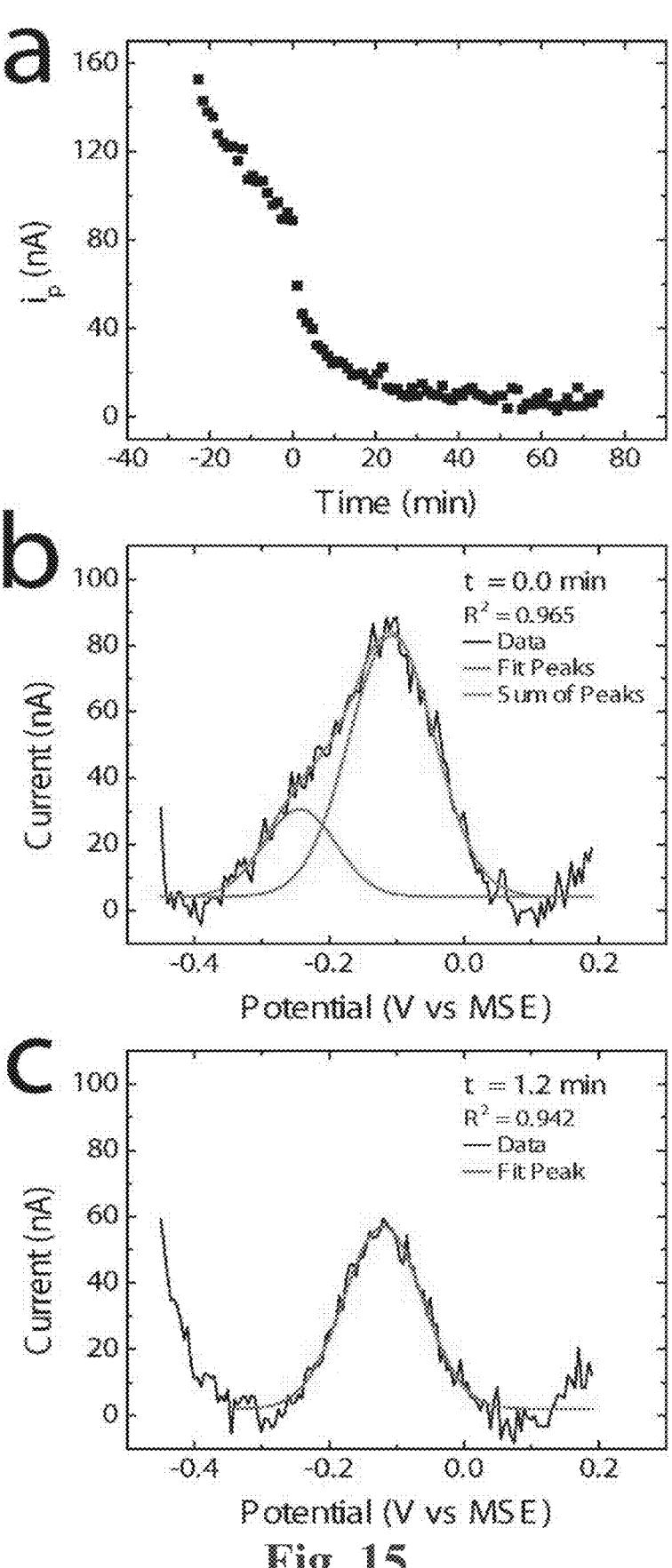
FIG. 15 shows examples of non-idealities in proteolytic measurements. (a) Full proteolysis curve demonstrating the initial drift in peak current drift prior to the protease injection (t<0). The raw ACV curve showing (b) an interference peak at ~−0.25 V (vs. MSE) at t=0.0 min and (c) the disappearance of the interference peak at t=1.2 min shortly after adding the protease solution.

While this model has been demonstrated in previous reports, several non-idealities have been observed which we have sought to account for here. These non-idealities are highlighted in FIG. 15. First, as illustrated in FIG. 15a, the baseline value of $i_p$ decreased linearly prior to the injection of the target protease. This is attributed to the instability of the exposed Fc moiety. A linear term has been added to eq 6 to account for this:

$$i_p = a[\exp(-t/\tau)] + bt + c \tag{8}$$

and consequently, the value of $i_{p0}$ is redefined as $$i_{p0} = a + c. \tag{9}$$

Eq 8 has been used to fit the proteolysis data and derive the value of $1/\tau$ for each proteolysis measurement.

Furthermore, there is a large drop in signal after the cathepsin B is injected into the electrochemical cell. The cause of this large decrease is illustrated in FIGS. 15b and 15c which show ACV traces obtained at t=0 min and t=1.2 min, respectively. The data in FIG. 15b can be fitted into two overlapping Gaussian peaks: the Fc signal peak at −0.101 V vs. MSE and an interference peak at −0.243 V vs. MSE. The cause of the interference peak is not clear yet, but it was observed to be present in ACV traces in some experiments before t=0 min and always disappeared after adding the protease solution (i.e., where t>0 min). FIG. 15c shows the ACV trace obtained at t=1.2 min, which is the first measurement after t=0 min. Here, the ACV data can be reliably fitted to a single Gaussian peak ($R^2$=0.943). The presence of the interference peak at t=0 min and its subsequent absence at later time causes a decrease in the overall current leading to a large drop in $i_p$ observed at these time points. Consequently, all data analysis and fitting have been performed omitting the measurement at t=0 min.

Figures 7, 8:
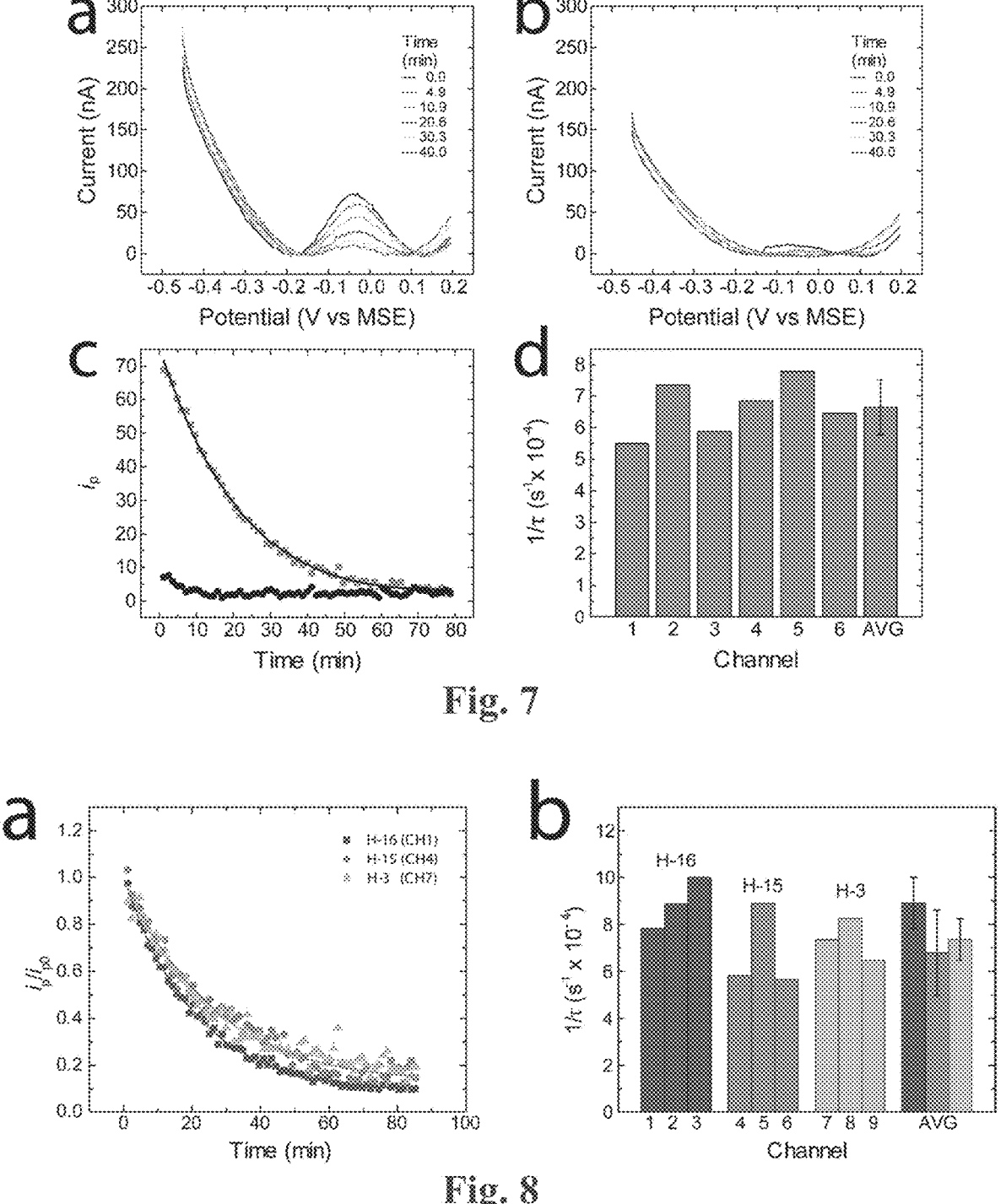
FIG. 7 shows proteolysis measurements obtained with an Au MEA. Measurements were performed in a solution containing 50 mM MES buffer (pH=5.0) and 6.0 nM cathepsin B. The protease was injected at t=0.0 min. (a) ACVs obtained at a microelectrode modified with peptide H-15. (b) ACVs obtained at a control microelectrode, which was passivated with mercaptohexanol/mercaptohexanoic acid and subsequently treated with an aqueous solution containing 0.20 g/l EDC and 0.20 g/l sulfo-NHS. (c) Proteolysis curves showing the relationship between $i_p$ vs. reaction time for the H-15 modified (red squares) and the passivated microelectrodes (black circles) shown in (a) and (b), respectively. The black line represents the exponential fit of the H-15 modified microelectrode using eq. 8. (d) Bar graph showing the fitted values of 1/τ for all of H-15 modified channels (CH 1-6) obtained simultaneously with the data shown in (a), (b) and (c).
FIG. 8 shows proteolysis data obtained on an Au MEA chip where CH 1-3 were modified with peptide H-16 (blue), CH 4-6 were modified with peptide H-15 (red), and CH 7-9 were modified with peptide H-3 (green). The experiment was performed in a solution containing 50 mM MES buffer (pH=5.0) and 6.0 nM cathepsin B. (a) Representative proteolysis curves and fitting lines for electrodes modified with H-16 (CH 1), H-15 (CH 4) and H-3 (CH 7). The data is normalized to the fitted values $i_{p0}$ derived from eq 9. (b) Bar graph showing the fitted values of 1/r for the channels modified with H-16 (CH 1-3), H-15 (CH 4-6), and H-3 (CH 7-9), respectively, and their average values at the far right with the standard deviation shown as the error bars.

FIG. 7 shows the results of proteolysis measurements obtained on an MEA where the electrodes were selectively functionalized with peptide H-15. First, the top two rows (CH 1-6) were modified by incubating the electrodes in an aqueous solution containing 1.0 mM mercaptohexanol and 0.2 mM mercaptohexanoic acid for 40 minutes to form a SAM with exposed hydroxyl and carboxyl terminal groups. Next, the SAM modified electrodes were incubated in an aqueous solution containing 0.20 g/l EDC, 0.20 g/l sulfo-NHS and 2.0 mM of the peptide-Fc substrate (H-15) for 2 hours to tether the peptide-Fc to the SAM. The bottom row (CH 7-9) was passivated by forming the SAM and then incubating the electrodes with a solution containing 0.20 g/l EDC, 0.20 g/l sulfo-NHS, but omitting the peptide-Fc substrate. FIGS. 7a and 7b show the baseline subtracted ACV traces for adjacent SAM/peptide-Fc modified (H-15, CH 4) and a SAM passivated (CH 7) electrodes obtained at various time points. These measurements were performed in a solution containing 25 mM MES buffer (pH=5.0). Immediately before t=0, a solution containing 6.0 nM cathepsin B was injected into the electrochemical cell. In FIG. 7a, the trace obtained at t=0.0 min shows a Gaussian-shaped peak with $i_p$=72.5 nA at −0.05 V vs. MSE. At t=4.9 min, $i_p$ has decreased to 60.3 nA but the peak position has not changed significantly. This observable decrease in $i_p$ occurs as a result of the cleavage and dissipation of peptide-Fc molecules caused by the proteolysis reaction. As t increases, $i_p$ continues to decrease until it reaches 20.0 nA at t=40.0 min. The value of $i_p$ further decreases beyond t=40.0 min.

FIG. 7b shows the control curves obtained on a passivated electrode without peptide-Fc functionalities (CH 7) as described above. These results were obtained simultaneously as the results shown in FIG. 7a. Here, at t=0.0 min, a small (11.9 nA) peak can be observed at −0.06 V vs. MSE. This peak is slightly larger than the background noise and likely due to a small amount of cross-contamination during the modification process. At t=10.9 min and later, no observable peak can be distinguished from the background signal.

Figure 16:
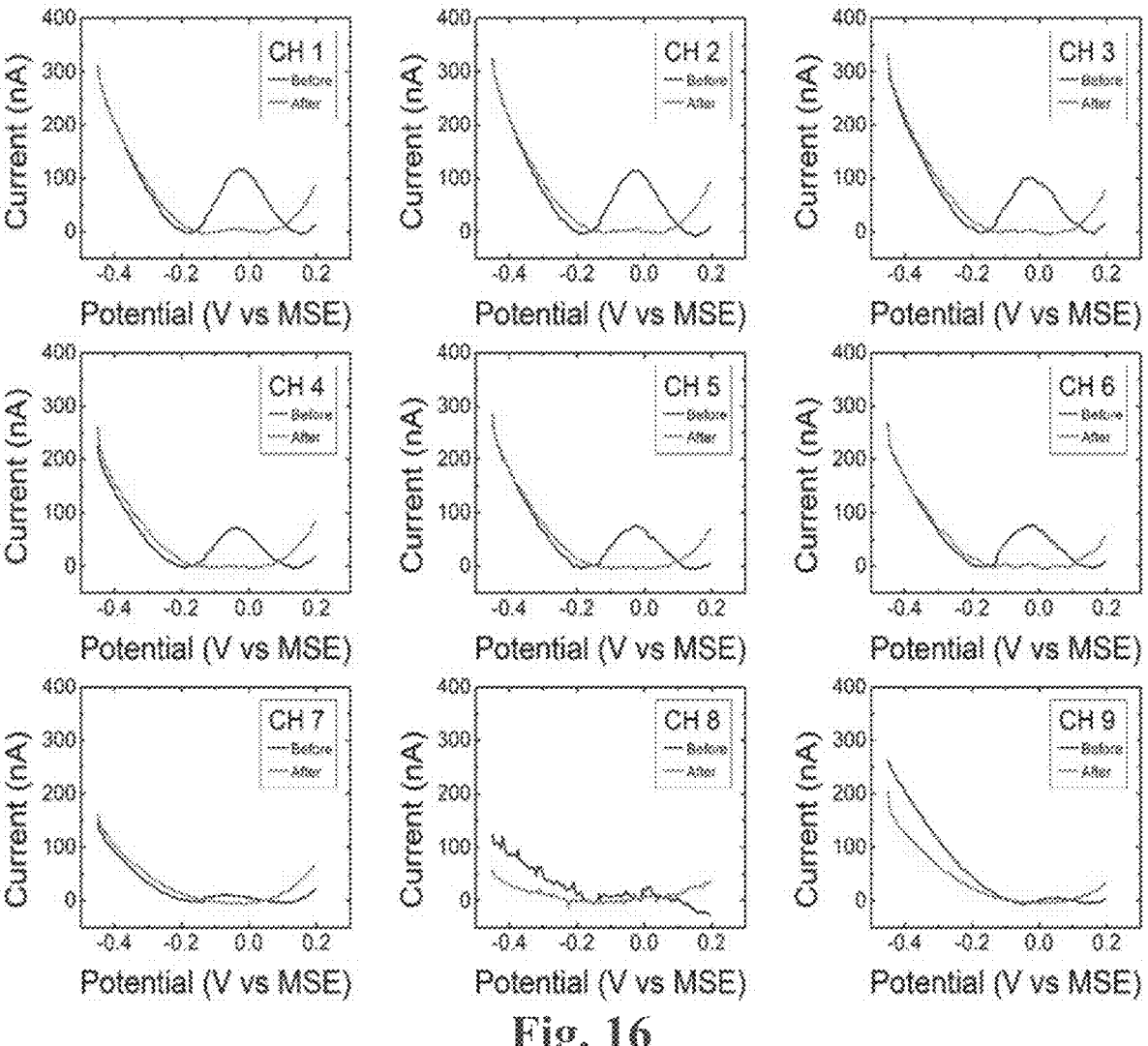
FIG. 16 shows ACVs obtained on a modified Au MEA. Channels 1-6 were modified peptide-Fc (H-15) by (i) incubating the electrodes in an aqueous solution containing 1.0 mM mercaptohexanol and 0.2 mM mercaptohexanoic acid for 40 minutes to form a SAM with exposed hydroxyl and carboxyl terminal groups and (ii) incubating the SAM modified electrodes with an aqueous solution containing 0.20 g/l EDC, 0.20 g/l sulfo-NHS and 2.0 mM of the peptide-Fc substrate for 2 hours to tether the peptide-Fc substrate (H-15) to the terminal ends of the alkanethiol SAM. Channels 7-9 are control electrodes which were prepared by forming the SAM in the same way as channels 1-6 and then incubated in an aqueous solution of 0.20 g/l EDC and 0.20 g/l sulfo-NHS without the presence of the peptide-Fc substrate. The black traces show the ACVs obtained during proteolysis with 6.0 nM cathepsin B at t=0.0 min and the red traces show the ACVs obtained at t=73.5 min.

For comparison, FIG. 16 shows ACV traces from all nine channels, which were simultaneously obtained during the experiment shown in FIG. 7. Each frame shows background subtracted ACV traces obtained before (t=0.0 min, black trace) and after (t=79.9 min, red trace) the proteolysis reaction. The traces are plotted on the same scale to highlight the differences between the six SAM/peptide modified electrodes (CH 1-6) and the three SAM modified electrodes (CH 7-9). The six SAM modified electrodes show a Gaussian peak corresponding to the presence of the peptide-Fc substrate bound to the electrode surface. The peak potential ($E_p$) varies slightly from channel to channel ($E_p$=−0.03±0.01 V vs. MSE), which is mainly due to variations in background subtraction. The average value of $i_p$ before proteolysis is 93.1±18.8 nA across all six of the SAM/peptide-Fc modified electrodes. The relatively small variation in $i_p$ is due to the differences in the surface density and conformation of the peptide-Fc tags on the electrode surfaces, which can change with the exposed carboxyl functionalities on the surface and the EDC/NHS coupling efficiency. After proteolysis, there is no obvious peak remaining and the average current at −0.03 V is 1.4β0 3.3 nA, which is within the noise of the measurements. In contrast, the value of $i_p$ measured on the passivated electrodes (CH 7-9) before and after proteolysis was 10.1±9.9 nA and 0.0±6.9 nA, respectively.

Figure 17:
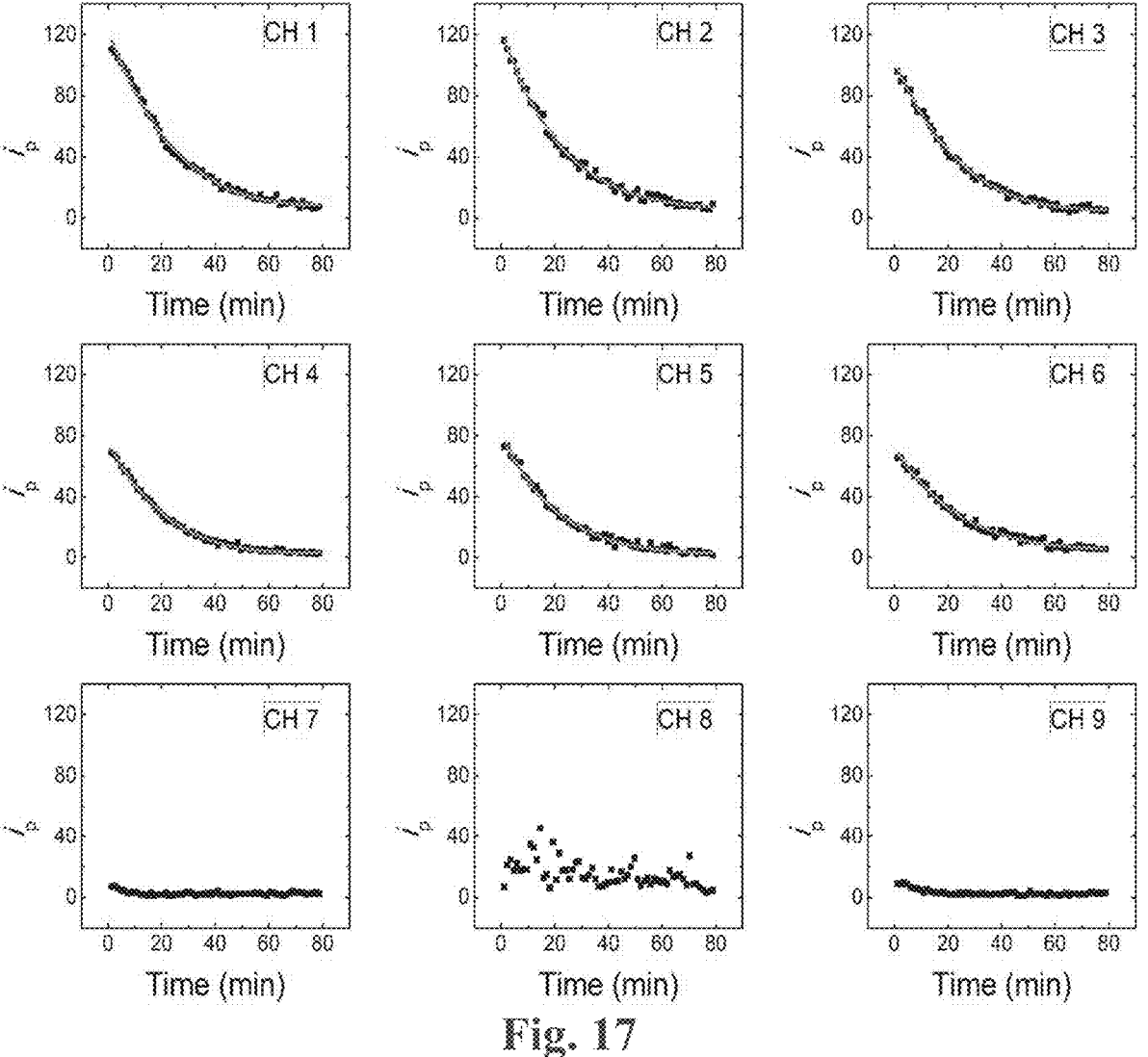
FIG. 17 shows proteolysis curves for the data above. The black squares represent the measured values of $i_p$ and the red lines shown for channels 1-6 are fitting curves to the experimental data. Channels 7-9 were not fitted because there is no clear exponential decay, as these electrodes were not treated with the peptide-Fc substrate. The first data point for each graph was omitted and excluded from the fitting as discussed in the Data Processing section.

FIG. 7c shows the proteolysis curves obtained from the data in FIGS. 7a and 7b. Here the red squares show the results obtained from an electrode, which has been functionalized with the peptide-Fc substrate H-15 (CH 4), and the black line corresponds to the exponential fit of that data. Here, the first data point is not plotted, and is not included in the exponential fit due to the presence of the interference peak as discussed above. The fit shows good agreement with the data ($R^2$=0.997) and the fitted value of $1/\tau$ is $6.84\times10^{-4}$ $s^{-1}$. FIG. 17 shows the proteolysis curves for all nine channels. Each peptide-Fc functionalized electrode (CH 1-6) shows a clear value of $i_p$ ranging from 65.5 nA to 116.0 nA at the beginning of the proteolysis reaction (t=1.2 min). Beyond t=1.2 min, $i_p$ shows a clear exponential decay. The red line shown in the frames corresponding to CH 1-6 are the exponential fits of the data for each channel. For each case, the fit shows good agreement ($R^2$>0.98) with the data. In contrast, CH 7-9 does not show any signs of exponential decay and, consequently, no fitting was performed.

FIG. 7d is a bar graph representing the measured values of $1/\tau$ for CH 1-6 along with the average and standard deviation across the six channels. The average value of $1/\tau$ is $(6.63±0.87)\times10^{-4}$ $s^{-1}$. All fitting parameters in eq 8 for each of the six peptide-Fc modified channels are shown in Table S2 along with the calculated value of $i_{p0}$ and the $R^2$ of each fit. These results demonstrate that the activity ($1/\tau$) can be determined reproducibly (RSD=0.13) and simultaneously on these selectively modified Au MEAs, and that the electrodes on the MEA can be selectively modified and clearly differentiated by ACV with minimal interference and cross-contamination between electrodes.

3.4 Multi-Peptide Measurements:

Single peptide measurements are adequate for quantification of single proteases. However, using different peptide-Fc substrates provide specificity for simultaneous detection of multiple proteases and will allow quantification of the activity profiles for these proteases, which offers enhanced capability for medical diagnosis and health monitoring involving complex samples. FIG. 8 shows a series of data obtained with multiple peptide-Fc substrates at once on a single MEA chip. For the experiments depicted here, the top row of electrodes (CH 1-3) are modified with peptide H-16, the middle row of electrodes (CH 4-6) are modified with peptide H-15, and the bottom row of electrodes (CH 7-9) are modified with peptide H-3.

Figure 18:
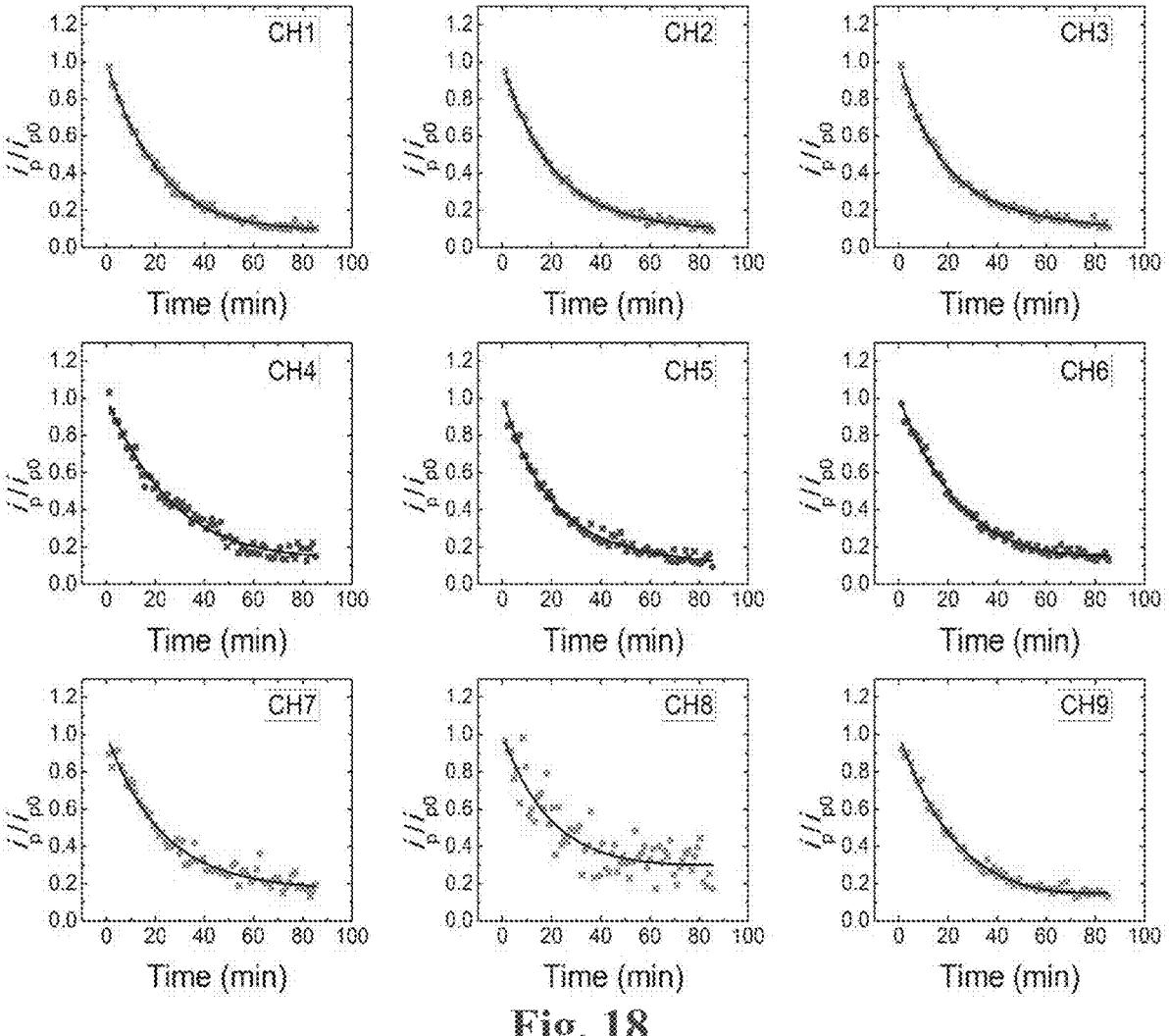
FIG. 18 shows proteolysis curves obtained with an Au MEA chip with the electrodes modified with peptide-Fc substrates H-16 (CH 1-3), H-15 (CH 4-6) and H-3 (CH 7-9).

FIG. 8a shows examples of proteolysis curves obtained on CH 1 (H-16, blue line), CH 4 (H-15, red line), and CH 7 (H-3, green line). Here, the data is normalized to the value of $i_{p0}$ derived from the fitting data according to eq 9. This normalization accounts for variations in I' of the peptide-Fc substrate between each of the electrodes, and the values of $i_{p0}$ and values of $i_{p0}$ are listed in Table S3. Each of these proteolysis curves shows a slightly different activity based on the observable rate of decay in $i_p$. FIG. 8b is a bar graph illustrating the differences in the measured values of $1/\tau$ broken down by channels with H-16 (shown in blue), H-15 (shown in red) and H-3 (shown in green), similar to FIG. 8a. Here the average values of $1/\tau$ were measured to be $(8.9±1.1)\times10^{-4}$ $s^{-1}$, $(6.8±1.8)\times10^{-4}$ $s^{-1}$, and $(7.4±0.9)\times10^{-4}$ $s^{-1}$ for H-16, H-15 and H-3, respectively. The proteolysis curves of each electrode are shown in FIG. 18 and the fitting results for each curve are shown in Table S3. These three peptides show similar values of $1/\tau$ because the majority of the amino acid sequences are similar. Cathepsin B was found to cleave peptide H-15 and H-16 between the Leu-Ala and Pro-Leu, respectively, while peptide H-3 was cleaved in two locations: between Gly-Ala and Phe-Gly residues as revealed by HPLC analyses (chromatograms not shown). For peptide H-15, all analyte solutions contained 6.5 mM peptide H-15, 50 mM MES buffer (pH 5.0) and 250 mM NaCl. Chromatograms of the peptide in the solution were then analyzed. H-15 appeared at 35.9 min in the chromatogram as verified by mass spectrometry. After incubation with cathepsin B for 2 h the cleaved fragment connected to the Fc moiety appeared at 16.0 min in the chromatogram as verified by mass spectrometry [showing a mass of 626.5 [M+23(Na)] in the mass spectrum]. A final chromatogram of peptide H-15 obtained after incubation with 5.75 ng/µL (0.17 µM) cathepsin B for 3 h confirms the cleavage site. Analyte solution for peptide H-16 was 50 mM MES (pH 5.0) and 250 mM NaCl. The hexapeptide appeared at 33.4 min in the HPLC chart and its structure was verified by mass spectrometry analysis. After treatment of hexapeptide H-16 with cathepsin B in 50 mM MES (pH 5.0) and 250 mM NaCl for 2 h the cleaved fragment appeared at 16.0 min and its structure was verified by MS analysis [showing a mass of 625.043 (M−H$_2$+1) in the mass spectrum]. Cleavage was confirmed by incubation of 6.5 mM peptide H-16 in 50 mM MES (pH 5.0) and 250 mM NaCl incubated with 5.75 ng/µl (0.17 µM) cathepsin B for 3 h.

4. Conclusions:

We have demonstrated rapid multiplex electrochemical detection of cathepsin B activities through fabrication of an individually addressed 3×3 Au MEA and systematic characterization. The MEAs were fabricated on 100 mm Si wafers containing 20 MEA chips, each 200 um×200 µm in size. The chip surface was protected with a 1-µm thick layer of SiO$_2$ with only the active electrode surface and the electrical contact areas exposed. Highly consistent signals among the nine microelectrodes have been obtained in electrochemical cleaning and electrochemical characterization with benchmark redox species. Selective functionalization of the Au microelectrode surface with specific Fc-labeled peptide molecules was achieved. The consistent proteolytic kinetics can be measured by monitoring the decay of the ACV signal of Fc as the peptide molecules are cleaved by cathepsin B. We further demonstrated the simultaneous detection of the proteolysis of cathepsin B on three specific hexapeptides on the same MEA, which can be used for rapid screening of potential peptide candidates. This study has established a sensor platform for future rapid detection of the activity profiles of multiple proteases towards cancer diagnosis.

Supporting Information

Design and Selection of Peptide-Fc Substrates for Cathepsin B

We have designed and synthesized nine different peptide-Fc substrates containing 6-8 amino acids (listed in Table S1 below) for proteolysis by cathepsin B based on the specific recognition reported in literature and tested the cathepsin B activities on these peptide-Fc substrates by the combination of electrochemical measurements (using Au disk electrodes and VACNF nanoelectrode arrays), fluorogenic assays and HPLC-MS analysis. Among them, three peptides H-3, H-15 and H-16 were selected for this study due to the higher proteolysis rates by cathepsin B compared to other candidates.

hexane and diethyl ether (1:1) to precipitate out the desired peptide. The solid peptide was collected by centrifugation (4000 rpm, 10 min, 4° C.) and washed three times with a cold solution of hexane and diethyl ether (1:1) to give the product peptide as a white solid. If the peptide was not sufficiently pure from HPLC analysis, either semi-preparative HPLC or silica gel column chromatography was used to purify the peptide.

TABLE SI

Nine peptide-Fc substrates screened for cathepsin B detection in this study.

| Peptide-Fc Substrates | Sequence | SEQ ID NO: |
|---|---|---|
| H-1 | $H_2N$-$(CH_2)_4$-CO-Lys-Val-Arg-Phe-Val-Gly-$NHCH_2$-Fc | 4 |
| H-2 | $H_2N$-$(CH_2)_4$-CO-Pro-Thr-Arg-Phe-Val-Gly-$NHCH_2$-Fc | 5 |
| H-3 | $H_2N$-$(CH_2)_4$-CO-Pro-Leu-Arg-Phe-Gly-Ala-$NHCH_2$-Fc | 1 |
| H-4 | $H_2N$-$(CH_2)_4$-CO-Pro-Val-Gly-Phe-Val-Ala-$NHCH_2$-Fc | 6 |
| H-5 | $H_2N$-$(CH_2)_4$-CO-Ala-Pro-Leu-Arg-Phe-Gly-Ala-Ala-$NHCH_2$-Fc | 7 |
| H-6 | $H_2N$-$(CH_2)_4$-CO-Pro-Leu-Gly-Phe-Val-Ala-$NHCH_2$-Fc | 8 |
| H-7 | $H_2N$-$(CH_2)_4$-CO-Pro-Leu-Gly-Gly-Val-Ala-$NHCH_2$-Fc | 9 |
| H-15 | $H_2N$-$(CH_2)_4$-CO-Pro-Leu-Ala-Phe-Val-Ala-$NHCH_2$-Fc | 2 |
| H-16 | $H_2N(CH_2)_4$CO-Pro-Leu-Ala-Gly-Val-Ala-$NHCH_2$-Fc | 3 |

Peptide Synthesis and Characterization

Figure 12:
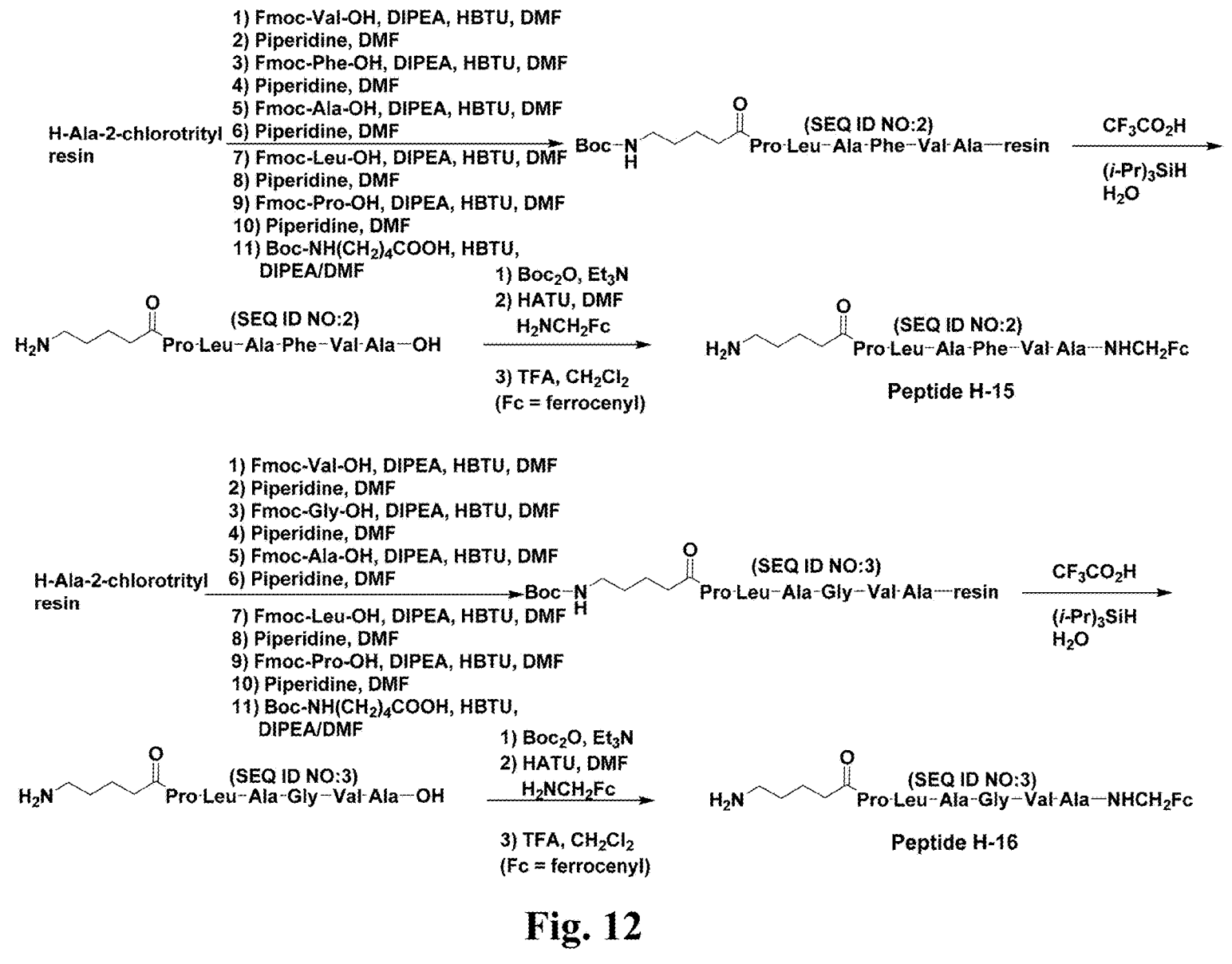

Peptide synthesis was performed by a solid-phase peptide method using a CEM Discover microwave synthesizer and the procedure is depicted in FIG. 12. Peptide H-3 was prepared using a previously reported method.

a. Standard Coupling Procedure Using Microwave

A solution of N-fluorenylmethyloxycarbonyl-amino acid (N-Fmoc-amino acid) (1.35 mmol, 3.0 equiv.) and 2-(1H-benzotriazol-1-yl)-1,1,3,3-tetramethyluronium hexafluorophosphate (HBTU) (1.22 mmol, 2.7 equiv.) in dry DMF (16 ml) containing 4.2% diisopropylethylamine (DIPEA) was added to 1.0 g (0.45 mmol) of H-Ala-2-chlorotrityl Resin (1% DVB, 100-200 mesh resin, 1.0 equiv.). The mixture was subjected to microwave irradiation (25 W, 5 min, 75° C.) with stirring. The reaction mixture was filtered and washed five times with 10 ml of DMF. For amino acids containing bulky side chains, the aforementioned coupling reaction was repeated until the coupling reaction was completed, indicated by the absence of amine (primary) in the peptide-attached resin from a ninhydrin test.

b. Standard Deprotection Procedure Using Microwave

A solution of 20% piperidine in DMF (16 ml) was added to the N-Fmoc protected amino acid resin and subjected to microwave irradiation (25 W, 3 min, 75° C.). The reaction mixture was filtered, and the resin was washed five time with 10 ml DMF.

c. Standard Cleavage Procedure Using Microwave

The peptide attached 2-chlorotrityl resin was washed with 20 ml dichloromethane (DCM) and then treated with 16 ml of a cleavage solution consisting of 95% trifluoroacetic acid (TFA), 2.5% triisopropylsilane (TIPS), and 2.5% water. The reaction mixture was irradiated in the microwave reactor (20 W, 38° C.) for 18 min. The reaction mixture was filtered into a 100-ml flask and diluted with 60 ml of a cold solution of Preparation of Peptide H-15:

Starting from 1.0 g (0.45 mmol) of H-Ala-2-chlorotrityl resin (200 mesh), the following reaction sequence was carried out: (i) coupling with N-Fmoc-Val-OH (1.35 mmol) and HBTU (2.7 equiv., for all amino acid coupling steps); (ii) deprotection of Fmoc group with piperidine in DMF; (iii) coupling with N-Fmoc-Phe-OH (1.35 mmol); (iv) deprotection with piperidine/DMF; (v) coupling with N-Fmoc-Ala-OH (1.35 mmol); (vi) deprotection with piperidine/DMF; (vii) coupling with N-Fmoc-Leu-OH (1.35 mmol); (viii) deprotection with piperidine/DMF; (ix) coupling with N-Fmoc-Pro-OH (1.35 mmol); (x) deprotection with piperidine/DMF; (xi) coupling with N-(tert-butoxycarbonyl)-$NH(CH_2)_4CO_2H$ [or N-Boc-$NH(CH_2)_4CO_2H$] (1.35 mmol) with HBTU (2 equiv.); and (xii) cleavage of the peptide from resin with TFA and $(i-Pr)_3SiH$ in water. The peptide was then precipitated out using a mixture of hexane and diethyl ether, and dried to yield 310 mg of $H_2N(CH_2)_4$ CO-Pro-Leu-Ala-Phe-Val-Ala-OH (SEQ ID NO:2). This material was used in the subsequent reaction without further purification.

To a solution of 0.14 g (0.20 mmol) of $H_2N(CH_2)_4CO$-Pro-Leu-Ala-Phe-Val-Ala-OH (SEQ ID NO:2) in 10 ml of p-dioxane and water (1:1) were added 75 μl (0.60 mmol) of triethylamine and 0.128 g (0.60 mmol) of di-tert-butyl dicarbonate ($Boc_2O$). The solution was stirred at room temperature for 12 h, and additional 50 μl of triethylamine and 95 mg of $Boc_2O$ were added. It was stirred for 8 h and HPLC-MS analysis of an aliquot of the solution showed the absence of starting material peptide and only the presence of desired peptide. The solution was concentrated under reduced pressure for 3 h to give the Boc protected crude product, which was used without purification in the following reaction. To the aforementioned N-Boc-$HN(CH_2)_4CO$-Pro-Leu-Ala-Phe-Val-Ala-OH (SEQ ID NO:2) and 0.11 g (0.28 mmol) of 1-[bis(dimethylamino)methylene]-1H-1,2,3- triazolo[4,5-b]pyridinium 3-oxide hexafluorophosphate (HATU) in 1 ml of DMF was added a solution of 60 mg (0.24 mmol) of 1-(aminomethyl)ferrocene-HCl salt in 1 ml of DMF. The solution was stirred at 25° C. for 12 h and an aliquot was analyzed by HPLC showing the absence of starting peptide. The reaction mixture was filtered through a Chromafil Xtra PTFE-20/25 syringe filter (0.20 μm) and the filtrate was purified by preparative HPLC using water and acetonitrile (1:1; 10 ml/min) as the running solvent to give 0.10 g of N-Boc-HN(CH$_2$)$_4$CO-Pro-Leu-Ala-Phe-Val-Ala-NHCH$_2$-Fc (Fc=ferrocenyl) (SEQ ID NO:2). MS (ESI; positive mode): m/z calculated for C$_{52}$H$_{77}$FeN$_8$O$_9$ (M+H)$^+$: 1013.51, found 1013.37 (100%).

Peptide H-15: H$_2$N(CH$_2$)$_4$CO-Pro-Leu-Ala-Phe-Val-Ala-NHCH$_2$-Fc (SEQ ID NO:2). To a solution of 0.10 g of N-Boc-HN(CH$_2$)$_4$CO-Pro-Leu-Ala-Phe-Val-Ala-NHCH$_2$-Fc (SEQ ID NO:2) in 10 ml of dichloromethane was added 1 ml of TFA, and the solution was stirred at 25° C. for 30 min. An aliquot was removed and analyzed by TLC, showing the absence of the starting peptide. The reaction mixture was diluted with 15 ml of water and concentrated on a rotary evaporator to remove most of the dichloromethane and TFA, leaving a mixture of solid and liquid. The yellow solid was collected by filtration to give 85 mg (86% yield) of peptide H-15 with attached ferrocene redox moiety. MS (ESI; positive mode): m/z calculated for C$_{47}$H$_{69}$FeN$_8$O$_7$ (M+H)$^+$: 913.46, found 913.34 (100%). $^1$H NMR (400 MHz, DMSO-D$_6$) δ 8.2-7.5 (a series of m, 6H, NHC=O), 7.25-5.15 (m, 5H, Ar), 4.6-4.48 (m, 1H), 4.48-4.24 (m, 2H, NCH$_2$-Fc), 4.15 (s, 5H, Cp ring of Fc), 4.07 (s, 2H, Cp ring of Fc), 4.02-3.95 (m, 2H, Cp ring of Fc), 3.10-2.95 (m, 1H), 2.75-1.27 (a series of m), 1.23 (d, J=7 Hz, 3H, Me), 1.15 (d, J=7 Hz, 3H, Me), 0.80-0.75 (a series of 4 d, 12H, 4 Me's of 2 isopropyl groups) ppm. $^{13}$C NMR (100 MHz, DMSO-D$_6$) δ 172.4, 171.9, 171.2, 171.0, 170.7, 138.1, 129.7 (2C), 128.5 (2C), 126.7, 68.9 (Cp's Cs of ferrocene), 67.8 (Cp's Cs of ferrocene), 59.8, 57.9, 51.4, 48.5, 47.3, 37.9, 33.5, 31.2, 29.8, 27.2, 24.6, 23.6, 22.7, 21.9, 21.4, 19.7, 18.9, 18.5 ppm.

Preparation of Peptide H-16:

Starting from 1.0 g (0.45 mmol) of H-Ala-2-chlorotrityl resin (200 mesh), the following reaction sequence was carried out: (i) coupling with N-Fmoc-Val-OH (1.35 mmol) and HBTU (2.7 equiv., for all amino acid coupling steps); (ii) deprotection of Fmoc group with piperidine in DMF; (iii) coupling with N-Fmoc-Gly-OH (1.35 mmol); (iv) deprotection with piperidine/DMF; (v) coupling with N-Fmoc-Ala-OH (1.35 mmol); (vi) deprotection with piperidine/DMF; (vii) coupling with N-Fmoc-Leu-OH (1.35 mmol); (viii) deprotection with piperidine/DMF; (ix) coupling with N-Fmoc-Pro-OH (1.35 mmol); (x) deprotection with piperidine/DMF; (xi) coupling with N-Fmoc-NH(CH$_2$)$_4$CO$_2$H (1.35 mmol); and (xii) cleavage of the peptide from resin with TFA and (i-Pr)$_3$SiH in water. After precipitation of the peptide using a mixture of hexane and diethyl ether and drying, 164 mg of H$_2$N(CH$_2$)$_4$CO-Pro-Leu-Ala-Gly-Val-Ala-OH (SEQ ID NO:3) was obtained. This material was used in the subsequent reaction without further purification.

To a solution of 0.83 g (0.13 mmol) of H$_2$N(CH$_2$)$_4$CO-Pro-Leu-Ala-Gly-Val-Ala-OH (SEQ ID NO:3) in 10 ml of p-dioxane and water (1:1) were added 52 μl (0.40 mmol) of triethylamine and 0.087 g (0.40 mmol) of di-tert-butyl dicarbonate (Boc$_2$O). The solution was stirred at room temperature for 12 h, and additional 40 μl of triethylamine and 45 mg of Boc$_2$O were added. It was stirred for 8 h and HPLC-MS analysis of an aliquot of the reaction solution showed the absence of the starting amine. The reaction solution was concentrated under reduced pressure for 3 h to give the Boc protected crude product. It was used in the following step without purification. To the aforementioned N-Boc-HN(CH$_2$)$_4$CO-Pro-Leu-Ala-Gly-Val-Ala-OH (SEQ ID NO:3) and 66 mg (0.17 mmol) of HATU in 1 ml of DMF was added a solution of 37 mg (0.15 mmol) of 1-(aminomethyl)ferrocene-HCl salt in 1 ml of DMF. The solution was stirred at 25° C. for 12 h and an aliquot was analyzed by HPLC showing the absence of the starting peptide. The reaction mixture was filtered through a Chromafil® Xtra PTFE-20/25 syringe filter (0.20 μm) and the filtrate was purified by preparative HPLC using water and acetonitrile (1:1; 10 ml/min) as the running solvent to give N-Boc-HN (CH$_2$)$_4$CO-Pro-Leu-Ala-Gly-Val-Ala-NHCH$_2$-Fc (SEQ ID NO:3) (Fc=ferrocenyl).

Peptide H-16: H$_2$N(CH$_2$)$_4$CO-Pro-Leu-Ala-Gly-Val-Ala-NHCH$_2$-Fc (SEQ ID NO:3). To a solution of 40 mg of N-Boc-HN(CH$_2$)$_4$CO-Pro-Leu-Ala-Gly-Val-Ala-NHCH$_2$-Fc (SEQ ID NO:3) in 5 ml of dichloromethane was added 0.5 ml of TFA, and the solution was stirred at 25° C. for 30 min. An aliquot was removed and analyzed by TLC, showing the absence of the starting peptide. The reaction mixture was diluted with 10 ml of deionized water and concentrated on a rotary evaporator to remove most of the dichloromethane and TFA. The resulting solution was diluted with deionized water and lyophilized on a freeze-dry instrument to give 30 mg of peptide H-16 with attached ferrocene redox moiety. MS (ESI; positive mode): m/z calcd for C$_{40}$H$_{63}$FeN$_8$O$_7$ (M+H)$^+$: 823.409, found 823.303 (100%). $^1$H NMR (400 MHz, D$_2$O) δ 4.4-4.25 (m, 9H, Cp's Hs of Fc), 3.91 (s, 1H), 3.84-3.82 (m, 1H), 3.66-3.58 (m, 2H), 3.04-2.93 (m, 6H), 2.50-2.44 (m, 2H), 2.10-1.80 (m, 4H), 1.78-1.56 (m, 10H), 1.47 (d, J=8 Hz, 2H), 1.39 (d, J=8 Hz, 2H), 1.02-0.75 (a series of d, 18H) ppm. $^{13}$C NMR (100 MHz, D$_2$O) δ 174.7 (3C), 174.5 (4C), 60.1 (Cp's Cs of ferrocene, 5C), 58.6 (Cp's Cs of ferrocene, 5C), 54.0, 52.2, 49.7, 48.0, 42.1, 39.5, 39.1 (2C), 38.2, 33.2, 29.6, 26.3, 24.4 (2C), 22.1, 21.0, 20.6, 18.2, 18.1, 17.6, 17.4, 17.3, 16.5 ppm.

TABLE S2

Fit results for SAM/peptide-Fc (H-15) modified Au MEA (channels 1-6) in FIG. 7 and FIGS. 16-17.

| Channel | 1/τ ×10$^{-4}$ (s$^{-1}$) | a (nA) | b (nA s$^{-1}$) | c (nA) | i$_{p0}$ (nA) | R$^2$ |
|---|---|---|---|---|---|---|
| 1 | 5.50 | 154.3 | 0.374 | −32.4 | 121.9 | 0.995 |
| 2 | 7.34 | 125.1 | 0.058 | −1.3 | 123.8 | 0.995 |
| 3 | 5.88 | 127.6 | 0.287 | −24.8 | 102.8 | 0.995 |
| 4 | 6.84 | 89.0 | 0.169 | −13.3 | 75.7 | 0.997 |
| 5 | 7.79 | 83.8 | 0.044 | −2.3 | 81.5 | 0.992 |
| 6 | 6.45 | 75.8 | 0.079 | −3.8 | 72.0 | 0.989 |
| Avg | 6.63 | 109.3 | 0.169 | −13.0 | 96.3 | |
| St Dev | 0.87 | 31.0 | 0.136 | 13.0 | 23.2 | |

TABLE S3

Fit results for SAM/peptide-Fc modified Au MEA in FIG. 8 and FIG. 18.

| Peptide | Channel | 1/τ (s$^{-1}$) | a (nA) | b (nA s$^{-1}$) | c (nA) | i$_{p0}$ (nA) | R$^2$ |
|---|---|---|---|---|---|---|---|
| H16 | 1 | 7.83 | 308.1 | 0.08 | 20.8 | 308.1 | 0.996 |
| | 2 | 8.88 | 347.2 | −0.26 | 62.3 | 347.2 | 0.996 |
| | 3 | 10.00 | 248.6 | −0.38 | 67.9 | 248.6 | 0.995 |
| | AVG | 8.90 | 301.3 | −0.18 | 50.3 | 301.3 | |
| | St Dev | 1.08 | 49.7 | 0.24 | 25.7 | 49.7 | |

TABLE S3-continued

| | | Fit results for SAM/peptide-Fc modified Au MEA in FIG. 8 and FIG. 18. | | | | | |
|---|---|---|---|---|---|---|---|
| Peptide | Channel | $1/\tau$ (s$^{-1}$) | a (nA) | b (nA s$^{-1}$) | c (nA) | $i_{p0}$ (nA) | R$^2$ |
| H15 | 4 | 5.82 | 149.7 | 0.13 | 5.6 | 149.7 | 0.975 |
| | 5 | 8.89 | 146.4 | −0.15 | 33.9 | 146.4 | 0.986 |
| | 6 | 5.66 | 222.9 | 0.48 | −22.5 | 222.9 | 0.986 |
| | AVG | 6.79 | 173.0 | 0.15 | 5.7 | 173.0 | |
| | St Dev | 1.82 | 43.2 | 0.32 | 28.2 | 43.2 | |
| H3 | 7 | 7.34 | 68.6 | 0.00 | 14.1 | 68.6 | 0.965 |
| | 8 | 8.26 | 100.3 | 0.06 | 33.2 | 100.3 | 0.776 |
| | 9 | 6.48 | 116.4 | 0.21 | −5.0 | 116.4 | 0.991 |
| | AVG | 7.36 | 95.1 | 0.09 | 14.1 | 95.1 | |
| | St Dev | 0.89 | 24.3 | 0.11 | 19.1 | 24.3 | |

Determination of Cleavage Sites by HPLC-MS

The cleavage sites of the hexapeptide-Fc substrates were examined using HPLC as described above. Analytical HPLC was performed with a Shimadzu SCL-10A HPLC system fitted with a proto 300 C18 reverse phase semi-prep column (10 μm, 250×10 mm). The flow rate was 1 ml/min with a gradient elution starting from 100% solvent A (water containing 0.1% TFA) to 20% solvent A and 80% solvent B (acetonitrile containing 0.1% TFA) over 50 min. The UV absorbance was monitored at 254 nm. The HPLC chromatogram of peptide H-15 (with attached ferrocene redox moiety) in 50 mM MES (pH 5.0) and 250 mM NaCl appeared at 35.9 min in the chromatogram (not shown) and its structure was verified by mass spectrometry analysis. Chromatograms after peptide H-15 was treated with cathepsin B for 2 h and 3 h, respectively confirmed the cleavage product, Ala-Phe-Val-Ala-NHCH$_2$-Fc (residues 3-6 of SEQ ID NO:2) (mass of 603.5+23 of sodium$^+$=626.5) appeared at 16.0 min in the chromatogram and its structure was verified by MS analysis. A mass of 626.2 was found from the peak at 16.0 min. Similarly, the HPLC chromatogram of 6.5 mM peptide H-16 (with attached ferrocene redox moiety) in 50 mM MES (pH 5.0) and 250 mM NaCl verified the initial show chromatograms obtained after peptide H-16 was incubated with 5.75 ng/μL (0.17 μM) cathepsin B for 2 h and 3 h, respectively. The absorbance peak at ~33.5 min was peptide H-16 and peak at 16.0 min is assigned as [Leu-Ala-Gly-Val-Ala-NH=CH-Fc]$^+$ (residues 2-6 of SEQ ID NO:3) (mass of 625.288).

Based on the observed mass of 625.043 found in the mass spectrum of this 33.5-min. peak, it is proposed to derive from a loss of H$_2$ (from beta-elimination of the NH and CH$_2$-Fc) following protonation by H$^+$. Based on these results, we conclude that cathepsin B cleaves peptide H-15 between Leu-Ala and peptide H-16 between Pro-Leu. Previously, cathepsin B was found to cleave peptide H-3 in two places: between the Gly-Ala residues and between the Phe-Gly residues.

Example 2

Design, Synthesis, and Electrochemical Evaluation of Substrate Peptides for Profiling of Proteases This example describes peptide synthesis using solution phase synthesis instead of the solid-phase synthesis using microwave peptide synthesizer. Synthetic intermediates in each step can be isolated in very good yields and they can be used to prepare a library of peptides by changing the amino acid residues. Moreover, the reactions can be scaled up to gram scales, such as 10-100 grams.

| Substrate peptide | Target Protease | Peptide Sequence | MW | SEQ ID NO: |
|---|---|---|---|---|
| 1 | Cathepsin B | H$_2$N-(CH$_2$)$_4$-CO-*Leu-Arg-Phe-Gly*-NH-CH$_2$-Fc | 787.8 | residues 2-5 of 1 |
| 2 | Cathepsin B | H$_2$N-(CH$_2$)$_4$-CO-*Lys-Val-Arg-Phe-Val-Gly*-NH-CH$_2$-Fc | 1000.5 | 4 |
| 3 | Cathepsin B | H$_2$N-(CH$_2$)$_4$-CO-*Pro-Leu-Arg-Phe-Gly-Ala*-NH-CH$_2$-Fc | 995.5 | 1 |
| 4 | Cathepsin B | H$_2$N-(CH$_2$)$_4$-CO-*Pro-Val-Gly-Phe-Val-Ala*-NH-CH$_2$-Fc | 884.4 | 6 |
| 5 | Cathepsin B | H$_2$N-(CH$_2$)$_4$-CO-*Ala-Pro-Leu-Arg-Phe-Gly-Ala-Ala*-NH-CH$_2$-Fc | 1097.5 | 7 |
| 6 | Cathepsin B | H$_2$N-(CH$_2$)$_4$-CO-*Pro-Leu-Gly-Phe-Val-Ala*-NH-CH$_2$-Fc | 898.4 | 8 |
| 7 | Cathepsin B | H$_2$N-(CH$_2$)$_4$-CO-*Pro-Leu-Gly-Gly-Val-Ala*-NH-CH$_2$-Fc | 808.4 | 9 |
| 8 | ADAM-10 | H$_2$N-(CH$_2$)$_4$-CO-*Phe-Leu-Met-Gln-Val-Ala*-NH-CH$_2$-Fc | 1003.5 | 10 |
| 9 | ADAM-10 | H-*Pro-Leu-Gly-Leu*-OH | 398.3 | residues 2-5 of SEQ 11 |
| 10 | ADAM-10 | H-*Pro-Leu-Gly-Leu-Ser-Ala*-OH | 572.4 | residues 2-7 of SEQ 11 |
| 11 | ADAM-10 | H-*Pro-Leu-Gly-Leu-Ser-Ala-Arg*-NH$_2$ | 711.4 | residues 2-8 of SEQ 11 |

-continued

| Substrate peptide | Target Protease | Peptide Sequence | MW | SEQ ID NO: |
|---|---|---|---|---|
| 12 | ADAM-10 | H-Lys-Pro-Leu-Gly-Leu-Ser-Ala-Arg-NH$_2$ | 839.5 | 11 |
| 13 | ADAM-10 | H-Lys-Pro-Leu-Gly-Leu-Ser-Ala-Arg-OH | 840.5 | 11 |
| 14 | ADAM-17 | H$_2$N-(CH$_2$)$_4$-CO-Lys-Pro-Leu-Gly-Leu-Ser-Ala-Arg-NH-CH$_2$-Fc | 1136.6 | 11 |
| 15 | Cathepsin B | H$_2$N-(CH$_2$)$_4$-CO-Pro-Leu-Ala-Phe-Val-Ala-NH-CH$_2$-Fc | 912.5 | 2 |
| 16 | Cathepsin B | H$_2$N-(CH$_2$)$_4$-CO-Pro-Leu-Ala-Gly-Val-Ala-NH-CH$_2$-Fc | 822.4 | 3 |
| 17 | ADAM-17 | H$_2$N-(CH$_2$)$_4$-CO-Leu-Gly-Leu-Ser-Ala-Arg-NH-CH$_2$-Fc | 911.5 | residues 3-8 of SEQ 11 |
| 18 | Cathepsin D | H$_2$N-(CH$_2$)$_4$-CO-Pro-Leu-Gly-Leu-Phe-Ala-Arg-NH-CH$_2$-Fc | 1068 | 12 |
| 19 | ADAM-17 | H$_2$N(CH$_2$)$_4$-CO-Ala-Gly-Leu-Phe-Ala-Arg-NH-CH$_2$-Fc | 869.9 | 13 |
| 20 | ADAM-17 | H$_2$N(CH$_2$)$_4$-CO-Ala-Gly-Leu-Phe-Leu-Arg-NH-CH$_2$-Fc | 972.0 | 14 |
| 21 | Cathepsin D | H$_2$N-(CH$_2$)$_4$-CO-Pro-Leu-Gly-Leu-Ala-Arg-NH-CH$_2$-Fc | 921.9 | 15 |
| 22 | Cathepsin D | H$_2$N-(CH$_2$)$_4$-CO-Pro-Phe-Leu-Gly-Ala-Arg-NH-CH$_2$-Fc | 956.0 | 16 |
| 23 | MMP-9 | H$_2$N(CH$_2$)$_4$-CO-Pro-Arg-Phe-Ile-Ser-Ala-NH-CH$_2$-Fc | 986.0 | 17 |
| 24 | MMP-9 | H$_2$N(CH$_2$)$_4$-CO-Pro-Arg-Thr-Phe-Ser-Ala-NH-CH$_2$-Fc | 973.9 | 18 |
| 25 | MMP-9 | H$_2$N(CH$_2$)$_4$-CO-Pro-Arg-Thr-Ile-Phe-Ala-NH-CH$_2$-Fc | 1000.0 | 19 |
| 26 | MMP-9 | H2N(CH$_2$)$_4$-CO-Pro-Arg-Thr-Ile-Ser-Ala-NH-CH$_2$-Fc | 939.9 | 20 |
| 27 | MMP-9 | H$_2$N(CH$_2$)$_4$-CO-Pro-Phe-Thr-Ile-Ser-Ala-NH-CH$_2$-Fc | 930.9 | 21 |

Solution Phase Synthesis of Substrate Peptides:

The synthesis of peptide 26 using a solution phase methodology is illustrated in the Reaction Scheme in FIG. 19, as a representative example. Hence, (aminomethyl)ferrocene (1) was condensed with Fmoc-Ala-OH, HBTU [2-(1H-benzotriazol-1-yl)-1,1,3,3-tetramethyluronium hexafluorophosphate] and triethylamine in a mixture of dichloromethane and N,N-dimethylformamide (DMF) at room temperature to give amide 2 in an excellent yield. The Fmoc protecting group of 2 was removed by the treatment with piperidine in dichloromethane followed by condensation with Fmoc-Ser-OH using the same protocol as described above to give dipeptide 3. Similar sequence of deprotection and condensation processes were applied to dipeptide 3 sequentially by using different Fmoc-protected amino acids, such as Fmoc-Ile-OH, Fmoc-Thr-OH, Fmoc-Arg(Pbf)OH, and Fmoc-Pro-OH to give compound hexapeptide 7. Removal of the Fmoc group of peptide 7 with piperidine followed by coupling with linker Boc-NH—(CH$_2$)$_4$—CO$_2$H and HBTU, and deprotection of the Fmoc and Pbf groups with trifluoroacetic acid (TFA) in dichloromethane gives peptide 26.

This method provides various mono-, di-, tri-, tetra-, and penta-peptide intermediates. They can be used to prepare a library of peptides. For example, coupling of peptide 5 with Fmoc-Phe-OH followed by Fmoc-Pro-OH produces peptide 27. And, coupling of peptide 4 with Fmoc-Phe-OH, Fmoc-Arg(Pbf)-OH, and Fmoc-Pro-OH gives peptide 23.

Example 3

Detection of Proteases in Human Serum at Physiologic pH

This study demonstrates an activity-based electrochemical biosensor of a 3×3 gold MEA for the detection of cathepsin B activity in human serum diluted in a newly developed physiology-compatible neutral buffer. Proteolysis of ferrocene-labeled peptide substrates functionalized on 200×200 um microelectrodes is measured simultaneously over the 9 channels by AC voltammetry using similar protocols reported for Example 1 above. The protease activity is represented by the inverse of the exponential decay time constant ($1/\tau$), which equals to ($k_{cat}/K_M$)[CB] based on the Michaelis-Menten model. An enhanced activity of the recombinant human cathepsin B (rhCB) is observed in a newly developed low-ionic-strength phosphate buffer at pH=7.4, resulting in a very low limit of detection of $8.49\times 10^{-4}$ s$^{-1}$ for activity and 57.1 pM for active rhCB concentration that is comparable to affinity-based ELISA measurements. The cathepsin B presented in the human serum sample is validated by ELISA, which mainly detects the inactive proenzyme, while the electrochemical biosensor specifically measures the active cathepsin B and shows significantly higher decay rates when rhCB and human serum are activated. Analyses of the kinetic electrochemical measurements with spiked active cathepsin B in human serum provide further assessment of the protease activity in the complex sample.

This data establishes detection in a low-salt-concentration phosphate buffer with a pH value comparable to human serum and demonstration of the ability to detect very low concentration (down to 57 pM) of activated protease in complex human serum samples. Establishing a physiology-compatible neutral buffer (pH=~7.4) enables detection of the activity of all extracellular proteases present in the human buffer, instead of doing it separately after transferring into different buffers. This allows cancer diagnosis directly using blood or serum samples. This study lays the foundation to develop the gold MEA into a multiplex biosensor for rapid detection of the activity of extracellular proteases towards cancer diagnosis and treatment assessment. Further, the activity of cathepsinB in the new buffer (0.5×PB) in the electrochemical method was unexpectedly increased by about 40 times than in previous MES buffer (pH=5.0) used in Example 1. This is indicated by 40 times faster exponential decay in the measured proteolysis curve. Thus, the LOD was lowered by about one order of magnitude, being comparable to the gold standard highly sensitive biosensing method based on ELISA.

EXPERIMENTAL SECTION

The details of the used materials, chemicals, reagents and instruments are described in the Supporting Information (SI). Only two critical biological reagents are described here: (1) carrier-free recombinant human cathepsin B (rhCB) (~60% 37 kDa proenzyme and ~40% 29 kDa mature enzyme) from R&D Systems Inc. (Minneapolis, MN) was used as a surrogate human cathepsin B for demonstrating the activity detection, (2) a "pooled human serum off the clot" (catalog no. ISER10ML, Innovative Research, Novi, MI) was used to validate the detection of extracellular cathepsin B. This HS sample was a whole blood derived by allowing the blood to clot and then processed into serum via centrifugation. The sample was frozen immediately after processing by the vendor. The received HS sample was stored in −80° C. freezer in aliquots and only a small aliquot was taken out and used in each experiment.

Fabrication of the Au MEA chip. The procedure to fabricate the Au MEA follows Example 1. Briefly, the Au MEA chip was fabricated on a thermally oxidized 4" Si(100) wafer. A stack of Ti/Au/Ti films was then deposited on the SiO$_2$/Si wafer sequentially. A positive photoresist film was coated and patterned through a photomask. The exposed Ti/Au/Ti was etched by a combination of HF/H$_2$O solution and Transene TFA Au etchant. Only the microelectrodes (200 um×200 um) in the 3×3 MEA, the 9 electrical contact pads (1 mm×1 mm) and connection lines between them were protected by the unexposed photoresist and thus preserved in the etching process. After stripping the photoresist, the whole chip was deposited with a 1-um SiO$_2$ layer followed by the second positive photolithography and reactive ion etching to expose the 3×3 microelectrodes and the 9 contact pads. Finally, the top Ti layer in the MEA was etched with HF/H$_2$O solution to expose the clean Au substrate surface of each microelectrode and the 9 contact pads. FIG. 1 illustrates the structure and layout of the whole 4" SiO$_2$/Si wafer consisting of 21 individual Au MWA chips. The edge-to-edge spacing (s) or distance of adjacent microelectrodes was set at 1 mm to ensure enough space between each microelectrode for spotting reagents on each microelectrode during peptide functionalization while avoiding cross contaminations.

Gold MEA Functionalization. The diced Au MEA chip was sonicated in acetone for 5 min to remove the photoresist protection layer, followed by rinsing with methanol and subsequently with isopropanol for 30 seconds. The Au MEA was then rinsed with deionized water and blow-dried with N$_2$. Prior to use, the Au MEA chip was mounted in a home-made electrochemical cell described in our previous report and electrochemically cleaned by cycling voltammetry (CV) between −0.60 to 0.70 V in 0.10 M phosphate buffer (0.038 M NaH$_2$PO$_4$ and 0.061 M Na$_2$HPO$_4$, pH=7.4) vs. a mercury/mercurous sulfate reference electrode (MSE) filled with a saturated K$_2$SO$_4$ solution (CH Instruments, Austin, TX). The cleaned Au MEA was then rinsed with deionized water and blow-dried with N$_2$. All electrochemical protease detection measurements in this study used an in-house synthesized hexapeptide H-15 attached with a ferrocene (Fc) redox tag, as the substrate (referred to as "peptide-Fc" in this study). This peptide substrate was selected from about 30 synthesized peptides (same as H-15 in Example 1) and has shown the highest proteolytic activity by cathepsin B. It was specifically cleaved by cathepsin B between Leu and Ala residues as determined by HPLC-MS. To functionalize the MEA with this peptide-Fc substrate, the chip was first incubated in 1.0 mM 6-mercapto-1-hexanol mixed with 0.2 mM 6-mercapto-1-hexanoic acid in deionized water for 40 min to form a close-packed self-assembled monolayer (SAM) due to thiol adsorption on Au surface. The formed alkanethiol layer serves as an insulator to reduce the background current while providing a ratio of about 1:5 between —COOH and —OH groups at the top surface. The electrode was then incubated in 2.0 mM peptide-Fc substrate mixed with 0.2 g/L 1-ethyl-3-(3-dimethylaminopropyl)carbodiimide (EDC) and 0.2 g/L N-hydroxysulfosuccinimide (Sulfo-NHS) as coupling agents for 2 hours at room temperature to form amide bonds between the amine group in the peptide-Fc substrate and the carboxylic acid group on the SAM surface. The mixed —COOH and —OH groups in the SAM surface was found to be critical in lowering the peptide-Fc density on the Au surface to reduce the steric hindrance in the subsequent proteolysis measurements. The functionalized chip was rinsed with deionized water for 30 seconds to remove the physically adsorbed molecules.

Electrochemical Experiments. Electrochemical experiments were performed on a specially designed electrochemical cell mounted on a large copper block for temperature control by circulating thermostatic silicone liquid through the internal channels. The thermal circulator (Julabo, Allentown, PA) was set to achieve a temperature of 38.6° C. Two buffer solutions, 0.5×PB (pH=7.4) and 25 mM MES (pH=5.0), were used. In some experiments, the rhCB was activated by incubation in 25 mM MES buffer (pH=5.0) containing 5 mM DTT for 15 min. About 10 uL activated cathepsin B solution was added to the electrochemical cell containing 815 uL buffer solution (i.e., 0.5×PB with pH=7.4) as the electrolyte. Fc signal on the Au surface was detected by alternating current voltammetry (ACV) with an AC frequency of 300 Hz and a voltage amplitude of 100 mV on a DC ramp from −0.45 V to 0.20 V vs. MSE. Electrochemical measurements were performed using an IVIUM n-Stat potentiostat (Eindhoven, The Netherlands), which allows measurement of up to ten independent working electrodes simultaneously versus a common MSE reference electrode and a common Pt coil counter electrode.

ELISA Measurements. Cathepsin B concentrations were validated using an ELISA kit from R&D Systems in a 96-well plate using a sandwich-type ELISA for detecting cathepsin B. In this system, the primary antibody adsorbs to the polystyrene well, and the remaining surface area of the well is passivated with bovine serum albumin. Cathepsin B binds to the immobilized primary antibody. The secondary, biotin-labeled antibody binds to immobilized cathepsin B, and streptavidin-conjugated horseradish peroxidase attaches to the biotin label. Catalytic oxidation of the substrate to a colored product. The well is washed thoroughly with a surfactant solution (0.05% Tween® 20 in the PBS buffer) between the steps in each panel. FIG. 26 demonstrates the ability of ELISA in measuring cathepsin B in HS. A linear curve can be obtained in the range of 0.5% to ~5% dilution. It started to deviate from the linear line above 5% dilution. Thus 2.5% HS was used in later ELISA experiments of spiked rhCB. A series of activated and non-activated rhCB samples were first prepared in 0.5× phosphate buffer (0.5× PB) consisting of ~3.6 mM $Na_2HPO_4$ and ~2.3 mM $NaH_2PO_4$, pH=7.4. About 1% BSA was added in the 0.5×PB to reduce non-specific adsorption. Another series of solutions were prepared by spiking different amounts of activated and non-activated rhCB into the solution containing 2.5% HS besides the 0.5×PB and 1% BSA. The rhCB activation was done by first incubating the high-concentration rhCB in 25 mM 2-(4-morpholino) ethanesulfonic acid (MES) buffer containing 5 mM dithiothreitol (DTT) at room temperature for 15 minutes and then diluting into desired rhCB concentrations in proper solutions. For the series involving spiking activated rhCB into 2.5% HS solutions, the HS was activated at the same conditions, i.e., in 25 mM MES (pH=5.0) and 5 mM DTT, before mixing with the activated rhCB and diluting to the final 2.5% HS solution. After completing the ELISA procedure, the optical density (OD) in the developed wells of the 96-well plate was measured at 450 nm wavelength with an EL311 microplate autoreader (Biotek, Winooski, VT).

RESULTS AND DISCUSSION

Figure 20:
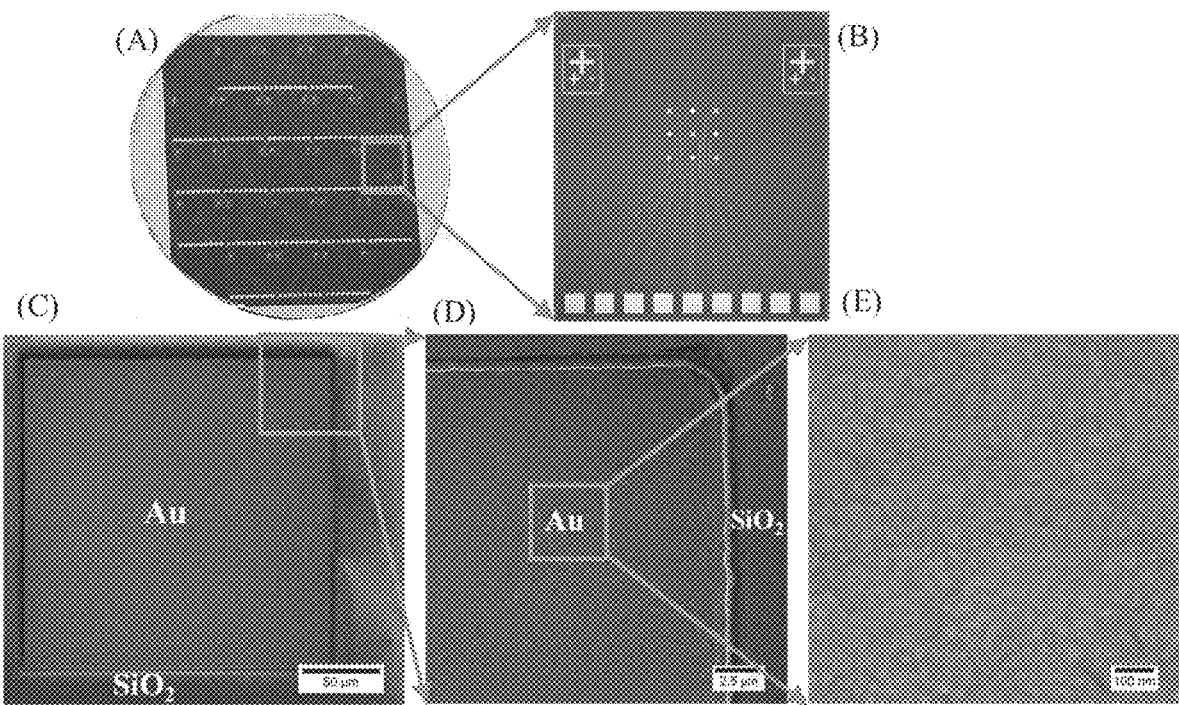
FIG. 20 shows optical images of (A) a 4" Si wafer consisting of 21 Au MEA chips and (B) a single Au MEA chip in which the size of the contact pads at the bottom is 1.0 mm×1.0 mm. SEM images of (C) a full microelectrode (the one at the center with the contact line at the right side), (D) the corner of the Au microelectrode whose edges are encapsulated under the surrounding insulating $SiO_2$ layer, and (E) the microstructure of the Au electrode surface. The scale bars in panels (C) to (E) are 50 um, 2.5 um and 500 nm, respectively.

MEA Characterization. FIG. 20 shows optical and scanning electron microscopy (SEM) images to illustrate the features from the whole 4" wafer to the local surface of the Au microelectrodes. A 4" wafer consists of 21 Au MEA chips (FIG. 20A). A diced individual chip (FIG. 20B) consists of 9 microelectrodes (200 μm×200 μm each) in a 3×3 array, each of which is independently connected to a contact pad (1 mm×1 mm) that is lined at the bottom of the chip. The exposed contact pads are connected to the multi-channel IVIUM potentiostat through pogo pins. As shown in FIGS. 20C and 20D, the edges of each Au microelectrode (~a few microns) and the connection lines are buried under a 1.0-μm thick insulating $SiO_2$ layer. The Au surface consists of ~30-50 nm grains, which provide a higher effective surface area than a flat Au surface. This MEA is highly robust and can be repeatedly used multiple times after cleaning and re-functionalization with the procedure described in the experimental section.

Principle of the Electrochemical Detection of Protease Activity. The sensing principles are described in Example 1. As shown in the cyclic voltammogram (CV) in FIG. 27, the Fc tag in the peptide-Fc functionalized at the Au microelectrode surface can be oxidized into ferrocenium ($Fc^+$), giving a pair of well-defined redox waves centered at −0.15 V (vs. MSE). These peaks disappeared after the peptide-Fc substrate was cleaved by proteolysis. The surface concentration of peptide-Fc substrate $\Gamma_{Ss}$ can be derived from the integrated area under the oxidation peak to give $\Gamma_{Ss}$=3.1 pmol/$cm^2$, corresponding to an average nearest-neighbor distance of 7.9 nm between the peptide-Fc. This low density allows easy access by the protease. As further shown in FIG. 28, the weak faradaic signal can be amplified using ACV, i.e., applying an AC voltage on top of a DC potential ramp from −0.45 V to 0.20 V (vs. MSE). The optimal AC conditions were found to be 300 Hz in frequency and 100 mV in voltage amplitude for H-15 peptide-Fc functionalized on the Au electrode. An ACV peak was observed at the same potential (−0.15 V) as in CV, confirming that it is attributed to the specific faradaic signal from the functionalized peptide-Fc. The capacitive baseline can be subtracted from the raw ACV curves to extract only the faradaic ACV peak current $i_p$ which is proportional to the amount of attached peptide substrate, peptide-Fc. In the presence of cathepsin B, some of the peptide-Fc substrates were proteolyzed by cathepsin B between Leu and Ala (as determined by HPLC-MS in Example 1), causing the Fc redox tag to diffuse away from the electrode surface. Consequently, the anodic peak current $i_p$ in ACV decreased over time. Such kinetic proteolytic curves, typically at a time interval of 30 seconds and recorded continuously for 60-80 minutes, can be fit with the following function:

$$i_p=a[\exp(-t/\tau)]+bt+c \qquad (1)$$

where the exponential term $a[\exp(-t/\tau)]$ corresponds to the proteolysis reaction, and the linear term (bt+c) accounts for the background drift. The exponential decay time constant r represents the proteolysis reaction rate, i.e., a smaller τ value indicates the faster reaction and higher protease activity.

The proteolysis kinetics can be accurately described by the heterogeneous Michaelis-Menten model. Importantly, the protease activity can be represented by the inverse of the exponential decay time constant τ as:

$$\frac{1}{\tau} = \left(\frac{k_{cat}}{K_M}\right)[E]_0, \qquad (2)$$

where $k_{cat}/K_M$ is a specific constant revealing the intrinsic catalytic efficiency of the protease to the specific peptide substrate, and $[E]_0$ is concentration of the active protease. The τ value depends on both the catalytic efficiency and the protease concentration. The traditional affinity-based measurements (such as ELISA) only indirectly reveal $[E]_0$ but not $k_{cat}/K_M$. In this study, we focus on deriving the protease catalytic activity by fitting the kinetic exponential decay curves that give the value of $(k_{cat}/K_M)[E]_0$. As will be shown in later sections, the $(k_{cat}/K_M)$ value strongly depends on the measuring conditions such as peptide sequence, buffer composition and temperature as well as the properties of proteases. This carries rich information related to the biological function of the protease, which cannot be obtained from the concentration of the protease determined by affinity-based analytical techniques, such as ELISA.

Electrochemical Detection of Cathepsin B Activity Close to Physiological Conditions. According to the literature, the optimal cathepsin B assay buffer is 25 mM MES buffer (pH=5.0), an acidic buffer. This is also the assay buffer recommended by the vendor (R&D Systems Inc.) and was used in Example 1. FIG. 29 shows the typical kinetic proteolytic curves of 1.0 nM activated cathepsin B in 25 mM MES buffer from 9 microelectrodes in the Au MEA functionalized with the same peptide-Fc substrate. The average activity ($1/\tau$), i.e., the measured protease activity, is $(1.21\pm0.46)\times10^{-4}$ s$^{-1}$. Results from 9 microelectrodes in the Au MEA are highly consistent with the curves overlapping with each other. However, the long-term goal of our study is to develop the Au MEA as a cancer diagnostic technique for simultaneously measuring the activity of multiple cancer-related extracellular proteases in HS samples. The representative proteases that have been reported to be related to cancer development include cathepsin B, ADAM-10, ADAM-17, MMP-9, uPA, etc., which may require very different pH values for optimal proteolysis. For example, the recommended assay buffer for ADAM-10 and ADAM-17 is 25 mM Tris, 2 µM ZnCl$_2$, 0.005% (w/v) Brij35 with pH=9.0 by the vendor (R&D Systems, Catalog Number: 936-AD). This pH value is 4 units higher than the optimal MES buffer (pH=5.0) for cathepsin B. To facilitate future multiplex detections, we investigated the possibility for electrochemical detection of proteolysis in a common buffer for all extracellular proteases in HS, i.e., at the neutral pH=7.4. This pH value is compatible with the physiological condition of HS and is the optimal condition for some proteases, such as MMP-7 measured in tricine buffer (pH=7.4).

To achieve the above goals, we first tried the commonly used phosphate buffer saline (PBS) (pH=7.4). FIG. 30 shows the kinetic proteolysis curves measured with the Au MEA functionalized with peptide-Fc in 1.0 nM activated cathepsin B dispersed in 1×PBS, 0.5×PBS and 0.2×PBS, respectively. Clear exponential decay was observed in all three buffers. The inverse decay constant ($1/\tau$), i.e., the measured protease activity, is $(4.2\pm1.1)\times10^{-4}$ s$^{-1}$, $(11.44\pm0.64)\times10^{-4}$ s$^{-1}$ and $(7.65\pm0.42)\times10^{-4}$ s$^{-1}$ for 1×, 0.5× and 0.2×PBS, respectively. To our surprise, all these activity values are higher than that in MES buffer, i.e., $1.21\times10^{-4}$ s$^{-1}$. In addition, the proteolysis rate strongly depends on the ionic strength of the buffer. The catalytic proteolysis reaction in 0.5×PBS is faster than those from both 1× and 0.2×PBS. The buffer concentration also had an impact on the stability of the Au MEA as reflected in the linear ACV peak current drifting in the period before adding cathepsin B, i.e., before t=0 min. It is clear that the drift rate is higher at higher PBS concentration. It is likely that the chloride ions in high-concentration PBS may have caused roughening and dissolution of the Au surface, as reported previously.

To improve the stability of the Au electrode, we modified the common PBS by removing sodium chloride and potassium chloride. The re-formulated home-made buffer only consists of the proper ratio of two phosphate salts, i.e., 3.6 mM sodium phosphate dibasic heptahydrate (Na$_2$HPO$_4$·7H$_2$O) and 2.3 mM sodium phosphate monobasic monohydrate (NaH$_2$PO$_4$H$_2$O) to give pH=7.4, referred to as "1×PB" in this study. The buffer was diluted with deionized water to 0.5× prior to use in order to obtain a high proteolysis activity. FIG. 31 shows the representative raw proteolytic curves and the fitting to the extracted exponential portion from nine sets of data obtained simultaneously from the same Au MEA. Again, the measurements from different microelectrodes are highly consistent and overlapping with each other. A striking feature is that the peak current decays much faster than those in both MES buffer and 0.5×PBS.

FIG. 21A provides direct comparison of the normalized kinetic proteolysis curves of the peptide-Fc modified Au MEA by 1.0 nM activated cathepsin B in 0.5×PB (pH=7.4) and the 25 mM MES buffer (pH=5.0), respectively. Since the ACV peak currents vary among different Au MEA chips, they are normalized to the value right before adding cathepsin B to give ip/ip$_0$ so that the proteolytic curves can be directly compared. The exponential decay portions are plotted and fitted in FIG. 21B. FIG. 21C shows the fitted $1/\tau$ values from 8 channels of the Au MEA in the two buffers (with one channel omitted due to loose contact). The average measured activities ($1/\tau$) in 0.5×PB and 25 mM MES buffer are $(42.1\pm3.7)\times10^{-4}$ s$^{-1}$ and $(1.21\pm0.46)\times10^{-4}$ s$^{-1}$, respectively. The activity is unexpectedly nearly 40 times higher in 0.5×PB. It is noteworthy that these two sets of electrochemical experiments were carried out on the same Au MEA chip, with the same preparation procedure, and at the same measurement conditions (300 Hz ACV frequency, 100 mV ACV voltage amplitude, and 38.6° C. temperature setting). This finding strongly indicates that switching the assay buffer from 25 mM MES to 0.5×PB is feasible. Thus, all our electrochemical measurements in later sections were carried out in 0.5×PB.

Figure 21:
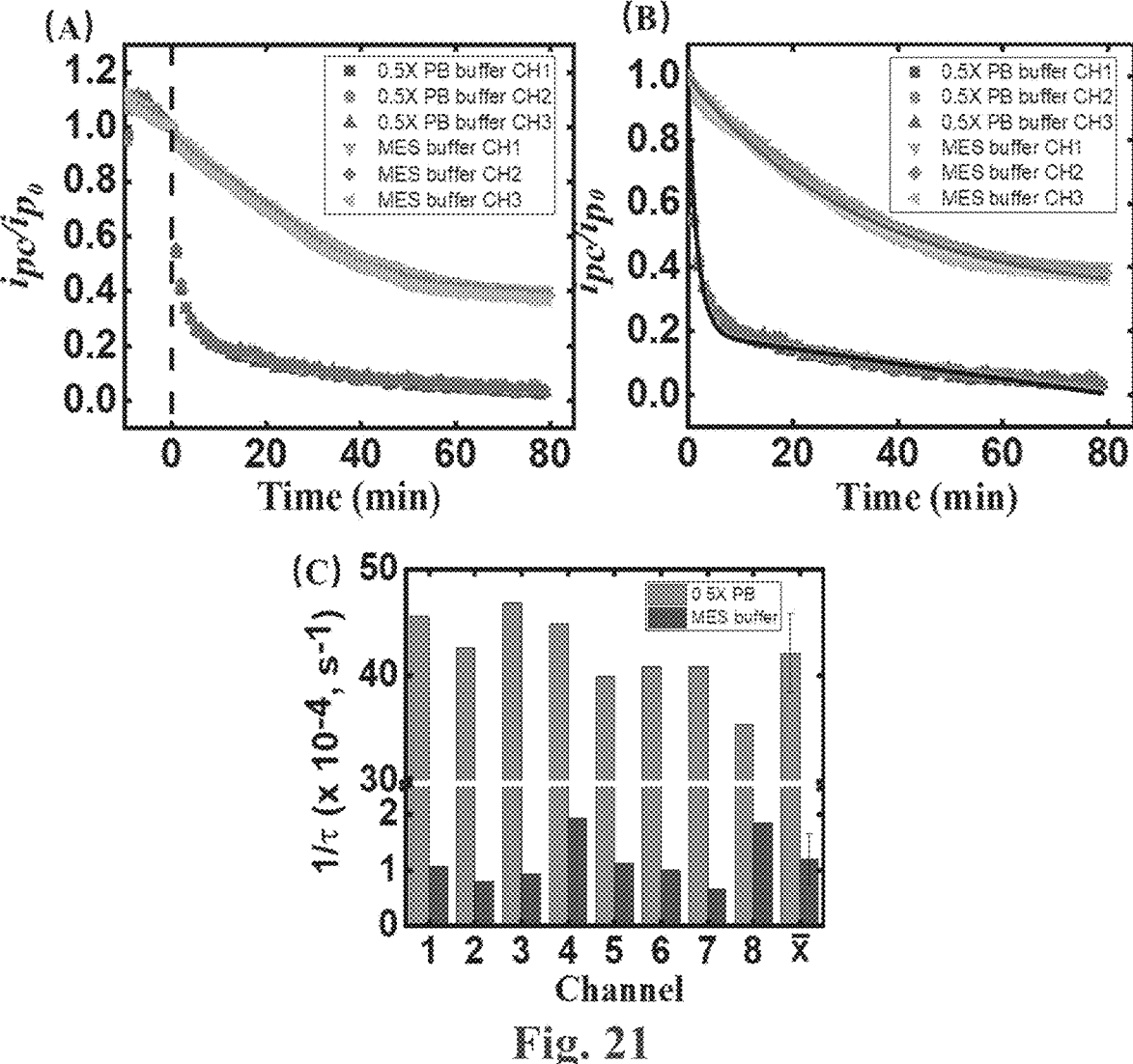
FIG. 21 shows (A) Representative normalized kinetic proteolysis curves for Au MEA modified with peptide substrate H-15 with Fc moiety (peptide-Fc) by 1.0 nM activated cathepsin B in 0.5×PB (pH=7.4) and 25 mM MES buffer (pH=5.0), respectively. (B) The fitting of the extracted kinetic proteolysis curves. (C) The bar graph showing the fitted values of 1/τ from 8 individual channels, with the average value and the standard deviations (as the error bars) of these 8 channels shown at the far right.

Assessment of the LOD in Measuring Activated Cathepsin B in 0.5×PB. Since the proteolysis is much faster in 0.5×PB than in 25 mM MES buffer as shown in FIG. 21, a much lower LOD can be expected. To assess the LOD in 0.5×PB, a series of proteolysis measurements were carried out at different activated rhCB concentrations using Au MEA chips functionalized with the peptide-Fc substrate. As shown in FIG. 22A, the proteolytic curve decayed faster as the rhCB concentration increased. FIG. 22B shows the derived activity ($1/\tau$) vs. the rhCB concentration, with the error bars representing the standard deviation of eight replicates for each measurement. The $1/\tau$ value linearly increases from blank to 1.0 nM cathepsin B but is saturated at about $45\times10^{-4}$ s$^{-1}$ when the rhCB concentration is above 1.0 nM. The saturation may be due to the steric interference between the adsorbed rhCB on the planar Au surface, leading to a significantly decreased slope at higher rhCB concentration. The fitting line between 0 to 1.0 nM is shown in FIG. 22C and can be described as:

$$1/\tau \text{ (in s}^{-1}) = (3.89\pm0.28)\times10^6 \text{ M}^{-1}\text{s}^{-1} \text{ [rhCB]} + (6.89\pm0.83)\times10^{-4} \text{ s}^{-1}, \qquad (3)$$

with [rhCB] in unit of M. The slope m=$(3.89\pm0.28)\times10^6$ M$^{-1}$s$^{-1}$ reveals the specificity constant k$_{cat}$/K$_M$= $(3.89\pm0.28)\times10^6$ M$^{-1}$s$^{-1}$, which is within the range of $0.928\times10^6$ to $7.288\times10^6$ M$^{-1}$s$^{-1}$ reported for activated human cathepsin B with different peptide substrates. The LOD of activity can be determined to be $8.49\times10^{-4}$ s$^{-1}$ by $$\text{LOD of activity} = 3\sigma_{blank} + (1/\tau)_{blank}, \qquad (4)$$

where $\sigma_{blank}$=$0.74\times10^{-4}$ s$^{-1}$ is the standard deviation of blank and $(1/\tau)_{blank}$=$6.27\times10^{-4}$ s$^{-1}$ is the mean value of blank experiments. The LOD of cathepsin B centration can be determined as $57.1\pm0.41$ pM by:

$$\text{LOD of [rhCB]} = 3\sigma_{blank}/\text{m}. \qquad (5)$$

Compared with the 0.32 nM LOD in our previous study using VACNF nanoelectrode arrays in 25 mM MES buffer (U.S. Pat. No. 9,850,520, filed Jun. 30, 2014, incorporated by reference herein), the LOD of rhCB in this study is about six times lower. Changing the assay buffer from 25 mM MES to 0.5×PB and using the proper density of peptide-Fc on the Au MEA significantly improved the detection sensitivity.

Validation of Cathepsin B in 0.5×PB by ELISA Measurements. ELISA is a highly sensitive and highly selective affinity-based technique for detecting protein analytes through specific binding with the antibodies. The signal is amplified by enzymatic conversion of the colorless substrate to a colored product. Here, ELISA is employed to selectively measure the concentration of rhCB and validate the electrochemical activity measurements. We first carried out the ELISA measurements at a series of non-activated rhCB concentrations in 0.5×PB. As shown in FIG. 23A (black filled squares), it gives a linear curve in the range of 0 to 250 μM rhCB.

The fitted calibration curve can be expressed as:

$$OD=(1.29\pm0.025)\times10^{-3}\ pM^{-1}\times[rhCB]+(0.0082\pm0.0037), \tag{6}$$

where the unit of [rhCB] is pM. We then spiked the same concentrations of non-activated rhCB into diluted HS in 0.5×PB. As explained earlier, 2.5% HS was chosen for the spiking experiments since it is in the middle of the linear range shown in FIG. 26. Spiking rhCB into 2.5% HS (red filled circles) also shows a linear curve with the slope similar to that in 0.5×PB but the OD values consistently upshift by about 0.21. The fitted calibration curve is:

$$OD=(1.54\pm0.073)\times10^{-3}\ pM^{-1}\times[rhCB]+(0.2169\pm0.0103). \tag{7}$$

The upshift of the calibrations curve in the 2.5% HS solution can be attributed to the intrinsic cathepsin B in the HS sample. Its concentration in the 2.5% HS can be estimated to be equivalent to 162±9.5 μM rhCB by inputting the intercept in 2.5% HS (OD=0.2169±0.0103) as the signal in the calibration equation (6). This translates into ~6.5±0.4 nM equivalent rhCB in 100% HS. Since the rhCB consists of ~60% 37 kDa proenzyme and ~40% 29 kDa active enzyme with an average molecular weight of 33.8 kDa, the cathepsin B quantity in 100% HS by our ELISA study can be estimated as ~220±13 ng/mL, which is close to the reported values of 13.2 ng/mL to 126 ng/mL in HS by ELISA in the literature. From these results, the LOD of cathepsin B concentration by ELISA can be determined as −32±0.6 μM in 0.5×PB and −59±2.8 μM in 2.5% HS in 0.5×PB based on the 3-σ definition (LOD=3σ/m), where a is the standard deviation in measurements of the low rhCB concentration sample (25 pM) and m is the slope of the calibration equations (6) and (7), respectively. Thus, the LOD of rhCB concentration by our electrochemical method is comparable to that by ELISA. However, while each set of ELISA measurements followed the same trends as FIG. 23, there were variations between different sets due to the semi-quantitative nature of ELISA. This led to lower LOD of ~18±1.3 μM in 0.5×PB and ~24±0.6 μM in 2.5% HS in 0.5×PB in a set of repeated ELISA experiments; nevertheless, the main conclusions do not change.

Figure 22:
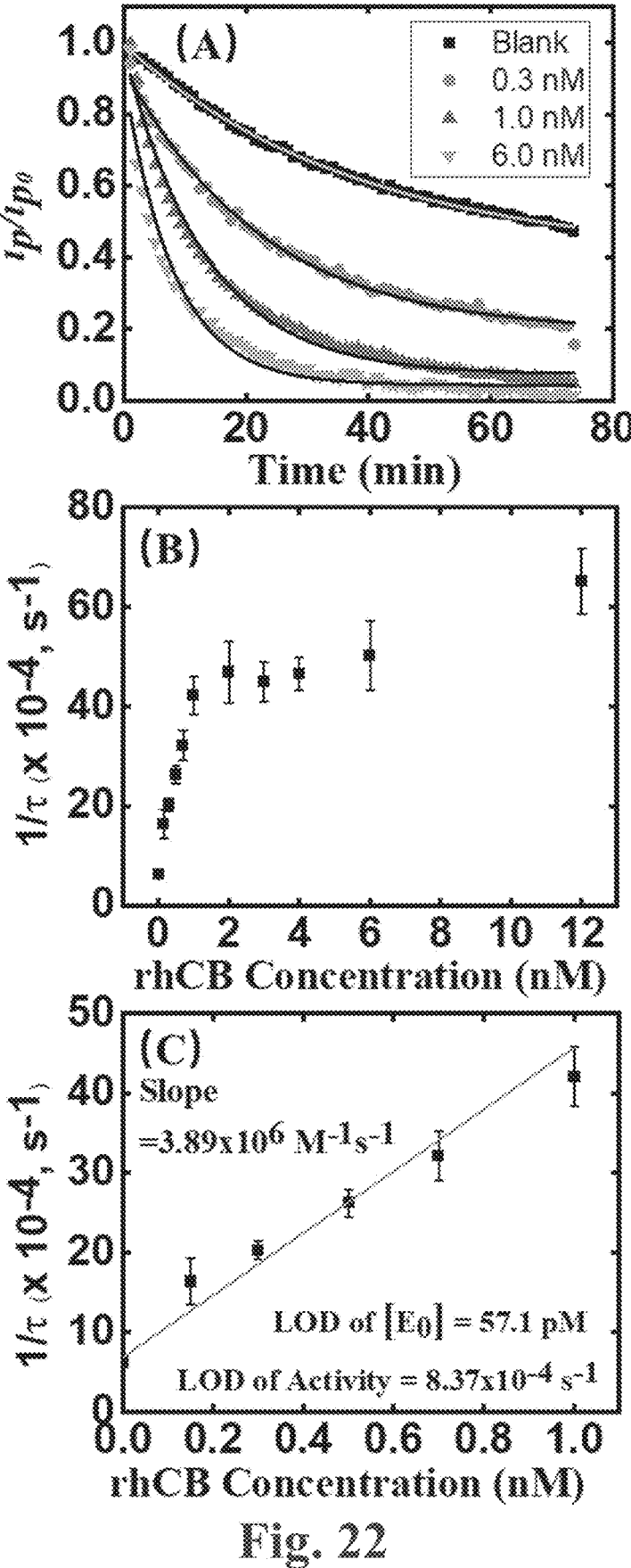

Since the non-activated rhCB includes active (~40%) and non-active forms (~60%), the electrochemical measurements in FIG. 21 and FIG. 22 were done after activating the rhCB in the MES and DTT solution (pH=5.0). The activation process is assumed to convert all non-active proenzymes into the active mature form. To assess whether the activation affects the ELISA measurements, we carried out two more sets of ELISA measurements shown in FIG. 23B, including adding activated rhCB into the 0.5×PB (blue filled upper triangles) and spiking the same amount of activated rhCB into the pre-activated 2.5% HS in 0.5×PB (green filled inverted triangles). Both sets of data show similar slopes (represented by the two parallel lines in FIG. 23B), but their values are substantially lower comparing to those using non-activated rhCB. Thus, the detection sensitivity is suppressed. This could be attributed to two possibilities: (1) The activation reagents (MES and DTT) may interfere with the binding of the active rhCB with antibodies during ELISA, and (2) some binding sites may be located on the surface of the cleaved domains, thus leading to lower efficiency in forming the sandwich structure in ELISA measurements. Since MES and DTT are diluted by more than 100 times after activation, the first possibility is unlikely to be the main factor. Based on this observation, ELISA is more sensitive to the inactive proenzyme in the sample and is not suitable in detecting the active rhCB. Interestingly, the intercepts of the curves with activated or non-activated rhCB are about the same in either 0.5×PB or 2.5% HS, but those in 2.5% HS show the similar upshift in OD comparing to those in 0.5×PB. The presence of cathepsin B in HS is obviously responsible to this upshift.

Electrochemical Detection of Cathepsin B Activity in Human Serum. To assess the activity of cathepsin B in HS, we compared the kinetic proteolysis curves of 5% HS in 0.5×PB with and without activation by the electrochemical method. The 5% HS concentration is slightly higher than the 2.5% used in ELISA measurements to ensure that a clear exponential decay can be observed in electrochemical experiments. To minimize errors, three Au MEA chips were prepared side-by-side for three sets of experiments, i.e., (i) non-activated 5% HS in 0.5×PB, (ii) activated 5% HS in 0.5×PB, and (iii) the blank 0.5×PB. In experiment (ii), the 5% HS in 0.5×PB was activated by incubating 41.25 μl of stock HS mixed with 3.75 μl of 60 mM DTT in 300 mM MES (pH=5.0) for 15 min. At t=0 min, all 45 μl activated solution was added to the electrochemical cell that was prefilled with 780 μl of 0.5×PB. In the final solution, the HS was diluted to 5%. In experiment (i), proper amount of stock HS was directly added into the prefilled electrochemical cell to dilute the final HS concentration to 5%. FIG. 24A shows 3 sets of representative proteolysis curves for each experiment. Clearly, the kinetic proteolysis rate of the blank 0.5×PB is the slowest, followed by higher rate in non-activated 5% HS and the highest rate in activated 5% HS. FIG. 24B is the bar chart plot showing the average value and standard deviation of the corresponding 1/τ value over 8 independent channels for each experiment. The cathepsin B activities (1/i) are (6.27±0.74)×10⁻⁴, (12.2±0.8)×10⁻⁴, and (33.2±3.0)×10⁻⁴ s⁻¹, respectively. Based on equation (2), the concentration of the active form of cathepsin B in non-activated and activated sample (equivalent to 100% HS) can be calculated by:

$$[CB]_{100\%\ HS}=\left[\frac{(1/\tau)_{5\%\ HS}-(1/\tau)_{blank}}{m}\right]\times\frac{100\%}{5\%}, \tag{8}$$

where $(1/\tau)_{blank}$=(6.27±0.74)×10⁻⁴ s⁻¹ and m=(3.89±0.28)× 10⁶ M⁻¹s⁻¹ is the slope of calibration curve in Equation (3). Thus, the concentration of active cathepsin B can be calculated as 3.05±0.60 nM in non-activated stock HS and as 13.8±1.9 nM in the activated sample. Assuming that the activation process fully converted cathepsin B into the active form, the total cathepsin B concentration in the initial HS sample, including both the active form and inactive form (proenzyme), is 13.8 nM. Thus, it can be estimated that about 22% of the cathepsin B in the stock HS is in the active form. It is noteworthy that the total cathepsin B concentration (13.8 nM) by the electrochemical method is significantly higher than 6.5 nM derived by ELISA. This could be attributed to two possibilities: (i) the electrochemical detection involved non-specific cleavage to the peptide-Fc by other proteases in the HS sample and (ii) the ELISA measurements were suppressed by other compositions in the HS, i.e., the presence of a matrix effect. The most remarkable difference between the electrochemical method and ELISA is that the electrochemical method is highly sensitive to the activity of cathepsin B, i.e., showing a much higher proteolysis rate when it is activated, while ELISA is more sensitive to the inactive form.

Electrochemical Assessment of Effective Cathepsin B Activity Spiked in Human Serum. HS contains very complex components, which may affect the assay sensitivity and reproducibility. To assess the matrix effects, we have carried out the study by spiking different amount of active rhCB into the non-activated 5% HS in 0.5×PB. FIG. 32 shows the raw proteolysis curves of the non-activated 5% HS in 0.5×PB and the corresponding fitting lines. The data were recorded over 8 channels of the peptide-Fc modified Au MEA simultaneously. Similar measurements were seen after fitting after spiking 1.0 nM non-activated rhCB into the non-activated 5% HS in 0.5×PB. As specified by the vendor (R&D Systems), the purchased rhCB contains ~40% active cathepsin B. Similar measurements were seen after spiking 1.0 nM activated rhCB into the non-activated 5% HS in 0.5×PB. In this experiment, an activation process with 5 mM DTT in 25 mM MES buffer was applied to convert all 1.0 nM cathepsin B into the active form, serving as the condition with 1.0 nM active rhCB spiked into the non-activated 5% HS.

Three representative sets of proteolysis curves are plotted in FIG. 25A for direct comparison. Adding 0.40 nM naturally active cathepsin B into 5% HS in 0.5×PB only causes a slightly increased proteolytic rate. However, a much higher proteolytic rate is observed after adding 1.0 nM activated cathepsin B. The bar graph in FIG. 25B illustrates the measured lit value for each experiment, which are $(12.15\pm0.8)\times10^{-4}$, $(12.99\pm1.66)\times10^{-4}$, and $(68.4\pm7.53)\times10^{-4}$ s$^{-1}$, respectively. The increased effective rhCB concentration, A[rhCB], in the spiked 5% HS solution can be calculated based on the difference of the measured lit value in the spiked and non-spiked samples following:

$$\Delta[rhCB]_{5\% HS} = \frac{(1/\tau)_{spiked\ 5\%\ HS} - (1/\tau)_{5\%\ HS}}{m}, \quad (9)$$

where the slope of the calibration curve m=$(3.89\pm0.28)\times10^6$ M$^{-1}$s$^{-1}$ is from Equation (3). This gives $\Delta[rhCB]_{5\%\ HS}$= 0.0216±0.047 nM, which corresponds to only (5.4±11.8)% recovery percentage of the spiked 0.4 nM naturally active rhCB. The spiked active rhCB was obscured by the HS matrix, making the effect undetectable. In contrast, the 1/π value after spiking 1.0 nM activated cathepsin B into the 5% HS was much larger, which led to a recovery percentage of (140±20)% following the above calculation. It is worth mentioning that these two spiking experiments have critical differences. The cathepsin B activation reagents (such as DTT) used in the latter experiment, though were diluted to 0.27 mM in the final spiked solution, may interact with the inherent cathepsin B and other cathepsins in the HS. It is known that many of the 11 cysteine proteases, cathepsins (B, C, F, H, K, L, O, S, V, X and W), have largely overlapping specificities and may catalyze proteolysis of the similar peptide substrates. While further studies are needed to develop a better understanding of these results, it is clear that the electrochemical method can sense the small changes in activity of the extracellular cathepsin B in HS.

In summary, the above results are encouraging for detecting cathepsin B activity by the electrochemical method using Au MEAs in neutral phosphate buffers (pH=7.4). This enables direct detection of the intrinsic activity of human serum at the physiological conditions without altering the nature of the extracellular proteases. It paves the way for future multiplex detection of different protease families in a common buffer. The electrochemical method is very sensitive to the activity of cathepsin B as demonstrated in the measurements of diluted HS and the spiking experiments with or without applying a pre-activation procedure. In contrast, ELISA measurements are more sensitive to the non-activated rhCB in both 0.5×PB and 2.5% HS. Due to the large differences between ELISA and the electrochemical protocols, it is difficult to carry out the activation experiments under the same conditions, making it difficult to draw solid conclusions. However, these techniques reveal different aspects of proteases and generally validate each other. This provides useful new insights into the catalytic properties of extracellular proteases in HS, which may inspire further studies to understand the complex proteolysis problems and to push protease activity profiling toward disease diagnosis.

CONCLUSION

We have demonstrated successful electrochemical detection of the activity of rhCB in diluted HS with 0.5×PB buffer at pH=7.4 using a 3×3 Au MEA. The catalytic activity of cathepsin B $(k_{cat}/K_M)[CB]$ is represented by inverse of the exponential decay time constant, i.e., $1/\tau$, which can be derived by fitting of the kinetic proteolysis curve measured with continuously repeated AC voltammetry measurements. The activity was found to be sensitive to the pH value and the ionic strength of the buffer. In low-ionic-strength neutral 0.5×PB, the activity of cathepsin B was surprisingly nearly 40 times of that in the typical optimal buffer, i.e., 25 mM MES with pH=5.0. A linear calibration curve was obtained in the range of 0 to ~1.0 nM of activated cathepsin B, which led to a very low LOD of rhCB at 57.1 μM. The specificity constant $k_{cat}/K_M$ was determined to be $(3.89\pm0.28)\times10^6$ M$^{-1}$s$^{-1}$, comparable to that of human cathepsin B measured by fluorescence technique in the literature. ELISA measurements validated that the pooled HS sample contained 6.5 nM cathepsin B. The LOD of rhCB concentration by the electrochemical method is comparable to ELISA. However, ELISA results are dominated by proenzymes and the signal is suppressed in measuring active rhCB. In contrast, the electrochemical method is sensitive to the catalytic properties of the active cathepsin B and shows a significantly higher activity when the rhCB and HS are activated in acidic buffer. Spiking 1.0 nM non-activated cathepsin B (containing ~40% naturally active enzyme) and 1.0 nM activated cathepsin B into 5% HS further demonstrates the electrochemical method's ability to detect the activity of cathepsin B in the analytes. Particularly, the gold MEA platform has a great potential for rapid multiplex detection of activities of extracellular proteases towards cancer diagnosis and treatment efficacy assessment.

SUPPORTING INFORMATION

The supporting information includes the detailed materials and instruments used in this study, the Au MEA fabrication procedures, procedures for ELISA measurements, derivation of the Michaelis-Menten model for electrochemical data analysis, and additional electrochemical kinetic proteolysis results of Au MEA in different buffers and in 5% human serum samples.

1. Materials and Instruments

N-Fluorenylmethyloxycarbonyl (Fmoc) protected amino acid, 1-[bis(dimethylamino)methylene]-1H-1,2,3-triazolo [4,5-b]pyridinium-3-oxidehexafluorophosphate (HATU), amino acid attached 2-chlorotrityl resins, and 2-(1H-benzo-rtiazol-1-yl)1,1,3,3-tetramethyluronium hexafluorophosphate (HBTU) were bought from Chem-Impex International, Inc. (Wood Dale, IL) and AAPPTEC LLC (Louisville, KY). N-Hydroxysulfosuccinimide (Sulfo-NHS), 6-mercapto-1-hexanol, and 6-mercapto-1-hexanoic, and 1-ethyl-3-(3-dimethylaminopropyl)carbodiimide (EDC) were purchased from Sigma-Aldrich (St. Louis, MO). Sodium phosphate dibasic heptahydrate ($Na_2HPO_4 \cdot 7H_2O$), sodium phosphate monobasic monohydrate ($NaH_2PO_4H_2O$), dithiothreitol, and 2-(4-morpholino)eth-anesulfonic acid (MES) were purchased from Fisher Scientific (Hampton, NH). The 1× phosphate buffer (PB) was prepared as 7.17 mM potassium phosphate dibasic anhydrous and 4.63 mM potassium phosphate monobasic (pH=7.4, adjusted using potassium hydroxide) purchased from Fisher Scientific (Fair Lawn, NJ) in deionized water. This is modified from the standard phosphate buffer saline (PBS) by removing other salts to lower the ionic strength. The 0.5×PB was prepared by 2-fold dilution of 1×PB with deionized water to further lowering the ionic strength. Carrier-free recombinant human cathepsin B (rhCB) (~60% 37 kDa proenzyme, ~40% 29 kDa mature enzyme), cathepsin B specific fluorogenic peptide substrate, human total cathepsin B DuoSet ELISA kit, and DuoSet ancillary reagent kit 2 were obtained from R&D Systems Inc. (Minneapolis, MN). Solutions of 1% bovine serum albumin (BSA) in 0.5×PB were prepared as 10 mg/mL from solid bovine serum albumin purchased from Tocris Bioscience (Bristol, UK). Cathepsin B solutions were activated in 25 mM MES buffer containing 5 mM DTT for 15 min to activate the proenzyme. The ferrocene (Fc) labeled peptide substrate was synthesized using a solid-phase microwave peptide synthesizer CEM Discover (Matthews, NC) in D. H. Hua's laboratory. The synthetic procedure is the same as Example 1 for H-15. A "pooled human serum off the clot" (catalog no. ISER 10ML, Innovative Research, Novi, Michigan) was used to validate the detection. Such human serum (HS) sample was whole blood derived by allowing the blood to clot and then processed into serum via centrifugation. The supernatant serum solution was frozen immediately after processing.

2. Fabrication of Au MEA

The 4" Si(100) wafer was first oxidized in gaseous $H_2O$ at 1100° C. for 45 min to form a 550 nm $SiO_2$ layer on the surface. Then, the wafers were coated with alternating thin layers of Ti (20 nm), Au (100 nm), and Ti (20 nm) using electron beam evaporation (Innotec ES26C, Battle Ground, WA). The wafers were then spin-coated with 1.0 μm SPR3612 positive photoresist (Rohm and Haas Electronic Materials, Marlborough, MA) using an automated spin-coating track (SVG 8400, San Jose, CA) and exposed on a mask aligner (Karl Suss MA-1, Garching, Germany) with an exposure dose of 80 mJ/cm² (exposure time=5.3 s) through a chrome photomask (FrontRange Photomask, Lake Havasu City, AZ). After developing with an automated developing track (SVG 8600, San Jose, CA), a photoresist electrode MEA pattern was formed on the wafer. The exposed Ti top layer was then etched with 2% aqueous HF solution, the underneath Au layer was removed with Transene TFA Au, and again with 2% HF to remove the bottom layer of Ti. The MEA pattern was reserved because the photoresist, which was stripped off after etching. A 1-μm thick layer of $SiO_2$ was deposited over the entire wafer by plasma-enhanced chemical vapor deposition (PE-CVD, Plasma-Therm Shuttle-lock SLR-730-PECVD, St. Petersburg, FL) with 250 sccm 5% $SiH_4$/He, 800 sccm He and 1700 sccm $N_2O$ at 350° C., 1100 mTorr and 200 W for 15 min. Next, the second photolithography with the same recipe was processed on the wafer again to expose the contact pad and microelectrode while covering the remaining areas protected by photoresist. The exposed $SiO_2$ was etched with $CHF_3$ plasma (2 sccm 02 and 45 sccm $CHF_3$ at 5.0 mTorr for 8 min) using a reactive ion etcher (RIE, Plasma-Therm Versaline LL-ICP, St. Petersburg, FL), and then the top layer of Ti was etched with 2% aqueous HF to expose the Au surface. Finally, the wafers were coated with a 5.0-μm layer of SPR3612 as a protective layer. A wafer saw (DISCO DAD3240, Tokyo, Japan) was used to dice the wafer into individual chips. Prior to use, the chips were sonicated in acetone for 10 min, followed by rinsing with methanol and isopropanol to remove the protective layer.

3. ELISA Measurements

Cathepsin B concentrations were determined using enzyme-linked immunosorbent assay (ELISA) kits from R&D Systems. A typical 64-well plate design used for ELISA measurements of a series of various concentrations of recombinant human cathepsin B diluted in 1% BSA in 0.5×PB buffer or 2.5% HS added to 1% BSA in 0.5×PB.

TABLE

| ELISA Plate Design | | | | | | | | |
| --- | --- | --- | --- | --- | --- | --- | --- | --- |
| | HS | | | | BSA | | | |
| | 1 | 2 | 3 | 4 | 5 | 6 | 7 | 8 |
| A | | 250 pM | | | | 250 pM | | |
| B | | 200 pM | | | | 200 pM | | |
| C | | 150 pM | | | | 150 pM | | |
| D | | 100 pM | | | | 100 pM | | |
| E | | 50 pM | | | | 50 pM | | |
| F | | 25 pM | | | | 25 pM | | |
| G | | | | 2.5 HS Blank | | | | |
| H | | | | BSA Blank | | | | |

First, the wells were coated with the primary antibody by incubation with 100 μL of PBS containing 4.00 g/mL mouse anti-human cathepsin B antibodies at room temperature for 8-10 hours. Each well was washed three times with 0.05% Tween® 20 in a standard PBS solution and dried by tapping them against a firm surface padded with sterile laboratory tissue. The plates were then passivated by incubation with 300 μL 1% BSA in PBS buffer per well at room temperature for 1 hour and washed with 0.05% Tween® 20 in the PBS buffer. Samples with rhCB were prepared via serial dilution from 1.0 nM stock solutions in 0.5×PB buffer containing 1% BSA according to the plate design. Another series were prepared in 0.5×PB buffer containing 1% BSA after adding 2.5% HS. When applicable, solutions of 36 nM rhCB and 90% HS were activated by incubation in 2-(4-morpholino) ethanesulfonic acid (MES) buffer containing 5 mM dithiothreitol (DTT) at room temperature for 15 minutes before diluting into proper rhCB concentration for ELISA measurements. Varied concentrations of HS were also prepared via serial dilution with 1% BSA in 0.5×PB for generating a calibration curve. In some experiments, the HS was activated in MES and DTT same as above and then diluted to desired concentrations.

ELISA measurements were performed in quadruplicate on the 96-well plates. To the quadruplicate wells, 100 μL of each sample was added, incubated at room temperature for 2 hours and washed with 0.05% Tween® 20 in the PBS buffer. Following this, the plates were further incubated with 100 μL of 50.0 ng/mL biotinylated goat anti-human cathepsin B antibodies in 1% BSA in PBS at room temperature for 2 hours and washed with 0.05% Tween® 20 in the PBS buffer. The plates were then incubated with 100 μL of 20 ng/mL streptavidin-conjugated horseradish peroxidase prepared in 1% BSA in PBS at room temperature for 20 minutes in the absence of light and washed with 0.05% Tween® 20 in the PBS buffer. Finally, the plates were incubated with 100 μL of a 1:1 (volume ratio) solution of hydrogen peroxide and 3,3',5,5'-tetramethylbenzidine (TMB) at room temperature for 20 minutes in the absence of light, which provided signal amplification via the catalytic oxidation of TMB. The reaction was stopped by addition of 50 μL 1.0 M sulfuric acid per well to convert it into a yellow product. Once developed, the OD of the wells was read immediately at 450 nm wavelength. FIG. 26A shows the typical 64-well plate design used for the ELISA measurement. The cathepsin B ELISA experiment in this study was diluted in 1% BSA in 0.5×PB buffer (blue) or 2.5% human serum with 1% BSA in 0.5×PB buffer (orange). An image of a developed plate following the above procedure is shown in FIG. 26B.

4. Michaelis-Menten Model for Electrochemical Data Analysis

Our previous studies have described the exponential kinetics of the proteolysis reaction by the Michaelis-Menten model for the heterogeneous enzymatic reaction:

$$E + S_s \underset{k_{-1}}{\overset{k_1}{\rightleftarrows}} ES_s \overset{k_{cat}}{\Longrightarrow} E + P_s + P \qquad (S1)$$

where E is the active enzyme, $S_s$ is the surface-functionalized peptide-Fc substrate, $ES_s$ is the enzyme-substrate complex on the electrode surface, $P_s$ is the peptide fragment remaining on the surface after proteolysis cleavage, and P is the released peptide fragment containing Fc, and $k_1$, $k_1$, and $k_{cat}$ are the rate constant of related reactions. Based on the steady-state assumption, the reaction rate can be described as $$v = -\frac{d\Gamma_{S_s}}{dt} = \frac{k_{cat}}{K_M + [E]_0}[E]_0 \Gamma_{S_s}, \qquad (S2)$$

where $\Gamma_{S_s}$ is the surface concentration of peptide-Fc substrate, $K_M$ is the Michaelis-Menten constant $K_M=(k_{cat}+k_{-1})/k_1$ and $[E]_0$ is the active enzyme concentration. Because the ACV peak current is proportional to the Fc-moiety density. The reaction rate can be also written as:

$$-\frac{d(i_p/i_{p0})}{dt} = \frac{k_{cat}}{K_M + [E_0]}[E]_0\left(\frac{i_p}{i_{p0}}\right). \qquad (S3)$$

If we assume $K_M \gg [E]_0$, we can derive $$-\frac{d(i_p/i_{p0})}{dt} \approx \frac{k_{cat}}{K_M}[E]_0\left(\frac{i_p}{i_{p0}}\right). \qquad (S4)$$

After integrating equation (5), we have $$\frac{i_p}{i_{p0}} = \exp\left(-\frac{k_{cat}}{K_M}[E]_0 t\right) = \exp[-t/\tau]. \qquad (S5)$$

Finally, we have the relationship between the exponential decay time constant c and the fundamental protease properties as $$\frac{1}{\tau} = \left(\frac{k_{cat}}{K_M}\right)[E]_0. \qquad (S6)$$

Example 4

Alternative Redox Moieties

In this example, the electrochemical tag ferrocene (Fc) may be replaced by other reversible redox tags. For example, a methylene blue (MB) tag can be used to replace the Fc at the distal end of the peptide. MB has been reported to provide a more stable signal versus time than Fc. The synthesis of MB-attached peptide as the substrate for detection the proteolytic activity of a specific protease (enzyme) and method to use it in electrochemical detection are described below.

Syntheses of methylene blue attached substrate peptides. The reaction scheme is depicted in FIG. 33. Two novel MB analogs 2 and 3 are synthesized from basic blue 24 (1), a commercially available material. N-Boc protected Peptide 15 is activated with HATU followed by the condensation with either methylene blue 2 or 3, and trifluoroacetic acid (TFA) to give modified peptides 15a or 15b. Methylene blue 2 (R=Et or Me) is prepared by the alkylation of compound 1 (commercially available from Fisher Scientifics) with 1 equivalent of ethyl iodide or methyl iodide. Methylene blue 3 (R=Et or Me) is prepared by a reductive amination of compound 2 (R=Et or Me) with 1 equivalent of N-Boc-3-aminopropanal in methanol followed by sodium cyanoborohydride and then TFA. Similar methods can be applied to synthesize other MB-attached peptide as the substrates for target proteases.

Electrochemical detection of protease activity using MB-attached peptide functionalized on Au MEAs. The MB-attached peptide is covalently tethered to the carboxylic group on the terminal surface of self-assembled thiol monolayer on the Au MEA by forming amide bond, based on the same method in the former embodiment.

A reduction current, due to gaining two electrons per MB, is measured with AC voltammetry (ACV) by applying a DC potential ramp from about 0 to −0.50 V vs. a Ag/AgCl (3 M KCl) reference electrode at the scan rate of 5 to 100 mV/s. A sinusoidal AC voltage waveform of 5-1000 Hz frequency and 5 to 200 mV amplitude is superimposed on the DC potential ramp. The corresponding AC current is measured during the DC potential scan. The AC current shows a peak in the range of −0.20 to −0.40 V vs. a Ag/AgCl (3 M KCl) reference electrode. The background subtracted peak AC current is proportional to the amount of MB attached on the gold electrode surface via the peptide. The peak current is monitored over time using continuously repeated ACV measurements. After the electrodes are stabilized for about 10 minutes, the specific protease is added to the electrochemical cell. The AC peak current starts to decrease exponentially vs. time due to cleavage of the peptide by the protease. The MB tag on the cleaved peptide fragment is released into the bulk solution. This provides a curve to reflect the kinetics of the proteolysis process. The inverse of the exponential decay time constant indicates the activity of the protease, as described in the above embodiment. The quantitative analysis is the same as Examples 1 and 3 using the Fc redox tag.

The invention claimed is:

1. A microelectrode array for simultaneous detection of two or more target protease biomarkers, said array comprising:

a plurality of individually addressable microelectrodes spaced apart from one another and separated by an insulating layer, each microelectrode comprising an electrically conductive surface consisting of gold, an alkanethiol monolayer on said gold surface having a plurality of peptides extending therefrom, said alkanethiol monolayer comprising thiol moieties adsorbed to said gold surface and a plurality of terminal carboxylic acid groups and hydroxyl groups distal from the gold surface in a ratio, each peptide comprising a proximal end having an amino group covalently attached to a respective carboxylic acid group in said alkanethiol monolayer and a distal end that is spaced apart from said surface, said distal end of each peptide comprising a redox moiety attached thereto, each of said peptides comprising a consensus sequence for a target protease biomarker, wherein the ratio of carboxylic acid to hydroxyl groups in the alkanethiol monolayer yields a spacing of 2.46 nm to 7.9 nm between each peptide;

wherein each of said microelectrodes comprising a plurality of said peptides extending therefrom;

wherein at least one microelectrode comprises a plurality of peptides comprising first consensus sequences for detection of a first target protease biomarker and wherein at least a second microelectrode comprises a plurality of peptides comprising second consensus sequences different from said first consensus sequences for detection of a second target protease biomarker different from said first target protease biomarker;

said array being configured to simultaneously detect the activity of two or more target protease biomarkers present within a biological sample through cleavage of a respective consensus sequence by a target protease biomarker, if present, which releases said redox moiety effecting a detectable decrease in alternating current (AC) peak current across said array over time, as measured by continuously repeated AC voltammetry, due to release of said redox moiety in proximity to said electrode surface.

2. The microelectrode array of claim 1, wherein each microelectrode is spaced A apart by 500 μm to 2 mm.

3. The microelectrode array of claim 1, wherein each of said microelectrodes is configured to detect a different target protease biomarker.

4. The microelectrode array of claim 1, wherein said redox moiety is selected from the group consisting of ferrocenes, methylene blues, viologens, anthraquinones, ethidium bromide, daunomycin, ruthenium, bis-pyridine, tris-pyridine, bis-imidizole, and analogs thereof.

5. The microelectrode array of claim 1, each of said peptides comprising a consensus sequence for a target protease biomarker selected from the group consisting of:

| Target Protease | SEQ ID NO: |
| --- | --- |
| Cathepsin B | residues 2-5 of 1 |
| Cathepsin B | 4 |
| Cathepsin B | 1 |
| Cathepsin B | 6 |
| Cathepsin B | 7 |
| Cathepsin B | 8 |
| Cathepsin B | 9 |
| ADAM-10 | 10 |
| ADAM-10 | residues 2-5 of SEQ 11 |
| ADAM-10 | residues 2-7 of SEQ 11 |
| ADAM-10 | residues 2-8 of SEQ 11 |
| ADAM-10 | 11 |
| ADAM-10 | 11 |
| ADAM-17 | 11 |
| Cathepsin B | 2 |
| Cathepsin B | 3 |
| ADAM-17 | residues 3-8 of SEQ 11 |
| Cathepsin D | 12 |
| ADAM-17 | 13 |
| ADAM-17 | 14 |
| Cathepsin D | 15 |
| Cathepsin D | 16 |
| MMP-9 | 17 |
| MMP-9 | 18 |
| MMP-9 | 19 |
| MMP-9 | 20 |
| MMP-9 | 21 |

6. An electronic chip comprising a microelectrode array according to claim 1, further comprising contact pads, each contact pad being connected to a respective microelectrode via a respective conductive lead configured for continuous ACV interrogation and detection of AC electrical current and decrease of AC peak current over time upon contact of a microelectrode with a target protease biomarker.

7. A system for simultaneous electrochemical detection of two or more target protease biomarkers, said system comprising an electronic chip according to claim 6, wherein said chip is positioned within an electrochemical cell, said electrochemical cell being electrically connected via a breakout box to a potentiostat, said system further comprising a microfluidic channel in fluid communication with a sample inlet and sample outlet and configured to direct a biological sample into contact with said microelectrode array, said system further comprising one counter electrode and one reference electrode, wherein said counter electrode and said reference electrode are each printed on said chip or positioned or deposited on a coverslip or cover aligned over said microelectrode array and in contact with the microfluidic channel and biological sample flowing therethrough.

8. A method of simultaneously detecting two or more protease biomarkers within a biological sample comprising contacting a microelectrode array according to claim 1 with a biological sample containing or suspected of containing two or more protease biomarkers and detecting a decrease in the AC peak electric current across said array over time, as measured by continuously repeated AC voltammetry.

9. The method of claim 8, wherein cleavage of a consensus sequence by a target protease biomarker results in a detectable exponential decrease in the peak current as measured by AC voltammetry.

10. The method of claim 9, wherein an inverse of the exponential decrease time constant is correlated with activity of the target protease biomarker in the biological sample.

11. The method of claim 8, wherein the biological sample is selected from the group consisting of blood, serum, urine, saliva, sweat, exhaled breath condensate, cell lysate, tissue lysate, and tissue biopsies.

12. The method of claim 8, wherein aliquots of a collected biological sample can be directly contacted with said array without dilution.

13. The method of claim 8, further comprising diluting said biological sample in a modified buffer before contacting with said array, wherein said modified buffer has a pH ranging from 7 to 7.5, wherein said modified buffer is a phosphate-based buffer that is essentially free of chloride salts.

*     *     *     *     *

```
                        SEQUENCE LISTING

<160> NUMBER OF SEQ ID NOS: 21

<210> SEQ ID NO 1
<211> LENGTH: 6
<212> TYPE: PRT
<213> ORGANISM: Artificial Sequence
<220> FEATURE:
<223> OTHER INFORMATION: Synthetic substrate peptide

<400> SEQUENCE: 1

Pro Leu Arg Phe Gly Ala
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic substrate peptide

<400> SEQUENCE: 2

Pro Leu Ala Phe Val Ala
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic substrate peptide

<400> SEQUENCE: 3

Pro Leu Ala Gly Val Ala
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic substrate peptide

<400> SEQUENCE: 4

Lys Val Arg Phe Val Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic substrate peptide

<400> SEQUENCE: 5

Pro Thr Arg Phe Val Gly
1               5

<210> SEQ ID NO 6
<211> LENGTH: 6
<212> TYPE: PRT
<213> ORGANISM: Artificial Sequence
```

```
<220> FEATURE:
<223> OTHER INFORMATION: Synthetic substrate peptide

<400> SEQUENCE: 6

Pro Val Gly Phe Val Ala
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic substrate peptide

<400> SEQUENCE: 7

Ala Pro Leu Arg Phe Gly Ala Ala
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic substrate peptide

<400> SEQUENCE: 8

Pro Leu Gly Phe Val Ala
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic substrate peptide

<400> SEQUENCE: 9

Pro Leu Gly Gly Val Ala
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic substrate peptide

<400> SEQUENCE: 10

Phe Leu Met Gln Val Ala
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic substrate peptide

<400> SEQUENCE: 11

Lys Pro Leu Gly Leu Ser Ala Arg
1               5

<210> SEQ ID NO 12
<211> LENGTH: 7
<212> TYPE: PRT
<213> ORGANISM: Artificial Sequence
<220> FEATURE:
```

```
<223> OTHER INFORMATION: Synthetic substrate peptide

<400> SEQUENCE: 12

Pro Leu Gly Leu Phe Ala Arg
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic substrate peptide

<400> SEQUENCE: 13

Ala Gly Leu Phe Ala Arg
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic substrate peptide

<400> SEQUENCE: 14

Ala Gly Leu Phe Leu Arg
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic substrate peptide

<400> SEQUENCE: 15

Pro Leu Gly Leu Ala Arg
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic substrate peptide

<400> SEQUENCE: 16

Pro Phe Leu Gly Ala Arg
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic substrate peptide

<400> SEQUENCE: 17

Pro Arg Phe Ile Ser Ala
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic substrate peptide
```

```
<400> SEQUENCE: 18

Pro Arg Thr Phe Ser Ala
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic substrate peptide

<400> SEQUENCE: 19

Pro Arg Thr Ile Phe Ala
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic substrate peptide

<400> SEQUENCE: 20

Pro Arg Thr Ile Ser Ala
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic substrate peptide

<400> SEQUENCE: 21

Pro Phe Thr Ile Ser Ala
1               5
```